US010598667B2

United States Patent
Lam et al.

(10) Patent No.: US 10,598,667 B2
(45) Date of Patent: Mar. 24, 2020

(54) FUNCTIONAL ILLUMINATION IN LIVING CELLS

(71) Applicant: The Regents of the University of California, Oakland, CA (US)

(72) Inventors: Kit S. Lam, Davis, CA (US); Lin Tian, Davis, CA (US); Sara Ahadi, Davis, CA (US); Ruiwu Liu, Sacramento, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 39 days.

(21) Appl. No.: 14/780,484

(22) PCT Filed: Mar. 26, 2014

(86) PCT No.: PCT/US2014/031824
§ 371 (c)(1),
(2) Date: Sep. 25, 2015

(87) PCT Pub. No.: WO2014/160752
PCT Pub. Date: Oct. 2, 2014

(65) Prior Publication Data
US 2016/0313341 A1    Oct. 27, 2016

Related U.S. Application Data

(60) Provisional application No. 61/805,320, filed on Mar. 26, 2013, provisional application No. 61/837,392, filed on Jun. 20, 2013.

(51) Int. Cl.
*G01N 33/68* (2006.01)
*C07K 14/00* (2006.01)
*G01N 33/58* (2006.01)

(52) U.S. Cl.
CPC ......... *G01N 33/6803* (2013.01); *C07K 14/00* (2013.01); *G01N 33/582* (2013.01); *C07K 2319/60* (2013.01); *C07K 2319/90* (2013.01)

(58) Field of Classification Search
CPC ............ G01N 33/6803; G01N 33/582; C07K 2319/60; C07K 14/00; C07K 2319/90
See application file for complete search history.

(56) References Cited

U.S. PATENT DOCUMENTS

| 2007/0212700 A1 * | 9/2007 | Ranganathan ......... G16B 30/00 435/6.16 |
| 2010/0233676 A1 | 9/2010 | Kelly et al. |
| 2012/0040860 A1 | 2/2012 | Denu et al. |

FOREIGN PATENT DOCUMENTS

| CA | 2082770 A1 * | 8/1993 | ............... C07K 7/08 |
| WO | 2014044011 A2 | 5/2004 | |

OTHER PUBLICATIONS

Szent-Gyorgyi et al, Fluorogen-activating single-chain antibodies for imaging cell surface proteins, Nature Biotechnology, 2008, 26, pp. 235-240.*

Juskowiak, "Sequence-Specific Reactivity of Short Peptides: Peptide Photooxidative Fluorogenesis and Peptide Tags for Small Molecule Fluorescent Probes," Thesis dissertation from the University of California Irvine and available as UMI Microfilm Document 3355899, published 2009 [online]. [Retrieved on Oct. 9, 2014]. Retrieved from the Internet: <URL: http://gradworks.umi.com/3355899.pdf>, pp. 1-447.

McLafferty, et al., "M13 bacteriophage displaying disulfide-constrained microproteins," *Gene*, vol. 128, No. 1, pp. 29-36 (1993).

International Search Report for International Application No. PCT/US2014/031824 dated Nov. 3, 2014, 5 pages.

\* cited by examiner

*Primary Examiner* — Karlheinz R. Skowronek
*Assistant Examiner* — Li N Komatsu
(74) *Attorney, Agent, or Firm* — Mintz, Levin, Cohn, Ferris, Glovsky & Popeo, P.C.

(57) ABSTRACT

The present invention provides kits and methods for detecting peptides that change of the fluorescence of dyes upon binding to the dye. In addition, the invention provides methods for identifying said peptides.

12 Claims, 21 Drawing Sheets
Specification includes a Sequence Listing.

FIG. 1A Triarylmethane dye
Methyl violet (MV) dye
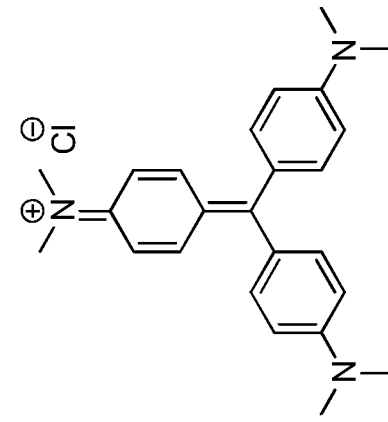
MV-2B
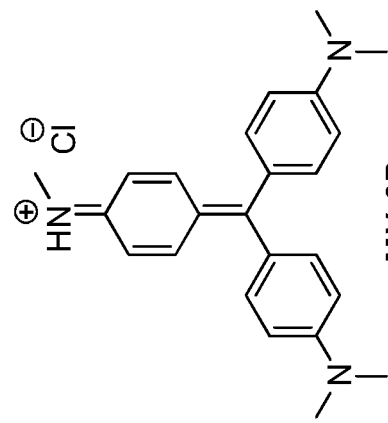
MV-6B
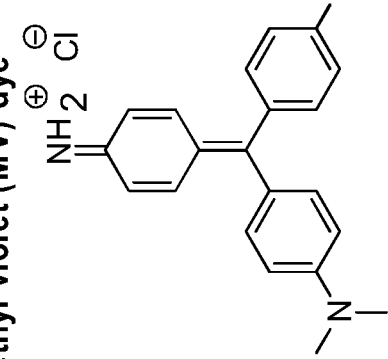
MV-10B
(Crystal violet)
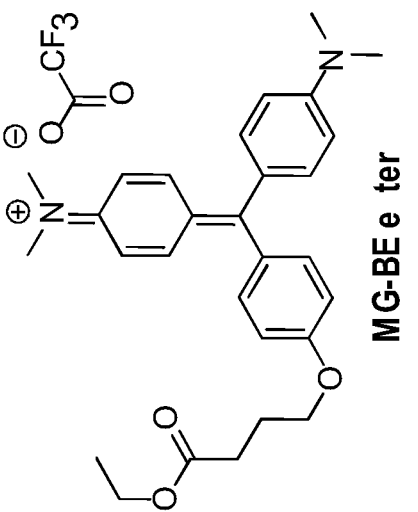
MG-BE ester
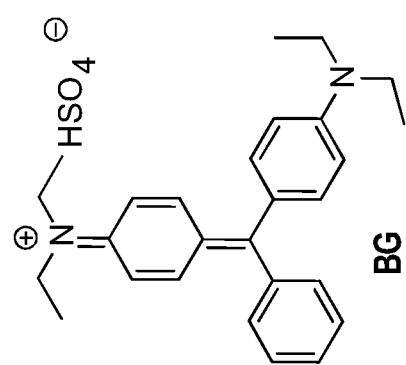
BG
Malachite green dye
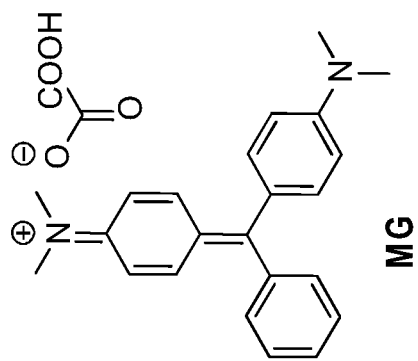
MG

FIG. 1A (CONT.)
Phenol dye
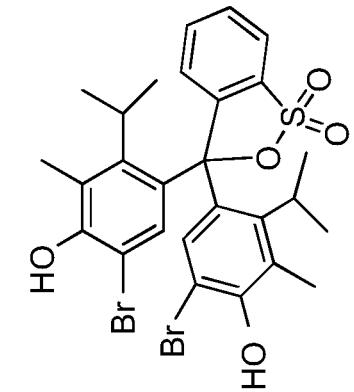
Bromothymol blue
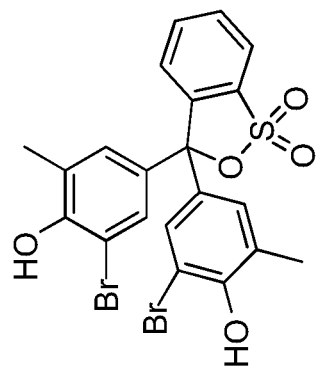
Bromocresol purple
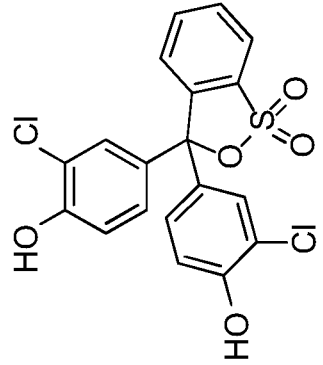
Chlorophenol red
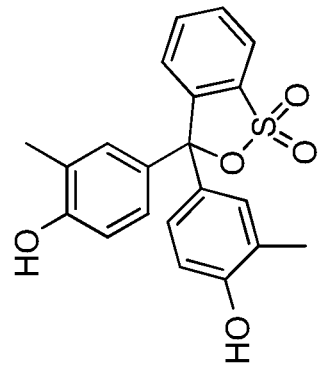
Cresol red

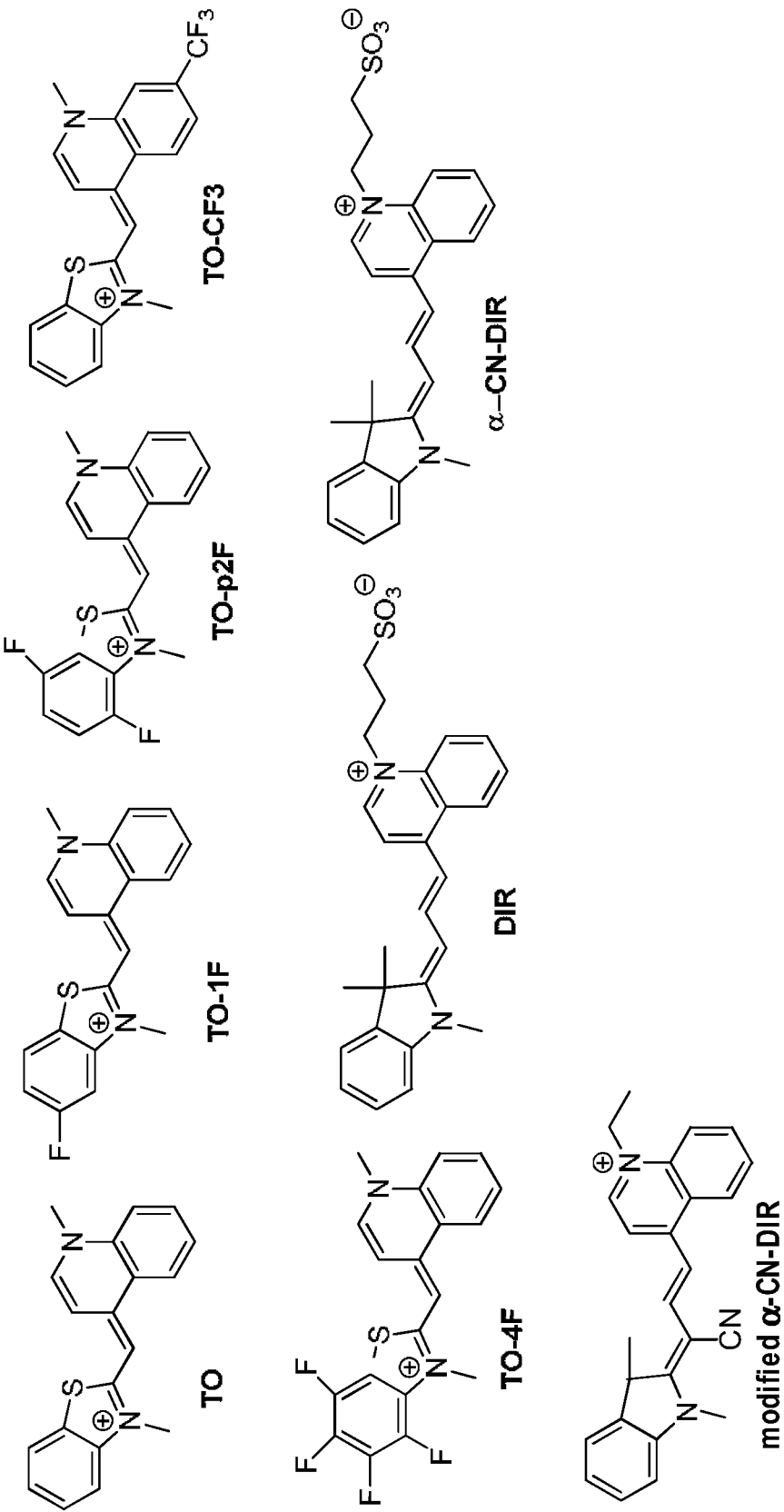
FIG. 1B Cynanin dye

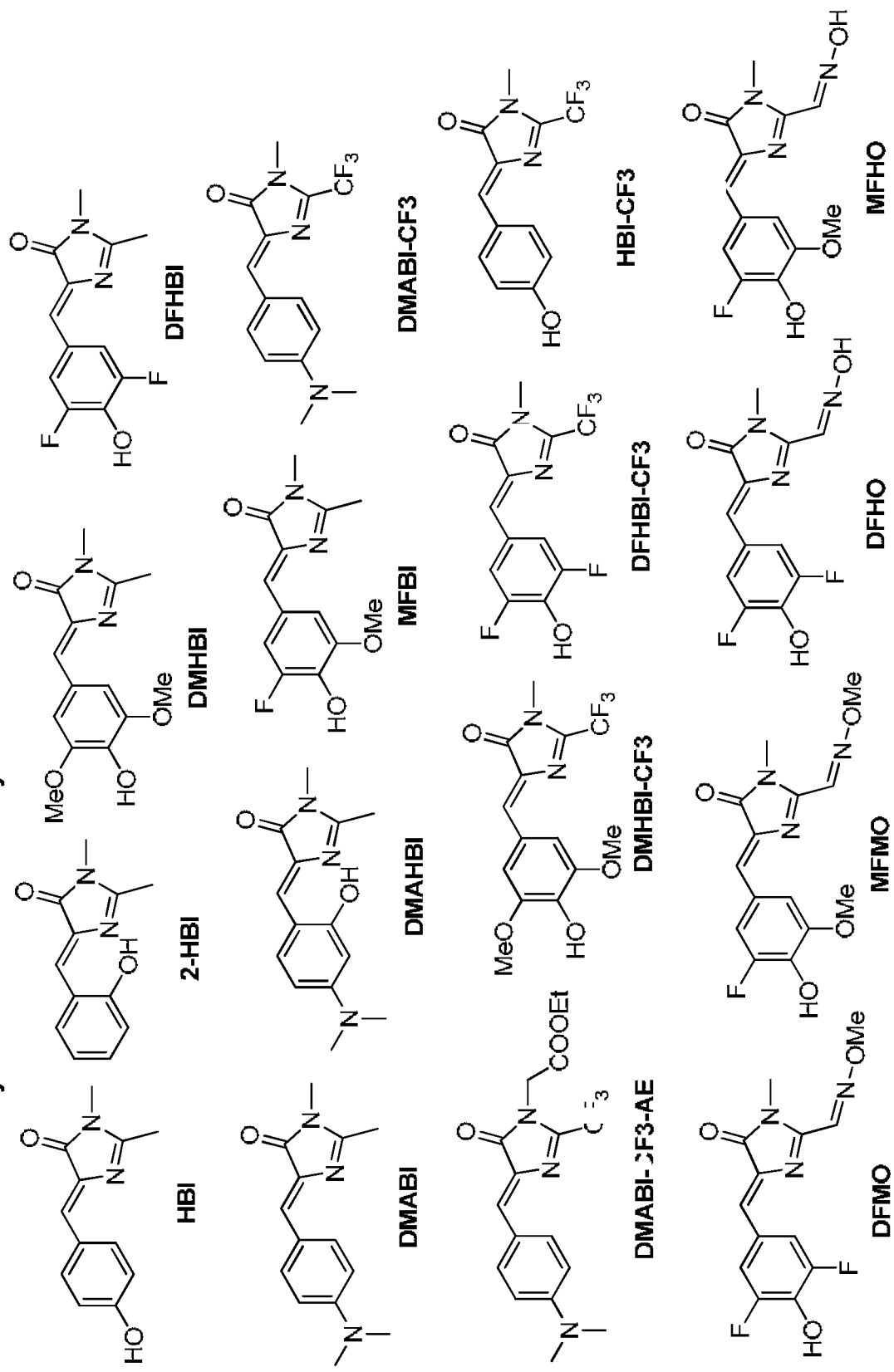
FIG. 1C Benzylidene imidazolinone dye

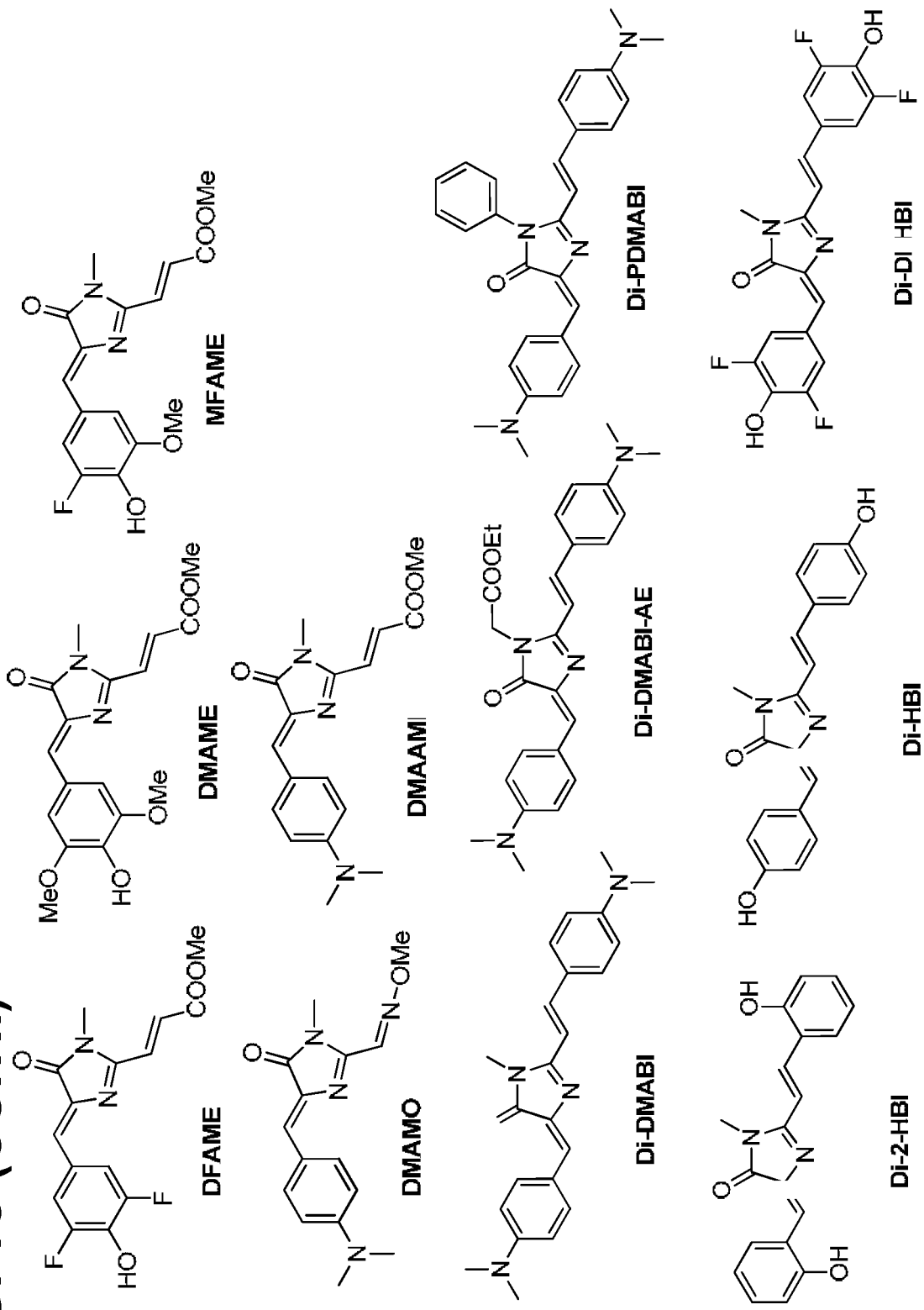

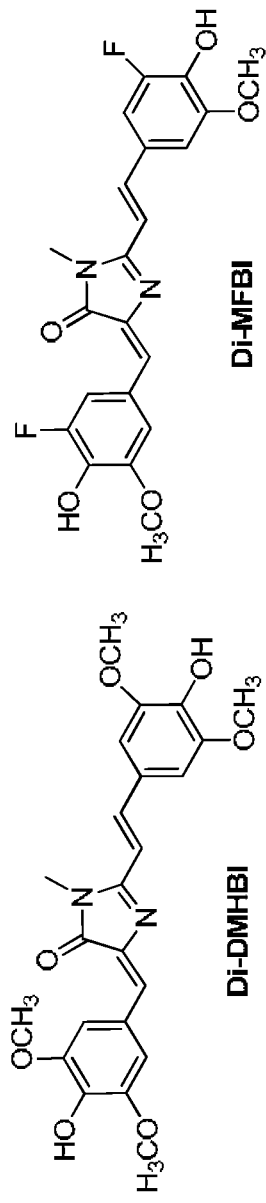
FIG. 1C (CONT.)
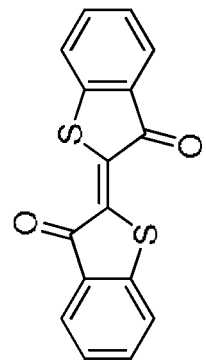
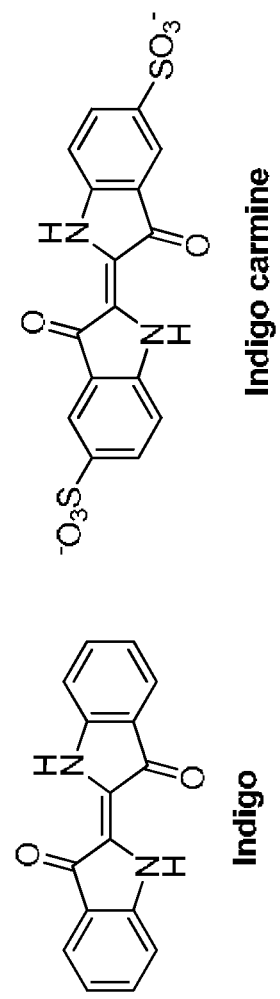
FIG. 1D
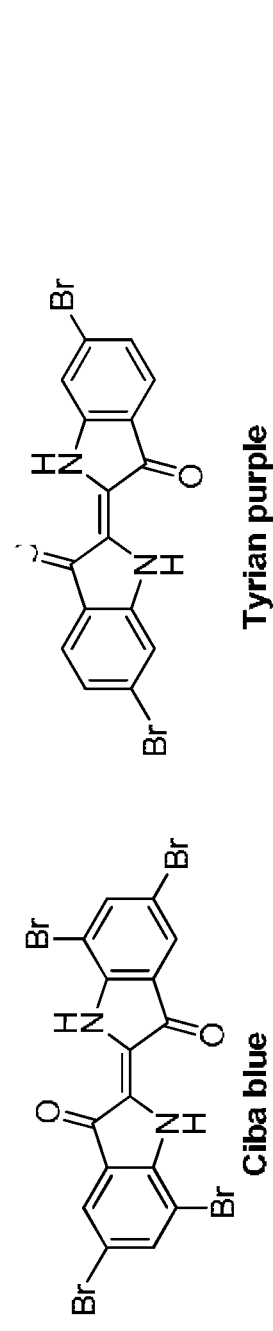

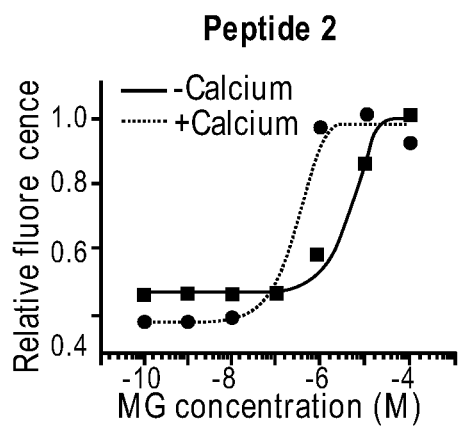
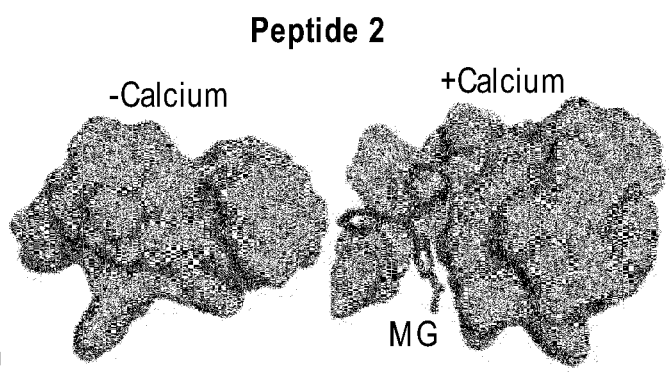
FIG. 11A    FIG. 11B
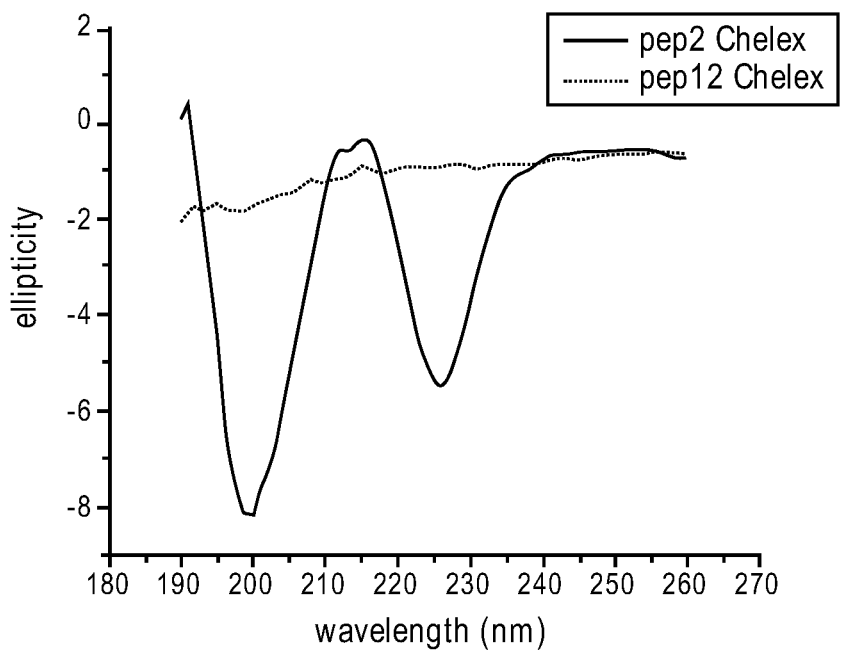
FIG. 12

FIG. 13A  Peptide 2 Alanine Walk
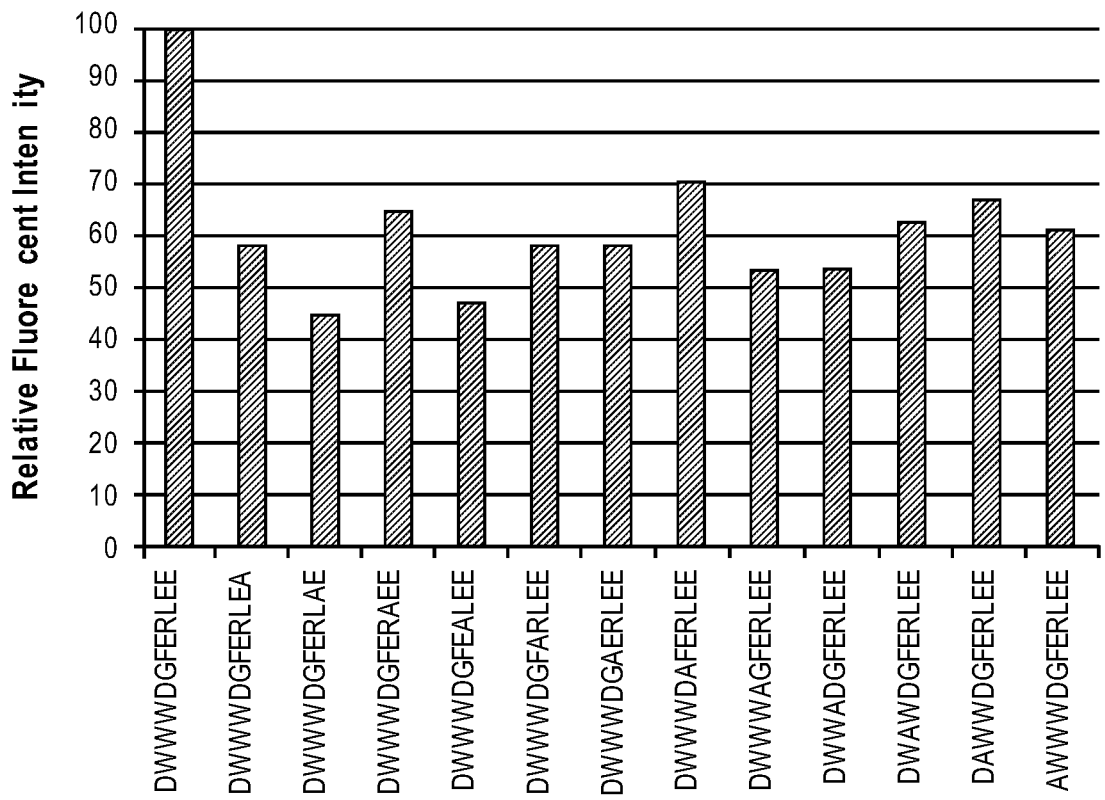
FIG. 13B  Peptide 2 Deletion
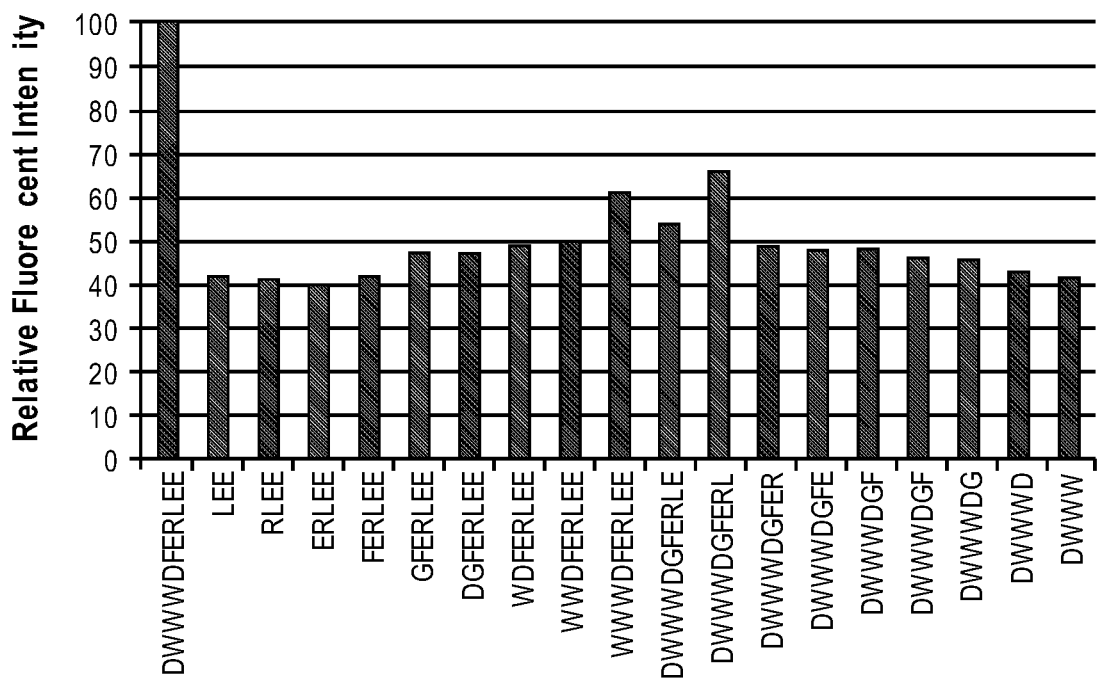

FIG. 18

| | OBOC Library design & development of illuminant | | Genetic illuminant for |
|---|---|---|---|
| | OBOC library design | Screening approache | |
| 1 | XXXXXXXXXXX-bead | | Protein trafficking Protein localization |
| 2 | XXXXXX----XXXXXX-bead | | Protein-protein interaction Protein conformational change |
| 3 | XXXXXSPXXXX-bead<br>XXXXRRXSXXXX-bead<br>XXXXRRXS(P)XXXX-bead<br>XXXXS(P)PXXXX-bead<br>RC(Me)S(P)TTG(X)nGK(Ac)AP-bead<br>XXXXART(P)K(Me)QT-bead | Enzymatic reaction<br>Chemical synthesis | Post-translational modification: Phosphorylation Acetylation Methylation<br>Peptide<br>PEG<br>MG<br>Post-translational modification<br>Bound MG |

FIG. 19
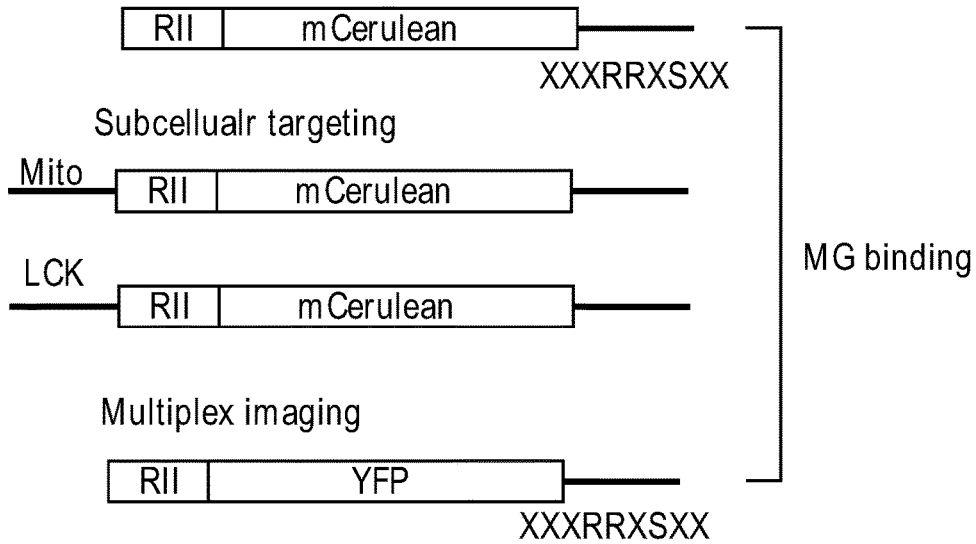
GESI for probing PKA — XXXRRXSXX
Subcellualr targeting
Mito
LCK
MG binding
Multiplex imaging — XXXRRXSXX
GESI for probing JNK
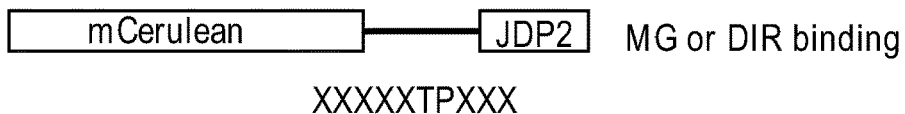
MG or DIR binding
XXXXXTPXXX
FIG. 20A
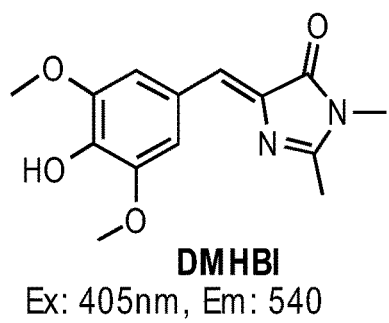
DMHBI
Ex: 405nm, Em: 540
FIG. 20B
Linear Library: DXXXXGXXXXXE
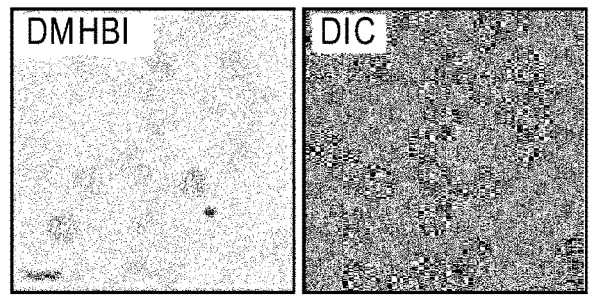
DMHBI | DIC
FIG. 20C
H2 peptide library
(X)n-SGRGKQG—H2 (with P and Ac modifications)
FIG. 20D
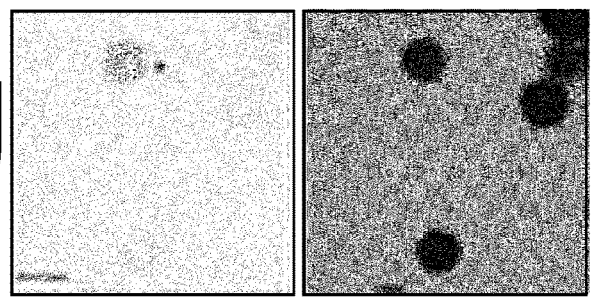

SEQUENCE LISTING

<160> NUMBER OF SEQ ID NOS: 228

<210> SEQ ID NO 1
<211> LENGTH: 22
<212> TYPE: PRT
<213> ORGANISM: Artificial Sequence

```
<220> FEATURE:
<223> OTHER INFORMATION: synthetic genetically encoded small illuminant
      (GESI) peptide substrate for protein kinase
<220> FEATURE:
<221> NAME/KEY: VARIANT
<222> LOCATION: (1)..(4)
<223> OTHER INFORMATION: Xaa = any amino acid
<220> FEATURE:
<221> NAME/KEY: VARIANT
<222> LOCATION: (5)..(9)
<223> OTHER INFORMATION: Xaa = any amino acid, may be present or absent
<220> FEATURE:
<221> NAME/KEY: VARIANT
<222> LOCATION: (12)..(14)
<223> OTHER INFORMATION: Xaa = any amino acid
<220> FEATURE:
<221> NAME/KEY: PHOSPHORYLATION
<222> LOCATION: (13)..(13)
<223> OTHER INFORMATION: Ser can be phosphorylated
<220> FEATURE:
<221> NAME/KEY: VARIANT
<222> LOCATION: (15)..(19)
<223> OTHER INFORMATION: Xaa = any amino acid, may be present or absent
<220> FEATURE:
<221> NAME/KEY: VARIANT
<222> LOCATION: (20)..(22)
<223> OTHER INFORMATION: Xaa = any amino acid

<400> SEQUENCE: 1

Xaa Xaa Xaa Xaa Xaa Xaa Xaa Xaa Xaa Arg Arg Xaa Ser Xaa Xaa Xaa
1               5                   10                  15

Xaa Xaa Xaa Xaa Xaa Xaa
            20

<210> SEQ ID NO 2
<211> LENGTH: 22
<212> TYPE: PRT
<213> ORGANISM: Artificial Sequence
<220> FEATURE:
<223> OTHER INFORMATION: synthetic genetically encoded small illuminant
      (GESI) peptide substrate for protein kinase
<220> FEATURE:
<221> NAME/KEY: VARIANT
<222> LOCATION: (1)..(3)
<223> OTHER INFORMATION: Xaa = any amino acid
<220> FEATURE:
<221> NAME/KEY: VARIANT
<222> LOCATION: (4)..(8)
<223> OTHER INFORMATION: Xaa = any amino acid, may be present or absent
<220> FEATURE:
<221> NAME/KEY: VARIANT
<222> LOCATION: (11)..(13)
<223> OTHER INFORMATION: Xaa = any amino acid
<220> FEATURE:
<221> NAME/KEY: PHOSPHORYLATION
<222> LOCATION: (12)..(12)
<223> OTHER INFORMATION: Thr can be phosphorylated
<220> FEATURE:
<221> NAME/KEY: VARIANT
<222> LOCATION: (14)..(18)
<223> OTHER INFORMATION: Xaa = any amino acid, may be present or absent
<220> FEATURE:
<221> NAME/KEY: VARIANT
<222> LOCATION: (19)..(22)
<223> OTHER INFORMATION: Xaa = any amino acid

<400> SEQUENCE: 2

Xaa Xaa Xaa Xaa Xaa Xaa Xaa Xaa Arg Arg Xaa Thr Xaa Xaa Xaa Xaa
1               5                   10                  15

Xaa Xaa Xaa Xaa Xaa Xaa
            20

<210> SEQ ID NO 3
```

```
<211> LENGTH: 21
<212> TYPE: PRT
<213> ORGANISM: Artificial Sequence
<220> FEATURE:
<223> OTHER INFORMATION: synthetic genetically encoded small illuminant
      (GESI) peptide substrate for protein kinase
<220> FEATURE:
<221> NAME/KEY: VARIANT
<222> LOCATION: (1)..(5)
<223> OTHER INFORMATION: Xaa = any amino acid
<220> FEATURE:
<221> NAME/KEY: VARIANT
<222> LOCATION: (6)..(10)
<223> OTHER INFORMATION: Xaa = any amino acid, may be present or absent
<220> FEATURE:
<221> NAME/KEY: PHOSPHORYLATION
<222> LOCATION: (11)..(11)
<223> OTHER INFORMATION: Ser may be phosphorylated
<220> FEATURE:
<221> NAME/KEY: VARIANT
<222> LOCATION: (12)..(12)
<223> OTHER INFORMATION: Xaa = any amino acid
<220> FEATURE:
<221> NAME/KEY: VARIANT
<222> LOCATION: (13)..(17)
<223> OTHER INFORMATION: Xaa = any amino acid, may be present or absent
<220> FEATURE:
<221> NAME/KEY: VARIANT
<222> LOCATION: (18)..(21)
<223> OTHER INFORMATION: Xaa = any amino acid

<400> SEQUENCE: 3

Xaa Xaa Xaa Xaa Xaa Xaa Xaa Xaa Xaa Xaa Ser Xaa Xaa Xaa Xaa Xaa
1               5                   10                  15

Xaa Xaa Xaa Xaa Xaa
            20

<210> SEQ ID NO 4
<211> LENGTH: 21
<212> TYPE: PRT
<213> ORGANISM: Artificial Sequence
<220> FEATURE:
<223> OTHER INFORMATION: synthetic genetically encoded small illuminant
      (GESI) peptide substrate for protein kinase
<220> FEATURE:
<221> NAME/KEY: VARIANT
<222> LOCATION: (1)..(5)
<223> OTHER INFORMATION: Xaa = any amino acid
<220> FEATURE:
<221> NAME/KEY: VARIANT
<222> LOCATION: (6)..(10)
<223> OTHER INFORMATION: Xaa = any amino acid, may be present or absent
<220> FEATURE:
<221> NAME/KEY: PHOSPHORYLATION
<222> LOCATION: (11)..(11)
<223> OTHER INFORMATION: Thr can be phosphorylated
<220> FEATURE:
<221> NAME/KEY: VARIANT
<222> LOCATION: (12)..(12)
<223> OTHER INFORMATION: Xaa = any amino acid
<220> FEATURE:
<221> NAME/KEY: VARIANT
<222> LOCATION: (13)..(17)
<223> OTHER INFORMATION: Xaa = any amino acid, may be present or absent
<220> FEATURE:
<221> NAME/KEY: VARIANT
<222> LOCATION: (18)..(21)
<223> OTHER INFORMATION: Xaa = any amino acid

<400> SEQUENCE: 4

Xaa Xaa Xaa Xaa Xaa Xaa Xaa Xaa Xaa Xaa Thr Xaa Xaa Xaa Xaa Xaa
1               5                   10                  15

Xaa Xaa Xaa Xaa Xaa
            20
```

<210> SEQ ID NO 5
<211> LENGTH: 20
<212> TYPE: PRT
<213> ORGANISM: Artificial Sequence
<220> FEATURE:
<223> OTHER INFORMATION: synthetic genetically encoded small illuminant
      (GESI) peptide substrate for protein kinase
<220> FEATURE:
<221> NAME/KEY: VARIANT
<222> LOCATION: (1)..(4)
<223> OTHER INFORMATION: Xaa = any amino acid
<220> FEATURE:
<221> NAME/KEY: VARIANT
<222> LOCATION: (5)..(9)
<223> OTHER INFORMATION: Xaa = any amino acid, may be present or absent
<220> FEATURE:
<221> NAME/KEY: PHOSPHORYLATION
<222> LOCATION: (10)..(10)
<223> OTHER INFORMATION: Ser can be phosphorylated
<220> FEATURE:
<221> NAME/KEY: VARIANT
<222> LOCATION: (12)..(12)
<223> OTHER INFORMATION: Xaa = any amino acid
<220> FEATURE:
<221> NAME/KEY: VARIANT
<222> LOCATION: (13)..(17)
<223> OTHER INFORMATION: Xaa = any amino acid, may be present or absent
<220> FEATURE:
<221> NAME/KEY: VARIANT
<222> LOCATION: (18)..(20)
<223> OTHER INFORMATION: Xaa = any amino acid

<400> SEQUENCE: 5

Xaa Xaa Xaa Xaa Xaa Xaa Xaa Xaa Xaa Ser Pro Xaa Xaa Xaa Xaa Xaa
1               5                   10                  15

Xaa Xaa Xaa Xaa
            20

<210> SEQ ID NO 6
<211> LENGTH: 20
<212> TYPE: PRT
<213> ORGANISM: Artificial Sequence
<220> FEATURE:
<223> OTHER INFORMATION: synthetic genetically encoded small illuminant
      (GESI) peptide substrate for protein kinase
<220> FEATURE:
<221> NAME/KEY: VARIANT
<222> LOCATION: (1)..(4)
<223> OTHER INFORMATION: Xaa = any amino acid
<220> FEATURE:
<221> NAME/KEY: VARIANT
<222> LOCATION: (5)..(9)
<223> OTHER INFORMATION: Xaa = any amino acid, may be present or absent
<220> FEATURE:
<221> NAME/KEY: PHOSPHORYLATION
<222> LOCATION: (10)..(10)
<223> OTHER INFORMATION: Thr can be phosphorylated
<220> FEATURE:
<221> NAME/KEY: VARIANT
<222> LOCATION: (12)..(12)
<223> OTHER INFORMATION: Xaa = any amino acid
<220> FEATURE:
<221> NAME/KEY: VARIANT
<222> LOCATION: (13)..(17)
<223> OTHER INFORMATION: Xaa = any amino acid, may be present or absent
<220> FEATURE:
<221> NAME/KEY: VARIANT
<222> LOCATION: (18)..(20)
<223> OTHER INFORMATION: Xaa = any amino acid

<400> SEQUENCE: 6

Xaa Xaa Xaa Xaa Xaa Xaa Xaa Xaa Xaa Thr Pro Xaa Xaa Xaa Xaa Xaa
1               5                   10                  15

Xaa Xaa Xaa Xaa
         20

<210> SEQ ID NO 7
<211> LENGTH: 21
<212> TYPE: PRT
<213> ORGANISM: Artificial Sequence
<220> FEATURE:
<223> OTHER INFORMATION: synthetic genetically encoded small illuminant
      (GESI) peptide substrate for histone modification enzyme
<220> FEATURE:
<221> NAME/KEY: MOD_RES
<222> LOCATION: (2)..(2)
<223> OTHER INFORMATION: Lys can be acetylated or methylated
<220> FEATURE:
<221> NAME/KEY: PHOSPHORYLATION
<222> LOCATION: (3)..(3)
<223> OTHER INFORMATION: Ser can be phosphorylated
<220> FEATURE:
<221> NAME/KEY: PHOSPHORYLATION
<222> LOCATION: (4)..(5)
<223> OTHER INFORMATION: Thr can be phosphorylated
<220> FEATURE:
<221> NAME/KEY: VARIANT
<222> LOCATION: (7)..(7)
<223> OTHER INFORMATION: Xaa = any amino acid
<220> FEATURE:
<221> NAME/KEY: VARIANT
<222> LOCATION: (8)..(16)
<223> OTHER INFORMATION: Xaa = any amino acid, may be present or absent
<220> FEATURE:
<221> NAME/KEY: MOD_RES
<222> LOCATION: (18)..(18)
<223> OTHER INFORMATION: Lys can be acetylated or methylated

<400> SEQUENCE: 7

Arg Lys Ser Thr Thr Gly Xaa Xaa Xaa Xaa Xaa Xaa Xaa Xaa Xaa Xaa
1               5                   10                  15

Gly Lys Ala Pro Arg
         20

<210> SEQ ID NO 8
<211> LENGTH: 18
<212> TYPE: PRT
<213> ORGANISM: Artificial Sequence
<220> FEATURE:
<223> OTHER INFORMATION: synthetic genetically encoded small illuminant
      (GESI) peptide substrate for histone modification enzyme
<220> FEATURE:
<221> NAME/KEY: VARIANT
<222> LOCATION: (1)..(1)
<223> OTHER INFORMATION: Xaa = any amino acid
<220> FEATURE:
<221> NAME/KEY: VARIANT
<222> LOCATION: (2)..(10)
<223> OTHER INFORMATION: Xaa = any amino acid, may be present or absent
<220> FEATURE:
<221> NAME/KEY: PHOSPHORYLATION
<222> LOCATION: (13)..(13)
<223> OTHER INFORMATION: Ser can be phosphorylated
<220> FEATURE:
<221> NAME/KEY: MOD_RES
<222> LOCATION: (14)..(14)
<223> OTHER INFORMATION: Lys can be acetylated or methylated
<220> FEATURE:
<221> NAME/KEY: PHOSPHORYLATION
<222> LOCATION: (16)..(16)
<223> OTHER INFORMATION: Thr can be phosphorylated

<400> SEQUENCE: 8

Xaa Xaa Xaa Xaa Xaa Xaa Xaa Xaa Xaa Xaa Ala Arg Thr Lys Gln Thr
1               5                   10                  15

Ala Arg

```
<210> SEQ ID NO 9
<211> LENGTH: 17
<212> TYPE: PRT
<213> ORGANISM: Artificial Sequence
<220> FEATURE:
<223> OTHER INFORMATION: synthetic genetically encoded small illuminant
      (GESI) peptide substrate for histone modification enzyme
<220> FEATURE:
<221> NAME/KEY: VARIANT
<222> LOCATION: (1)..(1)
<223> OTHER INFORMATION: Xaa = any amino acid
<220> FEATURE:
<221> NAME/KEY: VARIANT
<222> LOCATION: (2)..(10)
<223> OTHER INFORMATION: Xaa = any amino acid, may be present or absent
<220> FEATURE:
<221> NAME/KEY: PHOSPHORYLATION
<222> LOCATION: (11)..(11)
<223> OTHER INFORMATION: Ser can be phosphorylated
<220> FEATURE:
<221> NAME/KEY: MOD_RES
<222> LOCATION: (15)..(15)
<223> OTHER INFORMATION: Lys can be acetylated or methylated

<400> SEQUENCE: 9

Xaa Xaa Xaa Xaa Xaa Xaa Xaa Xaa Xaa Xaa Ser Gly Arg Gly Lys Gln
1               5                   10                  15

Gly

<210> SEQ ID NO 10
<211> LENGTH: 12
<212> TYPE: PRT
<213> ORGANISM: Artificial Sequence
<220> FEATURE:
<223> OTHER INFORMATION: synthetic genetically encoded small illuminant
      (GESI) peptide substrate for protein kinase
<220> FEATURE:
<221> NAME/KEY: VARIANT
<222> LOCATION: (2)..(11)
<223> OTHER INFORMATION: Xaa = any natural amino acid except Cys
<220> FEATURE:
<221> NAME/KEY: MOD_RES
<222> LOCATION: (12)..(12)
<223> OTHER INFORMATION: Glu affixed to polyethylene glycol grafted
      polystyrene bead

<400> SEQUENCE: 10

Asp Xaa Xaa Xaa Xaa Gly Xaa Xaa Xaa Xaa Xaa Glu
1               5                   10

<210> SEQ ID NO 11
<211> LENGTH: 7
<212> TYPE: PRT
<213> ORGANISM: Artificial Sequence
<220> FEATURE:
<223> OTHER INFORMATION: synthetic genetically encoded small illuminant
      (GESI) peptide of bead #1

<400> SEQUENCE: 11

Cys Asn Ser Pro Asp Ile Cys
1               5

<210> SEQ ID NO 12
<211> LENGTH: 7
<212> TYPE: PRT
<213> ORGANISM: Artificial Sequence
<220> FEATURE:
<223> OTHER INFORMATION: synthetic genetically encoded small illuminant
      (GESI) peptide of bead #3
```

```
<400> SEQUENCE: 12

Cys Gln Pro Asp Leu Thr Cys
1               5

<210> SEQ ID NO 13
<211> LENGTH: 7
<212> TYPE: PRT
<213> ORGANISM: Artificial Sequence
<220> FEATURE:
<223> OTHER INFORMATION: synthetic genetically encoded small illuminant
      (GESI) peptide of bead #6

<400> SEQUENCE: 13

Cys Gly Asn Thr Glu Pro Cys
1               5

<210> SEQ ID NO 14
<211> LENGTH: 7
<212> TYPE: PRT
<213> ORGANISM: Artificial Sequence
<220> FEATURE:
<223> OTHER INFORMATION: synthetic genetically encoded small illuminant
      (GESI) peptide of bead #8

<400> SEQUENCE: 14

Cys Met Thr Gln Glu Ala Cys
1               5

<210> SEQ ID NO 15
<211> LENGTH: 7
<212> TYPE: PRT
<213> ORGANISM: Artificial Sequence
<220> FEATURE:
<223> OTHER INFORMATION: synthetic genetically encoded small illuminant
      (GESI) peptide of bead #11

<400> SEQUENCE: 15

Cys Leu Ser Asp Glu Phe Cys
1               5

<210> SEQ ID NO 16
<211> LENGTH: 7
<212> TYPE: PRT
<213> ORGANISM: Artificial Sequence
<220> FEATURE:
<223> OTHER INFORMATION: synthetic genetically encoded small illuminant
      (GESI) peptide of bead #4

<400> SEQUENCE: 16

Cys His Thr His Ile Leu Cys
1               5

<210> SEQ ID NO 17
<211> LENGTH: 7
<212> TYPE: PRT
<213> ORGANISM: Artificial Sequence
<220> FEATURE:
<223> OTHER INFORMATION: synthetic genetically encoded small illuminant
      (GESI) peptide of bead #5

<400> SEQUENCE: 17

Cys His Pro Leu Leu Pro Cys
1               5

<210> SEQ ID NO 18
<211> LENGTH: 7
```

```
<212> TYPE: PRT
<213> ORGANISM: Artificial Sequence
<220> FEATURE:
<223> OTHER INFORMATION: synthetic genetically encoded small illuminant
      (GESI) peptide of bead #9

<400> SEQUENCE: 18

Cys Glu Ile His Arg Ile Cys
1               5

<210> SEQ ID NO 19
<211> LENGTH: 7
<212> TYPE: PRT
<213> ORGANISM: Artificial Sequence
<220> FEATURE:
<223> OTHER INFORMATION: synthetic genetically encoded small illuminant
      (GESI) peptide of bead #2

<400> SEQUENCE: 19

Cys Leu Met Asn Lys Trp Cys
1               5

<210> SEQ ID NO 20
<211> LENGTH: 7
<212> TYPE: PRT
<213> ORGANISM: Artificial Sequence
<220> FEATURE:
<223> OTHER INFORMATION: synthetic genetically encoded small illuminant
      (GESI) peptide of bead #7

<400> SEQUENCE: 20

Cys Tyr Lys Trp Trp Val Cys
1               5

<210> SEQ ID NO 21
<211> LENGTH: 7
<212> TYPE: PRT
<213> ORGANISM: Artificial Sequence
<220> FEATURE:
<223> OTHER INFORMATION: synthetic genetically encoded small illuminant
      (GESI) peptide of bead #10

<400> SEQUENCE: 21

Cys Lys Trp Ile Leu Pro Cys
1               5

<210> SEQ ID NO 22
<211> LENGTH: 12
<212> TYPE: PRT
<213> ORGANISM: Artificial Sequence
<220> FEATURE:
<223> OTHER INFORMATION: synthetic genetically encoded small illuminant
      (GESI) malachite green (MG) binding Peptide 1

<400> SEQUENCE: 22

Asp Ile Leu Asp Asp Gly Asp Glu Ile Gln Gly Glu
1               5                   10

<210> SEQ ID NO 23
<211> LENGTH: 12
<212> TYPE: PRT
<213> ORGANISM: Artificial Sequence
<220> FEATURE:
<223> OTHER INFORMATION: synthetic genetically encoded small illuminant
      (GESI) malachite green (MG) binding Peptide 2

<400> SEQUENCE: 23

Asp Trp Trp Trp Asp Gly Phe Glu Arg Leu Glu Glu
```

<210> SEQ ID NO 24
<211> LENGTH: 12
<212> TYPE: PRT
<213> ORGANISM: Artificial Sequence
<220> FEATURE:
<223> OTHER INFORMATION: synthetic genetically encoded small illuminant
      (GESI) malachite green (MG) binding Peptide 3

<400> SEQUENCE: 24

Asp Arg Asp Gly Asp Gly Asp His Arg Lys Ile Glu
1               5                   10

<210> SEQ ID NO 25
<211> LENGTH: 12
<212> TYPE: PRT
<213> ORGANISM: Artificial Sequence
<220> FEATURE:
<223> OTHER INFORMATION: synthetic genetically encoded small illuminant
      (GESI) malachite green (MG) binding Peptide 4

<400> SEQUENCE: 25

Asp Ser Asp Ser Trp Gly Glu Tyr Phe His Glu Glu
1               5                   10

<210> SEQ ID NO 26
<211> LENGTH: 12
<212> TYPE: PRT
<213> ORGANISM: Artificial Sequence
<220> FEATURE:
<223> OTHER INFORMATION: synthetic genetically encoded small illuminant
      (GESI) malachite green (MG) binding Peptide 5

<400> SEQUENCE: 26

Asp Phe Met Arg Gln Gly Val Tyr Asp Ile Pro Glu
1               5                   10

<210> SEQ ID NO 27
<211> LENGTH: 12
<212> TYPE: PRT
<213> ORGANISM: Artificial Sequence
<220> FEATURE:
<223> OTHER INFORMATION: synthetic genetically encoded small illuminant
      (GESI) malachite green (MG) binding Peptide 6

<400> SEQUENCE: 27

Asp Asp Tyr Asp Asp Gly Trp Ile Tyr Glu Phe Glu
1               5                   10

<210> SEQ ID NO 28
<211> LENGTH: 12
<212> TYPE: PRT
<213> ORGANISM: Artificial Sequence
<220> FEATURE:
<223> OTHER INFORMATION: synthetic genetically encoded small illuminant
      (GESI) malachite green (MG) binding Peptide 8

<400> SEQUENCE: 28

Asp Gly Asp Asp Gly Gly Tyr Trp Pro Phe Pro Glu
1               5                   10

<210> SEQ ID NO 29
<211> LENGTH: 12
<212> TYPE: PRT
<213> ORGANISM: Artificial Sequence
<220> FEATURE:
<223> OTHER INFORMATION: synthetic genetically encoded small illuminant (GESI) malachite green (MG) binding Peptide 10

<400> SEQUENCE: 29

Asp Glu Trp His Asp Gly Met Glu Gly Asn Leu Glu
1               5                   10

<210> SEQ ID NO 30
<211> LENGTH: 12
<212> TYPE: PRT
<213> ORGANISM: Artificial Sequence
<220> FEATURE:
<223> OTHER INFORMATION: synthetic genetically encoded small illuminant
      (GESI) malachite green (MG) binding Peptide 11

<400> SEQUENCE: 30

Asp Ser Lys Asp Pro Gly Met Thr His Leu Lys Glu
1               5                   10

<210> SEQ ID NO 31
<211> LENGTH: 12
<212> TYPE: PRT
<213> ORGANISM: Artificial Sequence
<220> FEATURE:
<223> OTHER INFORMATION: synthetic genetically encoded small illuminant
      (GESI) malachite green (MG) binding Peptide 12

<400> SEQUENCE: 31

Asp Trp Trp Asp Trp Gly Asn His Gly Tyr Thr Glu
1               5                   10

<210> SEQ ID NO 32
<211> LENGTH: 12
<212> TYPE: PRT
<213> ORGANISM: Artificial Sequence
<220> FEATURE:
<223> OTHER INFORMATION: synthetic genetically encoded small illuminant
      (GESI) malachite green (MG) binding Peptide 13

<400> SEQUENCE: 32

Asp Ala Gln Trp Met Gly Ala Asn Met His Thr Glu
1               5                   10

<210> SEQ ID NO 33
<211> LENGTH: 8
<212> TYPE: PRT
<213> ORGANISM: Artificial Sequence
<220> FEATURE:
<223> OTHER INFORMATION: synthetic amino acid linker

<400> SEQUENCE: 33

Gly Gly Ser Gly Ser Gly Gly Ser
1               5

<210> SEQ ID NO 34
<211> LENGTH: 12
<212> TYPE: PRT
<213> ORGANISM: Artificial Sequence
<220> FEATURE:
<223> OTHER INFORMATION: synthetic genetically encoded small illuminant
      (GESI) peptide insert for dORF2 gene of baculovirus transfer
      vector encoding Hepatitis E viral particles

<400> SEQUENCE: 34

Asp Ser Asp Ser Gln Gly Glu Tyr Phe His Glu Glu
1               5                   10

<210> SEQ ID NO 35

```
<211> LENGTH: 7
<212> TYPE: PRT
<213> ORGANISM: Artificial Sequence
<220> FEATURE:
<223> OTHER INFORMATION: synthetic peptide substrate for protein
      tyrosine kinases Btk, Etk and Src

<400> SEQUENCE: 35

Tyr Ile Tyr Gly Ser Phe Lys
1               5

<210> SEQ ID NO 36
<211> LENGTH: 14
<212> TYPE: PRT
<213> ORGANISM: Artificial Sequence
<220> FEATURE:
<223> OTHER INFORMATION: synthetic genetically encoded small illuminant
      (GESI) peptide of linear one-bead-one-compound (OBOC)
      combinatorial library L-1
<220> FEATURE:
<221> NAME/KEY: VARIANT
<222> LOCATION: (1)..(13)
<223> OTHER INFORMATION: Xaa = any natural amino acid except Cys
<220> FEATURE:
<221> NAME/KEY: PHOSPHORYLATION
<222> LOCATION: (5)..(5)
<223> OTHER INFORMATION: phosphorylated Tyr

<400> SEQUENCE: 36

Xaa Xaa Tyr Ile Tyr Gly Ser Phe Lys Xaa Xaa Xaa Xaa Cys
1               5                   10

<210> SEQ ID NO 37
<211> LENGTH: 15
<212> TYPE: PRT
<213> ORGANISM: Artificial Sequence
<220> FEATURE:
<223> OTHER INFORMATION: synthetic genetically encoded small illuminant
      (GESI) peptide of cyclic one-bead-one-compound (OBOC)
      combinatorial library L-2
<220> FEATURE:
<221> NAME/KEY: VARIANT
<222> LOCATION: (2)..(14)
<223> OTHER INFORMATION: Xaa = any natural amino acid except Cys
<220> FEATURE:
<221> NAME/KEY: PHOSPHORYLATION
<222> LOCATION: (6)..(6)
<223> OTHER INFORMATION: phosphorylated Tyr

<400> SEQUENCE: 37

Cys Xaa Xaa Tyr Ile Tyr Gly Ser Phe Lys Xaa Xaa Xaa Xaa Cys
1               5                   10                  15

<210> SEQ ID NO 38
<211> LENGTH: 7
<212> TYPE: PRT
<213> ORGANISM: Artificial Sequence
<220> FEATURE:
<223> OTHER INFORMATION: synthetic phosphorylated peptide substrate for
      protein tyrosine kinases Btk, Etk and Src
<220> FEATURE:
<221> NAME/KEY: PHOSPHORYLATION
<222> LOCATION: (3)..(3)
<223> OTHER INFORMATION: phosphorylated Tyr

<400> SEQUENCE: 38

Tyr Ile Tyr Gly Ser Phe Lys
1               5

<210> SEQ ID NO 39
<211> LENGTH: 14
```

```
<212> TYPE: PRT
<213> ORGANISM: Artificial Sequence
<220> FEATURE:
<223> OTHER INFORMATION: synthetic genetically encoded small illuminant
      (GESI) malachite green (MG) binding peptide 1 from linear library
      L-1
<220> FEATURE:
<221> NAME/KEY: PHOSPHORYLATION
<222> LOCATION: (5)..(5)
<223> OTHER INFORMATION: phosphorylated Tyr

<400> SEQUENCE: 39

Asp Asp Tyr Ile Tyr Gly Ser Phe Lys Pro Tyr Ile Ala Cys
1               5                   10

<210> SEQ ID NO 40
<211> LENGTH: 14
<212> TYPE: PRT
<213> ORGANISM: Artificial Sequence
<220> FEATURE:
<223> OTHER INFORMATION: synthetic genetically encoded small illuminant
      (GESI) malachite green (MG) binding peptide 2 from linear library
      L-1
<220> FEATURE:
<221> NAME/KEY: PHOSPHORYLATION
<222> LOCATION: (5)..(5)
<223> OTHER INFORMATION: phosphorylated Tyr

<400> SEQUENCE: 40

Asp Val Tyr Ile Tyr Gly Ser Phe Lys Asn Asp Tyr Ile Cys
1               5                   10

<210> SEQ ID NO 41
<211> LENGTH: 14
<212> TYPE: PRT
<213> ORGANISM: Artificial Sequence
<220> FEATURE:
<223> OTHER INFORMATION: synthetic genetically encoded small illuminant
      (GESI) malachite green (MG) binding peptide 3 from linear library
      L-1
<220> FEATURE:
<221> NAME/KEY: PHOSPHORYLATION
<222> LOCATION: (5)..(5)
<223> OTHER INFORMATION: phosphorylated Tyr

<400> SEQUENCE: 41

Asp Asn Tyr Ile Tyr Gly Ser Phe Lys Pro Trp Glu Trp Cys
1               5                   10

<210> SEQ ID NO 42
<211> LENGTH: 14
<212> TYPE: PRT
<213> ORGANISM: Artificial Sequence
<220> FEATURE:
<223> OTHER INFORMATION: synthetic genetically encoded small illuminant
      (GESI) malachite green (MG) binding peptide 4 from linear library
      L-1
<220> FEATURE:
<221> NAME/KEY: PHOSPHORYLATION
<222> LOCATION: (5)..(5)
<223> OTHER INFORMATION: phosphorylated Tyr

<400> SEQUENCE: 42

Asp Val Tyr Ile Tyr Gly Ser Phe Lys Tyr Trp Pro Ala Cys
1               5                   10

<210> SEQ ID NO 43
<211> LENGTH: 14
<212> TYPE: PRT
<213> ORGANISM: Artificial Sequence
<220> FEATURE:
```

<223> OTHER INFORMATION: synthetic genetically encoded small illuminant
      (GESI) malachite green (MG) binding peptide 5 from linear library
      L-1
<220> FEATURE:
<221> NAME/KEY: PHOSPHORYLATION
<222> LOCATION: (5)..(5)
<223> OTHER INFORMATION: phosphorylated Tyr

<400> SEQUENCE: 43

Asp Thr Tyr Ile Tyr Gly Ser Phe Lys Val Asn Pro Asp Cys
1               5                   10

<210> SEQ ID NO 44
<211> LENGTH: 4
<212> TYPE: PRT
<213> ORGANISM: Artificial Sequence
<220> FEATURE:
<223> OTHER INFORMATION: synthetic phosphorylated peptide substrate for
      protein tyrosine kinases Btk, Etk and Src and protein kinase A
      (PKA)
<220> FEATURE:
<221> NAME/KEY: VARIANT
<222> LOCATION: (3)..(3)
<223> OTHER INFORMATION: Xaa = any amino acid
<220> FEATURE:
<221> NAME/KEY: PHOSPHORYLATION
<222> LOCATION: (4)..(4)
<223> OTHER INFORMATION: phosphorylated Ser

<400> SEQUENCE: 44

Arg Arg Xaa Ser
1

<210> SEQ ID NO 45
<211> LENGTH: 12
<212> TYPE: PRT
<213> ORGANISM: Artificial Sequence
<220> FEATURE:
<223> OTHER INFORMATION: synthetic genetically encoded small illuminant
      (GESI) malachite green (MG) binding peptide from cyclic library
      L-4
<220> FEATURE:
<221> NAME/KEY: PHOSPHORYLATION
<222> LOCATION: (7)..(7)
<223> OTHER INFORMATION: phosphorylated Ser

<400> SEQUENCE: 45

Cys Met Gly Arg Arg Pro Ser Val Asp Asn Asn Cys
1               5                   10

<210> SEQ ID NO 46
<211> LENGTH: 12
<212> TYPE: PRT
<213> ORGANISM: Artificial Sequence
<220> FEATURE:
<223> OTHER INFORMATION: synthetic genetically encoded small illuminant
      (GESI) malachite green (MG) binding peptide from cyclic library
      L-4
<220> FEATURE:
<221> NAME/KEY: PHOSPHORYLATION
<222> LOCATION: (7)..(7)
<223> OTHER INFORMATION: phosphorylated Ser

<400> SEQUENCE: 46

Cys Gly Val Arg Arg Asp Ser Trp Trp Tyr Asp Cys
1               5                   10

<210> SEQ ID NO 47
<211> LENGTH: 14
<212> TYPE: PRT
<213> ORGANISM: Artificial Sequence -continued

```
<220> FEATURE:
<223> OTHER INFORMATION: synthetic genetically encoded small illuminant
      (GESI) malachite green (MG) binding peptide 1 from linear library
      L-1
<220> FEATURE:
<221> NAME/KEY: PHOSPHORYLATION
<222> LOCATION: (5)..(5)
<223> OTHER INFORMATION: phosphorylated Tyr

<400> SEQUENCE: 47

Asp Asp Tyr Ile Tyr Gly Ser Phe Lys Pro Tyr Ile Ala Cys
1               5                   10

<210> SEQ ID NO 48
<211> LENGTH: 14
<212> TYPE: PRT
<213> ORGANISM: Artificial Sequence
<220> FEATURE:
<223> OTHER INFORMATION: synthetic genetically encoded small illuminant
      (GESI) malachite green (MG) binding peptide 2 from linear library
      L-1
<220> FEATURE:
<221> NAME/KEY: PHOSPHORYLATION
<222> LOCATION: (5)..(5)
<223> OTHER INFORMATION: phosphorylated Tyr

<400> SEQUENCE: 48

Asp Val Tyr Ile Tyr Gly Ser Phe Lys Asn Asp Tyr Ile Cys
1               5                   10

<210> SEQ ID NO 49
<211> LENGTH: 14
<212> TYPE: PRT
<213> ORGANISM: Artificial Sequence
<220> FEATURE:
<223> OTHER INFORMATION: synthetic genetically encoded small illuminant
      (GESI) malachite green (MG) binding peptide 3 from linear library
      L-1
<220> FEATURE:
<221> NAME/KEY: PHOSPHORYLATION
<222> LOCATION: (5)..(5)
<223> OTHER INFORMATION: phosphorylated Tyr

<400> SEQUENCE: 49

Asp Asn Tyr Ile Tyr Gly Ser Phe Lys Pro Trp Glu Trp Cys
1               5                   10

<210> SEQ ID NO 50
<211> LENGTH: 14
<212> TYPE: PRT
<213> ORGANISM: Artificial Sequence
<220> FEATURE:
<223> OTHER INFORMATION: synthetic genetically encoded small illuminant
      (GESI) malachite green (MG) binding peptide 4 from linear library
      L-1
<220> FEATURE:
<221> NAME/KEY: PHOSPHORYLATION
<222> LOCATION: (5)..(5)
<223> OTHER INFORMATION: phosphorylated Tyr

<400> SEQUENCE: 50

Asp Val Tyr Ile Tyr Gly Ser Phe Lys Tyr Trp Pro Ala Cys
1               5                   10

<210> SEQ ID NO 51
<211> LENGTH: 14
<212> TYPE: PRT
<213> ORGANISM: Artificial Sequence
<220> FEATURE:
<223> OTHER INFORMATION: synthetic genetically encoded small illuminant
      (GESI) malachite green (MG) binding peptide 5 from linear library
```

```
        L-1
<220> FEATURE:
<221> NAME/KEY: PHOSPHORYLATION
<222> LOCATION: (5)..(5)
<223> OTHER INFORMATION: phosphorylated Ser

<400> SEQUENCE: 51

Asp Thr Tyr Ile Tyr Gly Ser Phe Lys Val Asn Pro Asp Cys
1               5                   10

<210> SEQ ID NO 52
<211> LENGTH: 13
<212> TYPE: PRT
<213> ORGANISM: Artificial Sequence
<220> FEATURE:
<223> OTHER INFORMATION: synthetic genetically encoded small illuminant
      (GESI) peptide 1-D from linear library L-1
<220> FEATURE:
<221> NAME/KEY: PHOSPHORYLATION
<222> LOCATION: (4)..(4)
<223> OTHER INFORMATION: phosphorylated Tyr

<400> SEQUENCE: 52

Asp Tyr Ile Tyr Gly Ser Phe Lys Pro Tyr Ile Ala Cys
1               5                   10

<210> SEQ ID NO 53
<211> LENGTH: 13
<212> TYPE: PRT
<213> ORGANISM: Artificial Sequence
<220> FEATURE:
<223> OTHER INFORMATION: synthetic genetically encoded small illuminant
      (GESI) peptide 2-D from linear library L-1
<220> FEATURE:
<221> NAME/KEY: PHOSPHORYLATION
<222> LOCATION: (4)..(4)
<223> OTHER INFORMATION: phosphorylated Tyr

<400> SEQUENCE: 53

Val Tyr Ile Tyr Gly Ser Phe Lys Asn Asp Tyr Ile Cys
1               5                   10

<210> SEQ ID NO 54
<211> LENGTH: 13
<212> TYPE: PRT
<213> ORGANISM: Artificial Sequence
<220> FEATURE:
<223> OTHER INFORMATION: synthetic genetically encoded small illuminant
      (GESI) peptide 3-D from linear library L-1
<220> FEATURE:
<221> NAME/KEY: PHOSPHORYLATION
<222> LOCATION: (4)..(4)
<223> OTHER INFORMATION: phosphorylated Tyr

<400> SEQUENCE: 54

Asn Tyr Ile Tyr Gly Ser Phe Lys Pro Trp Glu Trp Cys
1               5                   10

<210> SEQ ID NO 55
<211> LENGTH: 13
<212> TYPE: PRT
<213> ORGANISM: Artificial Sequence
<220> FEATURE:
<223> OTHER INFORMATION: synthetic genetically encoded small illuminant
      (GESI) peptide 4-D from linear library L-1
<220> FEATURE:
<221> NAME/KEY: PHOSPHORYLATION
<222> LOCATION: (4)..(4)
<223> OTHER INFORMATION: phosphorylated Tyr

<400> SEQUENCE: 55
```

```
Val Tyr Ile Tyr Gly Ser Phe Lys Tyr Trp Pro Ala Cys
1               5                   10
```

<210> SEQ ID NO 56
<211> LENGTH: 13
<212> TYPE: PRT
<213> ORGANISM: Artificial Sequence
<220> FEATURE:
<223> OTHER INFORMATION: synthetic genetically encoded small illuminant
      (GESI) peptide 5-D from linear library L-1
<220> FEATURE:
<221> NAME/KEY: PHOSPHORYLATION
<222> LOCATION: (4)..(4)
<223> OTHER INFORMATION: phosphorylated Tyr

<400> SEQUENCE: 56

```
Thr Tyr Ile Tyr Gly Ser Phe Lys Val Asn Pro Asp Cys
1               5                   10
```

<210> SEQ ID NO 57
<211> LENGTH: 14
<212> TYPE: PRT
<213> ORGANISM: Artificial Sequence
<220> FEATURE:
<223> OTHER INFORMATION: synthetic genetically encoded small illuminant
      (GESI) peptide 1-P from linear library L-1

<400> SEQUENCE: 57

```
Asp Asp Tyr Ile Tyr Gly Ser Phe Lys Pro Tyr Ile Ala Cys
1               5                   10
```

<210> SEQ ID NO 58
<211> LENGTH: 14
<212> TYPE: PRT
<213> ORGANISM: Artificial Sequence
<220> FEATURE:
<223> OTHER INFORMATION: synthetic genetically encoded small illuminant
      (GESI) malachite green (MG) binding peptide 2-P from linear
      library L-1

<400> SEQUENCE: 58

```
Asp Val Tyr Ile Tyr Gly Ser Phe Lys Asn Asp Tyr Ile Cys
1               5                   10
```

<210> SEQ ID NO 59
<211> LENGTH: 14
<212> TYPE: PRT
<213> ORGANISM: Artificial Sequence
<220> FEATURE:
<223> OTHER INFORMATION: synthetic genetically encoded small illuminant
      (GESI) malachite green (MG) binding peptide 3-P from linear
      library L-1

<400> SEQUENCE: 59

```
Asp Asn Tyr Ile Tyr Gly Ser Phe Lys Pro Trp Glu Trp Cys
1               5                   10
```

<210> SEQ ID NO 60
<211> LENGTH: 14
<212> TYPE: PRT
<213> ORGANISM: Artificial Sequence
<220> FEATURE:
<223> OTHER INFORMATION: synthetic genetically encoded small illuminant
      (GESI) peptide 4-P from linear library L-1

<400> SEQUENCE: 60

```
Asp Val Tyr Ile Tyr Gly Ser Phe Lys Tyr Trp Pro Ala Cys
1               5                   10
```

<210> SEQ ID NO 61
<211> LENGTH: 14
<212> TYPE: PRT
<213> ORGANISM: Artificial Sequence
<220> FEATURE:
<223> OTHER INFORMATION: synthetic genetically encoded small illuminant
      (GESI) peptide 5-P from linear library L-1

<400> SEQUENCE: 61

Asp Thr Tyr Ile Tyr Gly Ser Phe Lys Val Asn Pro Asp Cys
1               5                   10

<210> SEQ ID NO 62
<211> LENGTH: 15
<212> TYPE: PRT
<213> ORGANISM: Artificial Sequence
<220> FEATURE:
<223> OTHER INFORMATION: synthetic genetically encoded small illuminant
      (GESI) malachite green (MG) binding peptide 1C from linear library
      L-1
<220> FEATURE:
<221> NAME/KEY: PHOSPHORYLATION
<222> LOCATION: (6)..(6)
<223> OTHER INFORMATION: phosphorylated Tyr

<400> SEQUENCE: 62

Cys Asp Asp Tyr Ile Tyr Gly Ser Phe Lys Pro Tyr Ile Ala Cys
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: synthetic genetically encoded small illuminant
      (GESI) malachite green (MG) binding peptide 2C from linear library
      L-1
<220> FEATURE:
<221> NAME/KEY: PHOSPHORYLATION
<222> LOCATION: (6)..(6)
<223> OTHER INFORMATION: phosphorylated Tyr

<400> SEQUENCE: 63

Cys Asp Val Tyr Ile Tyr Gly Ser Phe Lys Asn Asp Tyr Ile Cys
1               5                   10                  15

<210> SEQ ID NO 64
<211> LENGTH: 16
<212> TYPE: PRT
<213> ORGANISM: Artificial Sequence
<220> FEATURE:
<223> OTHER INFORMATION: synthetic genetically encoded small illuminant
      (GESI) malachite green (MG) binding peptide 3C from linear library
      L-1
<220> FEATURE:
<221> NAME/KEY: PHOSPHORYLATION
<222> LOCATION: (6)..(6)
<223> OTHER INFORMATION: phosphorylated Tyr

<400> SEQUENCE: 64

Cys Asp Asn Tyr Ile Tyr Gly Ser Phe Lys Asn Pro Trp Glu Trp Cys
1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: synthetic genetically encoded small illuminant

```
         (GESI) malachite green (MG) binding peptide 4C from linear library
         L-1
<220> FEATURE:
<221> NAME/KEY: PHOSPHORYLATION
<222> LOCATION: (6)..(6)
<223> OTHER INFORMATION: phosphorylated Tyr

<400> SEQUENCE: 65

Cys Asp Val Tyr Ile Tyr Gly Ser Phe Lys Tyr Trp Pro Ala Cys
1               5                   10                  15

<210> SEQ ID NO 66
<211> LENGTH: 15
<212> TYPE: PRT
<213> ORGANISM: Artificial Sequence
<220> FEATURE:
<223> OTHER INFORMATION: synthetic genetically encoded small illuminant
         (GESI) malachite green (MG) binding peptide 5C from linear library
         L-1
<220> FEATURE:
<221> NAME/KEY: PHOSPHORYLATION
<222> LOCATION: (6)..(6)
<223> OTHER INFORMATION: phosphorylated Tyr

<400> SEQUENCE: 66

Cys Asp Thr Tyr Ile Tyr Gly Ser Phe Lys Val Asn Pro Asp Cys
1               5                   10                  15

<210> SEQ ID NO 67
<211> LENGTH: 10
<212> TYPE: PRT
<213> ORGANISM: Artificial Sequence
<220> FEATURE:
<223> OTHER INFORMATION: synthetic genetically encoded small illuminant
         (GESI) peptide with N-terminal 6 amino acids of histone H3
<220> FEATURE:
<221> NAME/KEY: VARIANT
<222> LOCATION: (1)..(4)
<223> OTHER INFORMATION: Xaa = any amino acid
<220> FEATURE:
<221> NAME/KEY: PHOSPHORYLATION
<222> LOCATION: (7)..(7)
<223> OTHER INFORMATION: phosphphorylated Thr
<220> FEATURE:
<221> NAME/KEY: METHYLATION
<222> LOCATION: (8)..(8)
<223> OTHER INFORMATION: Lys unmethylated or methylated 1-3 times

<400> SEQUENCE: 67

Xaa Xaa Xaa Xaa Ala Arg Thr Lys Gln Thr
1               5                   10

<210> SEQ ID NO 68
<211> LENGTH: 11
<212> TYPE: PRT
<213> ORGANISM: Artificial Sequence
<220> FEATURE:
<223> OTHER INFORMATION: synthetic genetically encoded small illuminant
         (GESI) peptide with N-terminal histone H2 tail
<220> FEATURE:
<221> NAME/KEY: PHOSPHORYLATION
<222> LOCATION: (7)..(7)
<223> OTHER INFORMATION: phophorylated Ser
<220> FEATURE:
<221> NAME/KEY: ACETYLATION
<222> LOCATION: (11)..(11)
<223> OTHER INFORMATION: acetylated Lys

<400> SEQUENCE: 68

Asp Pro Ser Trp Pro Asn Ser Gly Arg Gly Lys
1               5                   10
```

<210> SEQ ID NO 69
<211> LENGTH: 11
<212> TYPE: PRT
<213> ORGANISM: Artificial Sequence
<220> FEATURE:
<223> OTHER INFORMATION: synthetic genetically encoded small illuminant
    (GESI) peptide with N-terminal histone H2 tail
<220> FEATURE:
<221> NAME/KEY: PHOSPHORYLATION
<222> LOCATION: (7)..(7)
<223> OTHER INFORMATION: phosphorylated Ser
<220> FEATURE:
<221> NAME/KEY: ACETYLATION
<222> LOCATION: (11)..(11)
<223> OTHER INFORMATION: acetylated Lys

<400> SEQUENCE: 69

Thr Arg Pro Ser Met Trp Ser Gly Arg Gly Lys
1               5                   10

<210> SEQ ID NO 70
<211> LENGTH: 11
<212> TYPE: PRT
<213> ORGANISM: Artificial Sequence
<220> FEATURE:
<223> OTHER INFORMATION: synthetic genetically encoded small illuminant
    (GESI) peptide with N-terminal histone H2 tail
<220> FEATURE:
<221> NAME/KEY: PHOSPHORYLATION
<222> LOCATION: (7)..(7)
<223> OTHER INFORMATION: phosphorylated Ser
<220> FEATURE:
<221> NAME/KEY: ACETYLATION
<222> LOCATION: (11)..(11)
<223> OTHER INFORMATION: acetylated Lys

<400> SEQUENCE: 70

Val Trp Asp Gly Ile Arg Ser Gly Arg Gly Lys
1               5                   10

<210> SEQ ID NO 71
<211> LENGTH: 11
<212> TYPE: PRT
<213> ORGANISM: Artificial Sequence
<220> FEATURE:
<223> OTHER INFORMATION: synthetic genetically encoded small illuminant
    (GESI) peptide substrate for protein kinase
<220> FEATURE:
<221> NAME/KEY: PHOSPHORYLATION
<222> LOCATION: (7)..(7)
<223> OTHER INFORMATION: phosphorylated Ser

<400> SEQUENCE: 71

Gly Leu Phe Asp Gln Glu Ser Gly Arg Gly Lys
1               5                   10

<210> SEQ ID NO 72
<211> LENGTH: 9
<212> TYPE: PRT
<213> ORGANISM: Artificial Sequence
<220> FEATURE:
<223> OTHER INFORMATION: synthetic genetically encoded small illuminant
    (GESI) peptide for protein kinase A (PKA)
<220> FEATURE:
<221> NAME/KEY: MOD_RES
<222> LOCATION: (1)..(9)
<223> OTHER INFORMATION: Xaa = any amino acid

<400> SEQUENCE: 72

Xaa Xaa Xaa Arg Arg Xaa Ser Xaa Xaa
1               5

```
<210> SEQ ID NO 73
<211> LENGTH: 10
<212> TYPE: PRT
<213> ORGANISM: Artificial Sequence
<220> FEATURE:
<223> OTHER INFORMATION: synthetic genetically encoded small illuminant
      (GESI) peptide for protein kinase JNK
<220> FEATURE:
<221> NAME/KEY: VARIANT
<222> LOCATION: (1)..(10)
<223> OTHER INFORMATION: Xaa = any amino acid

<400> SEQUENCE: 73

Xaa Xaa Xaa Xaa Xaa Thr Pro Xaa Xaa Xaa
1               5                  10

<210> SEQ ID NO 74
<211> LENGTH: 12
<212> TYPE: PRT
<213> ORGANISM: Artificial Sequence
<220> FEATURE:
<223> OTHER INFORMATION: synthetic genetically encoded small illuminant
      (GESI) peptide linear library
<220> FEATURE:
<221> NAME/KEY: VARIANT
<222> LOCATION: (2)..(11)
<223> OTHER INFORMATION: Xaa = any amino acid

<400> SEQUENCE: 74

Asp Xaa Xaa Xaa Xaa Gly Xaa Xaa Xaa Xaa Xaa Glu
1               5                  10

<210> SEQ ID NO 75
<211> LENGTH: 17
<212> TYPE: PRT
<213> ORGANISM: Artificial Sequence
<220> FEATURE:
<223> OTHER INFORMATION: synthetic genetically encoded small illuminant
      (GESI) peptide histone H2 peptide fusion library
<220> FEATURE:
<221> NAME/KEY: VARIANT
<222> LOCATION: (1)..(1)
<223> OTHER INFORMATION: Xaa = any natural amino acid except Cys
<220> FEATURE:
<221> NAME/KEY: VARIANT
<222> LOCATION: (2)..(8)
<223> OTHER INFORMATION: Xaa = any amino acid
<220> FEATURE:
<221> NAME/KEY: VARIANT
<222> LOCATION: (9)..(10)
<223> OTHER INFORMATION: Xaa = any natural amino acid except Cys, may be
      present or absent
<220> FEATURE:
<221> NAME/KEY: PHOSPHORYLATION
<222> LOCATION: (11)..(11)
<223> OTHER INFORMATION: Ser can be phosphorylated or unphosphorylated
<220> FEATURE:
<221> NAME/KEY: ACETYLATION
<222> LOCATION: (15)..(15)
<223> OTHER INFORMATION: Lys can be acetylated

<400> SEQUENCE: 75

Xaa Xaa Xaa Xaa Xaa Xaa Xaa Xaa Xaa Xaa Ser Gly Arg Gly Lys Gln
1               5                  10                  15

Gly

<210> SEQ ID NO 76
<211> LENGTH: 21
<212> TYPE: PRT
<213> ORGANISM: Artificial Sequence
```

```
<220> FEATURE:
<223> OTHER INFORMATION: synthetic genetically encoded small illuminant
      (GESI) peptide histone H3 peptide fusion library
<220> FEATURE:
<221> NAME/KEY: METHYLATION
<222> LOCATION: (2)..(2)
<223> OTHER INFORMATION: Arg can be methylated
<220> FEATURE:
<221> NAME/KEY: PHOSPHORYLATION
<222> LOCATION: (3)..(3)
<223> OTHER INFORMATION: Thr can be phosphorylated
<220> FEATURE:
<221> NAME/KEY: MOD_RES
<222> LOCATION: (4)..(4)
<223> OTHER INFORMATION: Lys can be methylated or acetylated
<220> FEATURE:
<221> NAME/KEY: MOD_RES
<222> LOCATION: (9)..(9)
<223> OTHER INFORMATION: Lys can be methylated or acetylated
<220> FEATURE:
<221> NAME/KEY: PHOSPHORYLATION
<222> LOCATION: (10)..(10)
<223> OTHER INFORMATION: Ser can be phosphorylated
<220> FEATURE:
<221> NAME/KEY: PHOSPHORYLATION
<222> LOCATION: (11)..(11)
<223> OTHER INFORMATION: Thr can be phosphorylated
<220> FEATURE:
<221> NAME/KEY: ACETYLATION
<222> LOCATION: (14)..(14)
<223> OTHER INFORMATION: Lys may be acetuylated
<220> FEATURE:
<221> NAME/KEY: METHYLATION
<222> LOCATION: (17)..(17)
<223> OTHER INFORMATION: Arg can be methylated
<220> FEATURE:
<221> NAME/KEY: MOD_RES
<222> LOCATION: (18)..(18)
<223> OTHER INFORMATION: Lys can be methylated or acetylated

<400> SEQUENCE: 76

Ala Arg Thr Lys Gln Thr Ala Arg Lys Ser Thr Gly Gly Lys Ala Pro
1               5                   10                  15

Arg Lys Gln Leu Ala
            20

<210> SEQ ID NO 77
<211> LENGTH: 21
<212> TYPE: PRT
<213> ORGANISM: Artificial Sequence
<220> FEATURE:
<223> OTHER INFORMATION: synthetic genetically encoded small illuminant
      (GESI) peptide histone H3 peptide fusion Library 1
<220> FEATURE:
<221> NAME/KEY: METHYLATION
<222> LOCATION: (2)..(2)
<223> OTHER INFORMATION: Lys unmethylated or methylated 1-3 times
<220> FEATURE:
<221> NAME/KEY: PHOSPHORYLATION
<222> LOCATION: (3)..(3)
<223> OTHER INFORMATION: Ser can be phosphorylated or unphosphorylated
<220> FEATURE:
<221> NAME/KEY: PHOSPHORYLATION
<222> LOCATION: (4)..(4)
<223> OTHER INFORMATION: Thr can be phosphorylated or unphosphorylated
<220> FEATURE:
<221> NAME/KEY: VARIANT
<222> LOCATION: (7)..(7)
<223> OTHER INFORMATION: Xaa = any natural amino acid except Cys
<220> FEATURE:
<221> NAME/KEY: VARIANT
<222> LOCATION: (8)..(16)
<223> OTHER INFORMATION: Xaa = any natural amino acid except Cys, may be
      present or absent
<220> FEATURE:
<221> NAME/KEY: METHYLATION
```

```
<222> LOCATION: (18)..(18)
<223> OTHER INFORMATION: Lys unmethylated or methylated 1-3 times

<400> SEQUENCE: 77

Arg Lys Ser Thr Thr Gly Xaa Xaa Xaa Xaa Xaa Xaa Xaa Xaa Xaa Xaa
1               5                   10                  15

Gly Lys Ala Pro Arg
            20

<210> SEQ ID NO 78
<211> LENGTH: 18
<212> TYPE: PRT
<213> ORGANISM: Artificial Sequence
<220> FEATURE:
<223> OTHER INFORMATION: synthetic genetically encoded small illuminant
      (GESI) peptide histone H3 peptide fusion Library 2
<220> FEATURE:
<221> NAME/KEY: VARIANT
<222> LOCATION: (1)..(1)
<223> OTHER INFORMATION: Xaa = any natural amino acid except Cys
<220> FEATURE:
<221> NAME/KEY: VARIANT
<222> LOCATION: (2)..(10)
<223> OTHER INFORMATION: Xaa = any natural amino acid except Cys, may be
      present or absent
<220> FEATURE:
<221> NAME/KEY: PHOSPHORYLATION
<222> LOCATION: (13)..(13)
<223> OTHER INFORMATION: Thr can be phosphorylated or unphosphorylated
<220> FEATURE:
<221> NAME/KEY: METHYLATION
<222> LOCATION: (14)..(14)
<223> OTHER INFORMATION: Lys unmethylated or methylated 1-3 times

<400> SEQUENCE: 78

Xaa Xaa Xaa Xaa Xaa Xaa Xaa Xaa Xaa Xaa Ala Arg Thr Lys Gln Thr
1               5                   10                  15

Ala Arg

<210> SEQ ID NO 79
<211> LENGTH: 12
<212> TYPE: PRT
<213> ORGANISM: Artificial Sequence
<220> FEATURE:
<223> OTHER INFORMATION: synthetic genetically encoded small illuminant
      (GESI) malachite green (MG) binding Peptide 12

<400> SEQUENCE: 79

Asp Trp Trp Asp Trp Gly Asn His Gly Tyr Thr Glu
1               5                   10

<210> SEQ ID NO 80
<211> LENGTH: 12
<212> TYPE: PRT
<213> ORGANISM: Artificial Sequence
<220> FEATURE:
<223> OTHER INFORMATION: synthetic genetically encoded small illuminant
      (GESI) Peptide 12 variant from alanine walk

<400> SEQUENCE: 80

Asp Trp Trp Asp Trp Gly Asn His Gly Tyr Thr Ala
1               5                   10

<210> SEQ ID NO 81
<211> LENGTH: 12
<212> TYPE: PRT
<213> ORGANISM: Artificial Sequence
<220> FEATURE:
<223> OTHER INFORMATION: synthetic genetically encoded small illuminant
```

(GESI) Peptide 12 variant from alanine walk

<400> SEQUENCE: 81

Asp Trp Trp Asp Trp Gly Asn His Gly Tyr Ala Glu
1               5                   10

<210> SEQ ID NO 82
<211> LENGTH: 12
<212> TYPE: PRT
<213> ORGANISM: Artificial Sequence
<220> FEATURE:
<223> OTHER INFORMATION: synthetic genetically encoded small illuminant
      (GESI) Peptide 12 variant from alanine walk

<400> SEQUENCE: 82

Asp Trp Trp Asp Trp Gly Asn His Gly Ala Thr Glu
1               5                   10

<210> SEQ ID NO 83
<211> LENGTH: 12
<212> TYPE: PRT
<213> ORGANISM: Artificial Sequence
<220> FEATURE:
<223> OTHER INFORMATION: synthetic genetically encoded small illuminant
      (GESI) Peptide 12 variant from alanine walk

<400> SEQUENCE: 83

Asp Trp Trp Asp Trp Gly Asn His Ala Tyr Thr Glu
1               5                   10

<210> SEQ ID NO 84
<211> LENGTH: 12
<212> TYPE: PRT
<213> ORGANISM: Artificial Sequence
<220> FEATURE:
<223> OTHER INFORMATION: synthetic genetically encoded small illuminant
      (GESI) Peptide 12 variant from alanine walk

<400> SEQUENCE: 84

Asp Trp Trp Asp Trp Gly Asn Ala Gly Tyr Thr Glu
1               5                   10

<210> SEQ ID NO 85
<211> LENGTH: 12
<212> TYPE: PRT
<213> ORGANISM: Artificial Sequence
<220> FEATURE:
<223> OTHER INFORMATION: synthetic genetically encoded small illuminant
      (GESI) Peptide 12 variant from alanine walk

<400> SEQUENCE: 85

Asp Trp Trp Asp Trp Gly Ala His Gly Tyr Thr Glu
1               5                   10

<210> SEQ ID NO 86
<211> LENGTH: 12
<212> TYPE: PRT
<213> ORGANISM: Artificial Sequence
<220> FEATURE:
<223> OTHER INFORMATION: synthetic genetically encoded small illuminant
      (GESI) Peptide 12 variant from alanine walk

<400> SEQUENCE: 86

Asp Trp Trp Asp Trp Ala Asn His Gly Tyr Thr Glu
1               5                   10

<210> SEQ ID NO 87

```
<211> LENGTH: 12
<212> TYPE: PRT
<213> ORGANISM: Artificial Sequence
<220> FEATURE:
<223> OTHER INFORMATION: synthetic genetically encoded small illuminant
      (GESI) Peptide 12 variant from alanine walk

<400> SEQUENCE: 87

Asp Trp Trp Asp Ala Gly Asn His Gly Tyr Thr Glu
1               5                   10

<210> SEQ ID NO 88
<211> LENGTH: 12
<212> TYPE: PRT
<213> ORGANISM: Artificial Sequence
<220> FEATURE:
<223> OTHER INFORMATION: synthetic genetically encoded small illuminant
      (GESI) Peptide 12 variant from alanine walk

<400> SEQUENCE: 88

Asp Trp Trp Ala Trp Gly Asn His Gly Tyr Thr Glu
1               5                   10

<210> SEQ ID NO 89
<211> LENGTH: 12
<212> TYPE: PRT
<213> ORGANISM: Artificial Sequence
<220> FEATURE:
<223> OTHER INFORMATION: synthetic genetically encoded small illuminant
      (GESI) Peptide 12 variant from alanine walk

<400> SEQUENCE: 89

Asp Trp Ala Asp Trp Gly Asn His Gly Tyr Thr Glu
1               5                   10

<210> SEQ ID NO 90
<211> LENGTH: 12
<212> TYPE: PRT
<213> ORGANISM: Artificial Sequence
<220> FEATURE:
<223> OTHER INFORMATION: synthetic genetically encoded small illuminant
      (GESI) Peptide 12 variant from alanine walk

<400> SEQUENCE: 90

Asp Ala Trp Asp Trp Gly Asn His Gly Tyr Thr Glu
1               5                   10

<210> SEQ ID NO 91
<211> LENGTH: 12
<212> TYPE: PRT
<213> ORGANISM: Artificial Sequence
<220> FEATURE:
<223> OTHER INFORMATION: synthetic genetically encoded small illuminant
      (GESI) Peptide 12 variant from alanine walk

<400> SEQUENCE: 91

Ala Trp Trp Asp Trp Gly Asn His Gly Tyr Thr Glu
1               5                   10

<210> SEQ ID NO 92
<211> LENGTH: 11
<212> TYPE: PRT
<213> ORGANISM: Artificial Sequence
<220> FEATURE:
<223> OTHER INFORMATION: synthetic genetically encoded small illuminant
      (GESI) Peptide 12 variant from alanine walk, Peptide 12 deletion

<400> SEQUENCE: 92
```

Trp Trp Asp Trp Gly Asn His Gly Tyr Thr Glu
1               5                   10

<210> SEQ ID NO 93
<211> LENGTH: 10
<212> TYPE: PRT
<213> ORGANISM: Artificial Sequence
<220> FEATURE:
<223> OTHER INFORMATION: synthetic genetically encoded small illuminant
      (GESI) Peptide 12 variant from alanine walk, Peptide 12 deletion

<400> SEQUENCE: 93

Trp Asp Trp Gly Asn His Gly Tyr Thr Glu
1               5                   10

<210> SEQ ID NO 94
<211> LENGTH: 9
<212> TYPE: PRT
<213> ORGANISM: Artificial Sequence
<220> FEATURE:
<223> OTHER INFORMATION: synthetic genetically encoded small illuminant
      (GESI) Peptide 12 variant from alanine walk, Peptide 12 deletion

<400> SEQUENCE: 94

Asp Trp Gly Asn His Gly Tyr Thr Glu
1               5

<210> SEQ ID NO 95
<211> LENGTH: 8
<212> TYPE: PRT
<213> ORGANISM: Artificial Sequence
<220> FEATURE:
<223> OTHER INFORMATION: synthetic genetically encoded small illuminant
      (GESI) Peptide 12 variant from alanine walk, Peptide 12 deletion

<400> SEQUENCE: 95

Trp Gly Asn His Gly Tyr Thr Glu
1               5

<210> SEQ ID NO 96
<211> LENGTH: 7
<212> TYPE: PRT
<213> ORGANISM: Artificial Sequence
<220> FEATURE:
<223> OTHER INFORMATION: synthetic genetically encoded small illuminant
      (GESI) Peptide 12 variant from alanine walk, Peptide 12 deletion

<400> SEQUENCE: 96

Gly Asn His Gly Tyr Thr Glu
1               5

<210> SEQ ID NO 97
<211> LENGTH: 6
<212> TYPE: PRT
<213> ORGANISM: Artificial Sequence
<220> FEATURE:
<223> OTHER INFORMATION: synthetic genetically encoded small illuminant
      (GESI) Peptide 12 variant from alanine walk, Peptide 12 deletion

<400> SEQUENCE: 97

Asn His Gly Tyr Thr Glu
1               5

<210> SEQ ID NO 98
<211> LENGTH: 4
<212> TYPE: PRT
<213> ORGANISM: Artificial Sequence
<220> FEATURE:

```
<223> OTHER INFORMATION: synthetic genetically encoded small illuminant
      (GESI) Peptide 12 variant from alanine walk, Peptide 12 deletion

<400> SEQUENCE: 98

Gly Tyr Thr Glu
1

<210> SEQ ID NO 99
<211> LENGTH: 3
<212> TYPE: PRT
<213> ORGANISM: Artificial Sequence
<220> FEATURE:
<223> OTHER INFORMATION: synthetic genetically encoded small illuminant
      (GESI) Peptide 12 variant from alanine walk, Peptide 12 deletion

<400> SEQUENCE: 99

Tyr Thr Glu
1

<210> SEQ ID NO 100
<211> LENGTH: 3
<212> TYPE: PRT
<213> ORGANISM: Artificial Sequence
<220> FEATURE:
<223> OTHER INFORMATION: synthetic genetically encoded small illuminant
      (GESI) Peptide 12 deletion

<400> SEQUENCE: 100

Asp Trp Trp
1

<210> SEQ ID NO 101
<211> LENGTH: 4
<212> TYPE: PRT
<213> ORGANISM: Artificial Sequence
<220> FEATURE:
<223> OTHER INFORMATION: synthetic genetically encoded small illuminant
      (GESI) Peptide 12 deletion

<400> SEQUENCE: 101

Asp Trp Trp Asp
1

<210> SEQ ID NO 102
<211> LENGTH: 5
<212> TYPE: PRT
<213> ORGANISM: Artificial Sequence
<220> FEATURE:
<223> OTHER INFORMATION: synthetic genetically encoded small illuminant
      (GESI) Peptide 12 deletion

<400> SEQUENCE: 102

Asp Trp Trp Asp Trp
1               5

<210> SEQ ID NO 103
<211> LENGTH: 6
<212> TYPE: PRT
<213> ORGANISM: Artificial Sequence
<220> FEATURE:
<223> OTHER INFORMATION: synthetic genetically encoded small illuminant
      (GESI) Peptide 12 deletion

<400> SEQUENCE: 103

Asp Trp Trp Asp Trp Gly
1               5
```

```
<210> SEQ ID NO 104
<211> LENGTH: 7
<212> TYPE: PRT
<213> ORGANISM: Artificial Sequence
<220> FEATURE:
<223> OTHER INFORMATION: synthetic genetically encoded small illuminant
      (GESI) Peptide 12 deletion

<400> SEQUENCE: 104

Asp Trp Trp Asp Trp Gly Asn
1               5

<210> SEQ ID NO 105
<211> LENGTH: 8
<212> TYPE: PRT
<213> ORGANISM: Artificial Sequence
<220> FEATURE:
<223> OTHER INFORMATION: synthetic genetically encoded small illuminant
      (GESI) Peptide 12 deletion

<400> SEQUENCE: 105

Asp Trp Trp Asp Trp Gly Asn His
1               5

<210> SEQ ID NO 106
<211> LENGTH: 9
<212> TYPE: PRT
<213> ORGANISM: Artificial Sequence
<220> FEATURE:
<223> OTHER INFORMATION: synthetic genetically encoded small illuminant
      (GESI) Peptide 12 deletion

<400> SEQUENCE: 106

Asp Trp Trp Asp Trp Gly Asn His Gly
1               5

<210> SEQ ID NO 107
<211> LENGTH: 10
<212> TYPE: PRT
<213> ORGANISM: Artificial Sequence
<220> FEATURE:
<223> OTHER INFORMATION: synthetic genetically encoded small illuminant
      (GESI) Peptide 12 deletion

<400> SEQUENCE: 107

Asp Trp Trp Asp Trp Gly Asn His Gly Tyr
1               5                   10

<210> SEQ ID NO 108
<211> LENGTH: 11
<212> TYPE: PRT
<213> ORGANISM: Artificial Sequence
<220> FEATURE:
<223> OTHER INFORMATION: synthetic genetically encoded small illuminant
      (GESI) Peptide 12 deletion

<400> SEQUENCE: 108

Asp Trp Trp Asp Trp Gly Asn His Gly Tyr Thr
1               5                   10

<210> SEQ ID NO 109
<211> LENGTH: 12
<212> TYPE: PRT
<213> ORGANISM: Artificial Sequence
<220> FEATURE:
<223> OTHER INFORMATION: synthetic genetically encoded small illuminant
      (GESI) malachite green (MG) binding Peptide 2 from alanine walk

<400> SEQUENCE: 109
```

Asp Trp Trp Trp Asp Gly Phe Glu Arg Leu Glu Glu
1               5                   10

<210> SEQ ID NO 110
<211> LENGTH: 12
<212> TYPE: PRT
<213> ORGANISM: Artificial Sequence
<220> FEATURE:
<223> OTHER INFORMATION: synthetic genetically encoded small illuminant
      (GESI) Peptide 2 variant from alanine walk

<400> SEQUENCE: 110

Asp Trp Trp Trp Asp Gly Phe Glu Arg Leu Glu Ala
1               5                   10

<210> SEQ ID NO 111
<211> LENGTH: 12
<212> TYPE: PRT
<213> ORGANISM: Artificial Sequence
<220> FEATURE:
<223> OTHER INFORMATION: synthetic genetically encoded small illuminant
      (GESI) Peptide 2 variant from alanine walk

<400> SEQUENCE: 111

Asp Trp Trp Trp Asp Gly Phe Glu Arg Leu Ala Glu
1               5                   10

<210> SEQ ID NO 112
<211> LENGTH: 12
<212> TYPE: PRT
<213> ORGANISM: Artificial Sequence
<220> FEATURE:
<223> OTHER INFORMATION: synthetic genetically encoded small illuminant
      (GESI) Peptide 2 variant from alanine walk

<400> SEQUENCE: 112

Asp Trp Trp Trp Asp Gly Phe Glu Arg Ala Glu Glu
1               5                   10

<210> SEQ ID NO 113
<211> LENGTH: 12
<212> TYPE: PRT
<213> ORGANISM: Artificial Sequence
<220> FEATURE:
<223> OTHER INFORMATION: synthetic genetically encoded small illuminant
      (GESI) Peptide 2 variant from alanine walk

<400> SEQUENCE: 113

Asp Trp Trp Trp Asp Gly Phe Glu Ala Leu Glu Glu
1               5                   10

<210> SEQ ID NO 114
<211> LENGTH: 12
<212> TYPE: PRT
<213> ORGANISM: Artificial Sequence
<220> FEATURE:
<223> OTHER INFORMATION: synthetic genetically encoded small illuminant
      (GESI) Peptide 2 variant from alanine walk

<400> SEQUENCE: 114

Asp Trp Trp Trp Asp Gly Phe Ala Arg Leu Glu Glu
1               5                   10

<210> SEQ ID NO 115
<211> LENGTH: 12
<212> TYPE: PRT
<213> ORGANISM: Artificial Sequence

```
<220> FEATURE:
<223> OTHER INFORMATION: synthetic genetically encoded small illuminant
      (GESI) Peptide 2 variant from alanine walk

<400> SEQUENCE: 115

Asp Trp Trp Trp Asp Gly Ala Glu Arg Leu Glu Glu
1               5                   10

<210> SEQ ID NO 116
<211> LENGTH: 12
<212> TYPE: PRT
<213> ORGANISM: Artificial Sequence
<220> FEATURE:
<223> OTHER INFORMATION: synthetic genetically encoded small illuminant
      (GESI) Peptide 2 variant from alanine walk

<400> SEQUENCE: 116

Asp Trp Trp Trp Asp Ala Phe Glu Arg Leu Glu Glu
1               5                   10

<210> SEQ ID NO 117
<211> LENGTH: 12
<212> TYPE: PRT
<213> ORGANISM: Artificial Sequence
<220> FEATURE:
<223> OTHER INFORMATION: synthetic genetically encoded small illuminant
      (GESI) Peptide 2 variant from alanine walk

<400> SEQUENCE: 117

Asp Trp Trp Trp Ala Gly Phe Glu Arg Leu Glu Glu
1               5                   10

<210> SEQ ID NO 118
<211> LENGTH: 12
<212> TYPE: PRT
<213> ORGANISM: Artificial Sequence
<220> FEATURE:
<223> OTHER INFORMATION: synthetic genetically encoded small illuminant
      (GESI) Peptide 2 variant from alanine walk

<400> SEQUENCE: 118

Asp Trp Trp Ala Asp Gly Phe Glu Arg Leu Glu Glu
1               5                   10

<210> SEQ ID NO 119
<211> LENGTH: 12
<212> TYPE: PRT
<213> ORGANISM: Artificial Sequence
<220> FEATURE:
<223> OTHER INFORMATION: synthetic genetically encoded small illuminant
      (GESI) Peptide 2 variant from alanine walk

<400> SEQUENCE: 119

Asp Trp Ala Trp Asp Gly Phe Glu Arg Leu Glu Glu
1               5                   10

<210> SEQ ID NO 120
<211> LENGTH: 12
<212> TYPE: PRT
<213> ORGANISM: Artificial Sequence
<220> FEATURE:
<223> OTHER INFORMATION: synthetic genetically encoded small illuminant
      (GESI) Peptide 2 variant from alanine walk

<400> SEQUENCE: 120

Asp Ala Trp Trp Asp Gly Phe Glu Arg Leu Glu Glu
1               5                   10
```

```
<210> SEQ ID NO 121
<211> LENGTH: 12
<212> TYPE: PRT
<213> ORGANISM: Artificial Sequence
<220> FEATURE:
<223> OTHER INFORMATION: synthetic genetically encoded small illuminant
      (GESI) Peptide 2 variant from alanine walk

<400> SEQUENCE: 121

Ala Trp Trp Trp Asp Gly Phe Glu Arg Leu Glu Glu
1               5                   10

<210> SEQ ID NO 122
<211> LENGTH: 11
<212> TYPE: PRT
<213> ORGANISM: Artificial Sequence
<220> FEATURE:
<223> OTHER INFORMATION: synthetic genetically encoded small illuminant
      (GESI) Peptide 2 deletion

<400> SEQUENCE: 122

Asp Trp Trp Trp Asp Phe Glu Arg Leu Glu Glu
1               5                   10

<210> SEQ ID NO 123
<211> LENGTH: 3
<212> TYPE: PRT
<213> ORGANISM: Artificial Sequence
<220> FEATURE:
<223> OTHER INFORMATION: synthetic genetically encoded small illuminant
      (GESI) Peptide 2 deletion

<400> SEQUENCE: 123

Leu Glu Glu
1

<210> SEQ ID NO 124
<211> LENGTH: 4
<212> TYPE: PRT
<213> ORGANISM: Artificial Sequence
<220> FEATURE:
<223> OTHER INFORMATION: synthetic genetically encoded small illuminant
      (GESI) Peptide 2 deletion

<400> SEQUENCE: 124

Arg Leu Glu Glu
1

<210> SEQ ID NO 125
<211> LENGTH: 5
<212> TYPE: PRT
<213> ORGANISM: Artificial Sequence
<220> FEATURE:
<223> OTHER INFORMATION: synthetic genetically encoded small illuminant
      (GESI) Peptide 2 deletion

<400> SEQUENCE: 125

Glu Arg Leu Glu Glu
1               5

<210> SEQ ID NO 126
<211> LENGTH: 6
<212> TYPE: PRT
<213> ORGANISM: Artificial Sequence
<220> FEATURE:
<223> OTHER INFORMATION: synthetic genetically encoded small illuminant
      (GESI) Peptide 2 deletion
```

```
<400> SEQUENCE: 126

Phe Glu Arg Leu Glu Glu
1               5

<210> SEQ ID NO 127
<211> LENGTH: 7
<212> TYPE: PRT
<213> ORGANISM: Artificial Sequence
<220> FEATURE:
<223> OTHER INFORMATION: synthetic genetically encoded small illuminant
      (GESI) Peptide 2 deletion

<400> SEQUENCE: 127

Gly Phe Glu Arg Leu Glu Glu
1               5

<210> SEQ ID NO 128
<211> LENGTH: 8
<212> TYPE: PRT
<213> ORGANISM: Artificial Sequence
<220> FEATURE:
<223> OTHER INFORMATION: synthetic genetically encoded small illuminant
      (GESI) Peptide 2 deletion

<400> SEQUENCE: 128

Asp Gly Phe Glu Arg Leu Glu Glu
1               5

<210> SEQ ID NO 129
<211> LENGTH: 8
<212> TYPE: PRT
<213> ORGANISM: Artificial Sequence
<220> FEATURE:
<223> OTHER INFORMATION: synthetic genetically encoded small illuminant
      (GESI) Peptide 2 deletion

<400> SEQUENCE: 129

Trp Asp Phe Glu Arg Leu Glu Glu
1               5

<210> SEQ ID NO 130
<211> LENGTH: 9
<212> TYPE: PRT
<213> ORGANISM: Artificial Sequence
<220> FEATURE:
<223> OTHER INFORMATION: synthetic genetically encoded small illuminant
      (GESI) Peptide 2 deletion

<400> SEQUENCE: 130

Trp Trp Asp Phe Glu Arg Leu Glu Glu
1               5

<210> SEQ ID NO 131
<211> LENGTH: 10
<212> TYPE: PRT
<213> ORGANISM: Artificial Sequence
<220> FEATURE:
<223> OTHER INFORMATION: synthetic genetically encoded small illuminant
      (GESI) Peptide 2 deletion

<400> SEQUENCE: 131

Trp Trp Trp Asp Phe Glu Arg Leu Glu Glu
1               5                   10

<210> SEQ ID NO 132
<211> LENGTH: 11
<212> TYPE: PRT
```

<213> ORGANISM: Artificial Sequence
<220> FEATURE:
<223> OTHER INFORMATION: synthetic genetically encoded small illuminant
      (GESI) Peptide 2 deletion

<400> SEQUENCE: 132

Asp Trp Trp Trp Asp Gly Phe Glu Arg Leu Glu
1               5                   10

<210> SEQ ID NO 133
<211> LENGTH: 10
<212> TYPE: PRT
<213> ORGANISM: Artificial Sequence
<220> FEATURE:
<223> OTHER INFORMATION: synthetic genetically encoded small illuminant
      (GESI) Peptide 2 deletion

<400> SEQUENCE: 133

Asp Trp Trp Trp Asp Gly Phe Glu Arg Leu
1               5                   10

<210> SEQ ID NO 134
<211> LENGTH: 9
<212> TYPE: PRT
<213> ORGANISM: Artificial Sequence
<220> FEATURE:
<223> OTHER INFORMATION: synthetic genetically encoded small illuminant
      (GESI) Peptide 2 deletion

<400> SEQUENCE: 134

Asp Trp Trp Trp Asp Gly Phe Glu Arg
1               5

<210> SEQ ID NO 135
<211> LENGTH: 8
<212> TYPE: PRT
<213> ORGANISM: Artificial Sequence
<220> FEATURE:
<223> OTHER INFORMATION: synthetic genetically encoded small illuminant
      (GESI) Peptide 2 deletion

<400> SEQUENCE: 135

Asp Trp Trp Trp Asp Gly Phe Glu
1               5

<210> SEQ ID NO 136
<211> LENGTH: 7
<212> TYPE: PRT
<213> ORGANISM: Artificial Sequence
<220> FEATURE:
<223> OTHER INFORMATION: synthetic genetically encoded small illuminant
      (GESI) Peptide 2 deletion

<400> SEQUENCE: 136

Asp Trp Trp Trp Asp Gly Phe
1               5

<210> SEQ ID NO 137
<211> LENGTH: 6
<212> TYPE: PRT
<213> ORGANISM: Artificial Sequence
<220> FEATURE:
<223> OTHER INFORMATION: synthetic genetically encoded small illuminant
      (GESI) Peptide 2 deletion

<400> SEQUENCE: 137

Asp Trp Trp Trp Asp Gly
1               5

```
<210> SEQ ID NO 138
<211> LENGTH: 5
<212> TYPE: PRT
<213> ORGANISM: Artificial Sequence
<220> FEATURE:
<223> OTHER INFORMATION: synthetic genetically encoded small illuminant
      (GESI) Peptide 2 deletion

<400> SEQUENCE: 138

Asp Trp Trp Trp Asp
1               5

<210> SEQ ID NO 139
<211> LENGTH: 4
<212> TYPE: PRT
<213> ORGANISM: Artificial Sequence
<220> FEATURE:
<223> OTHER INFORMATION: synthetic genetically encoded small illuminant
      (GESI) Peptide 2 deletion

<400> SEQUENCE: 139

Asp Trp Trp Trp
1

<210> SEQ ID NO 140
<211> LENGTH: 14
<212> TYPE: PRT
<213> ORGANISM: Artificial Sequence
<220> FEATURE:
<223> OTHER INFORMATION: synthetic genetically encoded small illuminant
      (GESI) linear OBOC library L-1, cyclic OBOC library L-2
<220> FEATURE:
<221> NAME/KEY: VARIANT
<222> LOCATION: (1)..(13)
<223> OTHER INFORMATION: Xaa = any natural amino acid except Cys
<220> FEATURE:
<221> NAME/KEY: PHOSPHORYLATION
<222> LOCATION: (5)..(5)
<223> OTHER INFORMATION: Tyr can be phosphorylated

<400> SEQUENCE: 140

Xaa Xaa Tyr Ile Tyr Gly Ser Phe Lys Xaa Xaa Xaa Xaa Cys
1               5                   10

<210> SEQ ID NO 141
<211> LENGTH: 15
<212> TYPE: PRT
<213> ORGANISM: Artificial Sequence
<220> FEATURE:
<223> OTHER INFORMATION: synthetic genetically encoded small illuminant
      (GESI) linear OBOC library L-1
<220> FEATURE:
<221> NAME/KEY: VARIANT
<222> LOCATION: (1)..(13)
<223> OTHER INFORMATION: Xaa = any natural amino acid except Cys
<220> FEATURE:
<221> NAME/KEY: PHOSPHORYLATION
<222> LOCATION: (5)..(5)
<223> OTHER INFORMATION: Tyr can be phosphorylated
<220> FEATURE:
<221> NAME/KEY: MOD_RES
<222> LOCATION: (15)..(15)
<223> OTHER INFORMATION: 3-nitrotyrosine

<400> SEQUENCE: 141

Xaa Xaa Tyr Ile Tyr Gly Ser Phe Lys Xaa Xaa Xaa Xaa Cys Tyr
1               5                   10                  15

<210> SEQ ID NO 142
```

```
<211> LENGTH: 16
<212> TYPE: PRT
<213> ORGANISM: Artificial Sequence
<220> FEATURE:
<223> OTHER INFORMATION: synthetic genetically encoded small illuminant
      (GESI) cyclic OBOC library L-2
<220> FEATURE:
<221> NAME/KEY: DISULFID
<222> LOCATION: (1)..(15)
<220> FEATURE:
<221> NAME/KEY: VARIANT
<222> LOCATION: (2)..(14)
<223> OTHER INFORMATION: Xaa = any natural amino acid except Cys
<220> FEATURE:
<221> NAME/KEY: PHOSPHORYLATION
<222> LOCATION: (6)..(6)
<223> OTHER INFORMATION: Tyr can be phosphorylated
<220> FEATURE:
<221> NAME/KEY: MOD_RES
<222> LOCATION: (16)..(16)
<223> OTHER INFORMATION: 3-nitrotyrosine

<400> SEQUENCE: 142

Cys Xaa Xaa Tyr Ile Tyr Gly Ser Phe Lys Xaa Xaa Xaa Xaa Cys Tyr
1               5                   10                  15

<210> SEQ ID NO 143
<211> LENGTH: 11
<212> TYPE: PRT
<213> ORGANISM: Artificial Sequence
<220> FEATURE:
<223> OTHER INFORMATION: synthetic genetically encoded small illuminant
      (GESI) linear OBOC library L-3
<220> FEATURE:
<221> NAME/KEY: VARIANT
<222> LOCATION: (1)..(10)
<223> OTHER INFORMATION: Xaa = any natural amino acid except Cys
<220> FEATURE:
<221> NAME/KEY: PHOSPHORYLATION
<222> LOCATION: (6)..(6)
<223> OTHER INFORMATION: Ser can be phosphorylated

<400> SEQUENCE: 143

Xaa Xaa Arg Arg Xaa Ser Xaa Xaa Xaa Xaa Cys
1               5                   10

<210> SEQ ID NO 144
<211> LENGTH: 12
<212> TYPE: PRT
<213> ORGANISM: Artificial Sequence
<220> FEATURE:
<223> OTHER INFORMATION: synthetic genetically encoded small illuminant
      (GESI) linear OBOC library L-3
<220> FEATURE:
<221> NAME/KEY: VARIANT
<222> LOCATION: (1)..(10)
<223> OTHER INFORMATION: Xaa = any natural amino acid except Cys
<220> FEATURE:
<221> NAME/KEY: PHOSPHORYLATION
<222> LOCATION: (6)..(6)
<223> OTHER INFORMATION: Ser can be phosphorylated
<220> FEATURE:
<221> NAME/KEY: MOD_RES
<222> LOCATION: (12)..(12)
<223> OTHER INFORMATION: 3-nitrotyrosine

<400> SEQUENCE: 144

Xaa Xaa Arg Arg Xaa Ser Xaa Xaa Xaa Xaa Cys Tyr
1               5                   10

<210> SEQ ID NO 145
<211> LENGTH: 12
<212> TYPE: PRT
```

```
<213> ORGANISM: Artificial Sequence
<220> FEATURE:
<223> OTHER INFORMATION: synthetic genetically encoded small illuminant
      (GESI) cyclic OBOC library L-4
<220> FEATURE:
<221> NAME/KEY: DISULFID
<222> LOCATION: (1)..(12)
<220> FEATURE:
<221> NAME/KEY: VARIANT
<222> LOCATION: (2)..(11)
<223> OTHER INFORMATION: Xaa = any natural amino acid except Cys
<220> FEATURE:
<221> NAME/KEY: PHOSPHORYLATION
<222> LOCATION: (7)..(7)
<223> OTHER INFORMATION: Ser can be phosphorylated

<400> SEQUENCE: 145

Cys Xaa Xaa Arg Arg Xaa Ser Xaa Xaa Xaa Xaa Cys
1               5                   10

<210> SEQ ID NO 146
<211> LENGTH: 13
<212> TYPE: PRT
<213> ORGANISM: Artificial Sequence
<220> FEATURE:
<223> OTHER INFORMATION: synthetic genetically encoded small illuminant
      (GESI) cyclic OBOC library L-4
<220> FEATURE:
<221> NAME/KEY: DISULFID
<222> LOCATION: (1)..(12)
<220> FEATURE:
<221> NAME/KEY: VARIANT
<222> LOCATION: (2)..(11)
<223> OTHER INFORMATION: Xaa = any natural amino acid except Cys
<220> FEATURE:
<221> NAME/KEY: PHOSPHORYLATION
<222> LOCATION: (13)..(13)
<223> OTHER INFORMATION: Ser can be phophorylated
<220> FEATURE:
<221> NAME/KEY: MOD_RES
<222> LOCATION: (13)..(13)
<223> OTHER INFORMATION: 3-nitrotyrosine

<400> SEQUENCE: 146

Cys Xaa Xaa Arg Arg Xaa Ser Xaa Xaa Xaa Xaa Cys Tyr
1               5                   10

<210> SEQ ID NO 147
<211> LENGTH: 12
<212> TYPE: PRT
<213> ORGANISM: Artificial Sequence
<220> FEATURE:
<223> OTHER INFORMATION: synthetic genetically encoded small illuminant
      (GESI) OBOC library
<220> FEATURE:
<221> NAME/KEY: VARIANT
<222> LOCATION: (1)..(12)
<223> OTHER INFORMATION: Xaa = any amino acid
<220> FEATURE:
<221> NAME/KEY: MOD_RES
<222> LOCATION: (12)..(12)
<223> OTHER INFORMATION: Xaa affixed to polyethylene glycol grafted
      polystyrene bead

<400> SEQUENCE: 147

Xaa Xaa Xaa Xaa Xaa Xaa Xaa Xaa Xaa Xaa Xaa Xaa
1               5                   10

<210> SEQ ID NO 148
<211> LENGTH: 6
<212> TYPE: PRT
<213> ORGANISM: Artificial Sequence
<220> FEATURE:
```

```
<223> OTHER INFORMATION: synthetic genetically encoded small illuminant
      (GESI) OBOC library
<220> FEATURE:
<221> NAME/KEY: VARIANT
<222> LOCATION: (1)..(6)
<223> OTHER INFORMATION: Xaa = any amino acid

<400> SEQUENCE: 148

Xaa Xaa Xaa Xaa Xaa Xaa
1               5

<210> SEQ ID NO 149
<211> LENGTH: 11
<212> TYPE: PRT
<213> ORGANISM: Artificial Sequence
<220> FEATURE:
<223> OTHER INFORMATION: synthetic genetically encoded small illuminant
      (GESI) OBOC library
<220> FEATURE:
<221> NAME/KEY: VARIANT
<222> LOCATION: (1)..(11)
<223> OTHER INFORMATION: Xaa = any amino acid
<220> FEATURE:
<221> NAME/KEY: MOD_RES
<222> LOCATION: (11)..(11)
<223> OTHER INFORMATION: Xaa affixed to polyethylene glycol grafted
      polystyrene bead

<400> SEQUENCE: 149

Xaa Xaa Xaa Xaa Xaa Ser Pro Xaa Xaa Xaa Xaa
1               5                   10

<210> SEQ ID NO 150
<211> LENGTH: 12
<212> TYPE: PRT
<213> ORGANISM: Artificial Sequence
<220> FEATURE:
<223> OTHER INFORMATION: synthetic genetically encoded small illuminant
      (GESI) OBOC library
<220> FEATURE:
<221> NAME/KEY: VARIANT
<222> LOCATION: (1)..(12)
<223> OTHER INFORMATION: Xaa = any amino acid
<220> FEATURE:
<221> NAME/KEY: PHOSPHORYLATION
<222> LOCATION: (8)..(8)
<223> OTHER INFORMATION: Ser can be phosphorylated
<220> FEATURE:
<221> NAME/KEY: MOD_RES
<222> LOCATION: (12)..(12)
<223> OTHER INFORMATION: Xaa affixed to polyethylene glycol grafted
      polystyrene bead

<400> SEQUENCE: 150

Xaa Xaa Xaa Xaa Arg Arg Xaa Ser Xaa Xaa Xaa Xaa
1               5                   10

<210> SEQ ID NO 151
<211> LENGTH: 10
<212> TYPE: PRT
<213> ORGANISM: Artificial Sequence
<220> FEATURE:
<223> OTHER INFORMATION: synthetic genetically encoded small illuminant
      (GESI) OBOC library
<220> FEATURE:
<221> NAME/KEY: VARIANT
<222> LOCATION: (1)..(10)
<223> OTHER INFORMATION: Xaa = any amino acid
<220> FEATURE:
<221> NAME/KEY: PHOSPHORYLATION
<222> LOCATION: (5)..(5)
<223> OTHER INFORMATION: Ser can be phosphorylated
<220> FEATURE:
```

```
<221> NAME/KEY: MOD_RES
<222> LOCATION: (10)..(10)
<223> OTHER INFORMATION: Xaa affixed to polyethylene glycol grafted
      polystyrene bead

<400> SEQUENCE: 151

Xaa Xaa Xaa Xaa Ser Pro Xaa Xaa Xaa Xaa
1               5                   10

<210> SEQ ID NO 152
<211> LENGTH: 20
<212> TYPE: PRT
<213> ORGANISM: Artificial Sequence
<220> FEATURE:
<223> OTHER INFORMATION: synthetic genetically encoded small illuminant
      (GESI) OBOC library
<220> FEATURE:
<221> NAME/KEY: MOD_RES
<222> LOCATION: (2)..(2)
<223> OTHER INFORMATION: Lys can be acetylated or methylated
<220> FEATURE:
<221> NAME/KEY: PHOSPHORYLATION
<222> LOCATION: (3)..(3)
<223> OTHER INFORMATION: Ser can be phosphorylated
<220> FEATURE:
<221> NAME/KEY: VARIANT
<222> LOCATION: (7)..(7)
<223> OTHER INFORMATION: Xaa = any amino acid
<220> FEATURE:
<221> NAME/KEY: VARIANT
<222> LOCATION: (8)..(16)
<223> OTHER INFORMATION: Xaa = any amino acid, may be present or absent
<220> FEATURE:
<221> NAME/KEY: MOD_RES
<222> LOCATION: (18)..(18)
<223> OTHER INFORMATION: Lys can be acetylated or methylated
<220> FEATURE:
<221> NAME/KEY: MOD_RES
<222> LOCATION: (20)..(20)
<223> OTHER INFORMATION: Pro affixed to polyethylene glycol grafted
      polystyrene bead

<400> SEQUENCE: 152

Arg Lys Ser Thr Thr Gly Xaa Xaa Xaa Xaa Xaa Xaa Xaa Xaa Xaa
1               5                   10                  15

Gly Lys Ala Pro
            20

<210> SEQ ID NO 153
<211> LENGTH: 10
<212> TYPE: PRT
<213> ORGANISM: Artificial Sequence
<220> FEATURE:
<223> OTHER INFORMATION: synthetic genetically encoded small illuminant
      (GESI) OBOC library
<220> FEATURE:
<221> NAME/KEY: VARIANT
<222> LOCATION: (1)..(4)
<223> OTHER INFORMATION: Xaa = any amino acid
<220> FEATURE:
<221> NAME/KEY: PHOSPHORYLATION
<222> LOCATION: (7)..(7)
<223> OTHER INFORMATION: Thr can be phosphorylated
<220> FEATURE:
<221> NAME/KEY: METHYLATION
<222> LOCATION: (8)..(8)
<223> OTHER INFORMATION: Lys can be methylated
<220> FEATURE:
<221> NAME/KEY: MOD_RES
<222> LOCATION: (10)..(10)
<223> OTHER INFORMATION: Thr affixed to polyethylene glycol grafted
      polystyrene bead

<400> SEQUENCE: 153
```

```
Xaa Xaa Xaa Xaa Ala Arg Thr Lys Gln Thr
1               5                   10

<210> SEQ ID NO 154
<211> LENGTH: 15
<212> TYPE: PRT
<213> ORGANISM: Artificial Sequence
<220> FEATURE:
<223> OTHER INFORMATION: synthetic genetically encoded small illuminant
      (GESI) peptide reporter X6-1 for c-src protein tyrosine kinase
<220> FEATURE:
<221> NAME/KEY: PHOSPHORYLATION
<222> LOCATION: (3)..(3)
<223> OTHER INFORMATION: Tyr can be phosphorylated

<400> SEQUENCE: 154

Tyr Ile Tyr Gly Ser Phe Lys Lys Lys Tyr Phe Gly Val His Ser
1               5                   10                  15

<210> SEQ ID NO 155
<211> LENGTH: 15
<212> TYPE: PRT
<213> ORGANISM: Artificial Sequence
<220> FEATURE:
<223> OTHER INFORMATION: synthetic genetically encoded small illuminant
      (GESI) peptide reporter for c-src protein tyrosine kinase
<220> FEATURE:
<221> NAME/KEY: PHOSPHORYLATION
<222> LOCATION: (3)..(3)
<223> OTHER INFORMATION: Tyr can be phosphorylated

<400> SEQUENCE: 155

Tyr Ile Tyr Gly Ser Phe Lys Lys Lys Glu Ser Val Tyr Ile Glu
1               5                   10                  15

<210> SEQ ID NO 156
<211> LENGTH: 16
<212> TYPE: PRT
<213> ORGANISM: Artificial Sequence
<220> FEATURE:
<223> OTHER INFORMATION: synthetic genetically encoded small illuminant
      (GESI) peptide reporter X7-6 for c-src protein tyrosine kinase
<220> FEATURE:
<221> NAME/KEY: PHOSPHORYLATION
<222> LOCATION: (3)..(3)
<223> OTHER INFORMATION: Tyr can be phosphorylated

<400> SEQUENCE: 156

Tyr Ile Tyr Gly Ser Phe Lys Lys Lys Tyr Phe Asn Ala Ile Asn Thr
1               5                   10                  15

<210> SEQ ID NO 157
<211> LENGTH: 17
<212> TYPE: PRT
<213> ORGANISM: Artificial Sequence
<220> FEATURE:
<223> OTHER INFORMATION: synthetic genetically encoded small illuminant
      (GESI) peptide reporter for c-src protein tyrosine kinase
<220> FEATURE:
<221> NAME/KEY: PHOSPHORYLATION
<222> LOCATION: (3)..(3)
<223> OTHER INFORMATION: Tyr can be phosphorylated

<400> SEQUENCE: 157

Tyr Ile Tyr Gly Ser Phe Lys Lys Lys Asn Tyr His Tyr Glu Ile Glu
1               5                   10                  15

Tyr
```

```
<210> SEQ ID NO 158
<211> LENGTH: 17
<212> TYPE: PRT
<213> ORGANISM: Artificial Sequence
<220> FEATURE:
<223> OTHER INFORMATION: synthetic genetically encoded small illuminant
      (GESI) peptide reporter X8-2 for c-src protein tyrosine kinase
<220> FEATURE:
<221> NAME/KEY: PHOSPHORYLATION
<222> LOCATION: (3)..(3)
<223> OTHER INFORMATION: Tyr can be phosphorylated

<400> SEQUENCE: 158

Tyr Ile Tyr Gly Ser Phe Lys Lys Lys Asn Tyr Thr Trp Tyr Val Ser
1               5                   10                  15

Tyr

<210> SEQ ID NO 159
<211> LENGTH: 17
<212> TYPE: PRT
<213> ORGANISM: Artificial Sequence
<220> FEATURE:
<223> OTHER INFORMATION: synthetic genetically encoded small illuminant
      (GESI) peptide reporter for c-src protein tyrosine kinase
<220> FEATURE:
<221> NAME/KEY: PHOSPHORYLATION
<222> LOCATION: (3)..(3)
<223> OTHER INFORMATION: Tyr can be phosphorylated

<400> SEQUENCE: 159

Tyr Ile Tyr Gly Ser Phe Lys Lys Lys Asp Gln Glu Phe Thr Ala Phe
1               5                   10                  15

Met

<210> SEQ ID NO 160
<211> LENGTH: 18
<212> TYPE: PRT
<213> ORGANISM: Artificial Sequence
<220> FEATURE:
<223> OTHER INFORMATION: synthetic genetically encoded small illuminant
      (GESI) peptide reporter X9-1 for c-src protein tyrosine kinase
<220> FEATURE:
<221> NAME/KEY: PHOSPHORYLATION
<222> LOCATION: (3)..(3)
<223> OTHER INFORMATION: Tyr can be phosphorylated

<400> SEQUENCE: 160

Tyr Ile Tyr Gly Ser Phe Lys Lys Lys Asp Arg Met Phe Thr Thr Trp
1               5                   10                  15

Ser Asp

<210> SEQ ID NO 161
<211> LENGTH: 18
<212> TYPE: PRT
<213> ORGANISM: Artificial Sequence
<220> FEATURE:
<223> OTHER INFORMATION: synthetic genetically encoded small illuminant
      (GESI) peptide reporter for c-src protein tyrosine kinase
<220> FEATURE:
<221> NAME/KEY: PHOSPHORYLATION
<222> LOCATION: (3)..(3)
<223> OTHER INFORMATION: Tyr can be phosphorylated

<400> SEQUENCE: 161

Tyr Ile Tyr Gly Ser Phe Lys Lys Lys Phe Met Leu Trp Met Asp Glu
1               5                   10                  15

Thr Tyr
```

-continued

```
<210> SEQ ID NO 162
<211> LENGTH: 19
<212> TYPE: PRT
<213> ORGANISM: Artificial Sequence
<220> FEATURE:
<223> OTHER INFORMATION: synthetic genetically encoded small illuminant
      (GESI) peptide reporter for c-src protein tyrosine kinase
<220> FEATURE:
<221> NAME/KEY: PHOSPHORYLATION
<222> LOCATION: (3)..(3)
<223> OTHER INFORMATION: Tyr can be phosphorylated

<400> SEQUENCE: 162

Tyr Ile Tyr Gly Ser Phe Lys Lys Lys Phe Met Leu Trp Met Asp Glu
1               5                   10                  15

Thr Tyr Gly

<210> SEQ ID NO 163
<211> LENGTH: 17
<212> TYPE: PRT
<213> ORGANISM: Artificial Sequence
<220> FEATURE:
<223> OTHER INFORMATION: synthetic genetically encoded small illuminant
      (GESI) peptide
<220> FEATURE:
<221> NAME/KEY: PHOSPHORYLATION
<222> LOCATION: (4)..(4)
<223> OTHER INFORMATION: Tyr can be phosphorylated

<400> SEQUENCE: 163

Glu Ala Ile Tyr Ala Ala Pro Phe Ala Lys Lys Tyr Thr Phe Glu Leu
1               5                   10                  15

Thr

<210> SEQ ID NO 164
<211> LENGTH: 19
<212> TYPE: PRT
<213> ORGANISM: Artificial Sequence
<220> FEATURE:
<223> OTHER INFORMATION: synthetic genetically encoded small illuminant
      (GESI) peptide
<220> FEATURE:
<221> NAME/KEY: PHOSPHORYLATION
<222> LOCATION: (4)..(4)
<223> OTHER INFORMATION: Tyr can be phosphorylated

<400> SEQUENCE: 164

Glu Ala Ile Tyr Ala Ala Pro Phe Ala Lys Lys Gly Tyr Trp Gly Trp
1               5                   10                  15

Phe Thr Phe

<210> SEQ ID NO 165
<211> LENGTH: 19
<212> TYPE: PRT
<213> ORGANISM: Artificial Sequence
<220> FEATURE:
<223> OTHER INFORMATION: synthetic genetically encoded small illuminant
      (GESI) peptide LLT4
<220> FEATURE:
<221> NAME/KEY: PHOSPHORYLATION
<222> LOCATION: (4)..(4)
<223> OTHER INFORMATION: Tyr can be phosphorylated

<400> SEQUENCE: 165

Glu Ala Ile Tyr Ala Ala Pro Phe Ala Lys Lys Leu Tyr Ile Met Asp
1               5                   10                  15

Gly Trp Phe
```

<210> SEQ ID NO 166
<211> LENGTH: 16
<212> TYPE: PRT
<213> ORGANISM: Artificial Sequence
<220> FEATURE:
<223> OTHER INFORMATION: synthetic genetically encoded small illuminant
     (GESI) peptide
<220> FEATURE:
<221> NAME/KEY: PHOSPHORYLATION
<222> LOCATION: (5)..(5)
<223> OTHER INFORMATION: Ser can be phosphorylated

<400> SEQUENCE: 166

Leu Arg Arg Ala Ser Leu Pro Phe Met Met Leu Trp Leu Trp Ser Lys
1               5                   10                  15

<210> SEQ ID NO 167
<211> LENGTH: 15
<212> TYPE: PRT
<213> ORGANISM: Artificial Sequence
<220> FEATURE:
<223> OTHER INFORMATION: synthetic genetically encoded small illuminant
     (GESI) peptide
<220> FEATURE:
<221> NAME/KEY: PHOSPHORYLATION
<222> LOCATION: (5)..(5)
<223> OTHER INFORMATION: Ser can be phosphorylated

<400> SEQUENCE: 167

Leu Arg Arg Ala Ser Leu Arg Glu Ile Phe Val Ser Glu Trp Met
1               5                   10                  15

<210> SEQ ID NO 168
<211> LENGTH: 12
<212> TYPE: PRT
<213> ORGANISM: Artificial Sequence
<220> FEATURE:
<223> OTHER INFORMATION: synthetic genetically encoded small illuminant
     (GESI) peptide

<400> SEQUENCE: 168

Arg Pro Tyr Gln Ile Lys Asp Gln Ser Val Asn Ile
1               5                   10

<210> SEQ ID NO 169
<211> LENGTH: 12
<212> TYPE: PRT
<213> ORGANISM: Artificial Sequence
<220> FEATURE:
<223> OTHER INFORMATION: synthetic genetically encoded small illuminant
     (GESI) peptide

<400> SEQUENCE: 169

Gln Ala Phe Arg Tyr Glu Arg Asp Arg Trp Glu Arg
1               5                   10

<210> SEQ ID NO 170
<211> LENGTH: 12
<212> TYPE: PRT
<213> ORGANISM: Artificial Sequence
<220> FEATURE:
<223> OTHER INFORMATION: synthetic genetically encoded small illuminant
     (GESI) peptide

<400> SEQUENCE: 170

Asp Asp Ala Ile Thr Gly Arg Tyr Ser Ile Gly Glu
1               5                   10

<210> SEQ ID NO 171
<211> LENGTH: 12
<212> TYPE: PRT
<213> ORGANISM: Artificial Sequence
<220> FEATURE:
<223> OTHER INFORMATION: synthetic genetically encoded small illuminant
      (GESI) peptide

<400> SEQUENCE: 171

Asp Phe Asp Tyr Tyr Gly Pro Thr Met Trp Ser Glu
1               5                   10

<210> SEQ ID NO 172
<211> LENGTH: 17
<212> TYPE: PRT
<213> ORGANISM: Artificial Sequence
<220> FEATURE:
<223> OTHER INFORMATION: synthetic genetically encoded small illuminant
      (GESI) peptide

<400> SEQUENCE: 172

Glu Ala Ile Tyr Ala Ala Pro Phe Ala Lys Lys Tyr Thr Phe Glu Leu
1               5                   10                  15

Thr

<210> SEQ ID NO 173
<211> LENGTH: 18
<212> TYPE: PRT
<213> ORGANISM: Artificial Sequence
<220> FEATURE:
<223> OTHER INFORMATION: synthetic genetically encoded small illuminant
      (GESI) peptide

<400> SEQUENCE: 173

Glu Ala Ile Tyr Ala Ala Pro Phe Ala Lys Lys Phe Phe Gln Gly Tyr
1               5                   10                  15

Trp Phe

<210> SEQ ID NO 174
<211> LENGTH: 15
<212> TYPE: PRT
<213> ORGANISM: Artificial Sequence
<220> FEATURE:
<223> OTHER INFORMATION: synthetic genetically encoded small illuminant
      (GESI) peptide

<400> SEQUENCE: 174

Leu Arg Arg Ala Ser Leu Phe Tyr Gly Met Trp Tyr Pro Ser Thr
1               5                   10                  15

<210> SEQ ID NO 175
<211> LENGTH: 16
<212> TYPE: PRT
<213> ORGANISM: Artificial Sequence
<220> FEATURE:
<223> OTHER INFORMATION: synthetic genetically encoded small illuminant
      (GESI) peptide

<400> SEQUENCE: 175

Tyr Ile Tyr Gly Ser Phe Lys Lys Lys Pro Val Trp Phe Phe Arg Trp
1               5                   10                  15

<210> SEQ ID NO 176
<211> LENGTH: 15
<212> TYPE: PRT
<213> ORGANISM: Artificial Sequence -continued

```
<220> FEATURE:
<223> OTHER INFORMATION: synthetic genetically encoded small illuminant
      (GESI) peptide

<400> SEQUENCE: 176

Ile Tyr Gly Ser Phe Lys Lys Lys Pro Val Trp Phe Phe Arg Trp
1               5                   10                  15

<210> SEQ ID NO 177
<211> LENGTH: 14
<212> TYPE: PRT
<213> ORGANISM: Artificial Sequence
<220> FEATURE:
<223> OTHER INFORMATION: synthetic genetically encoded small illuminant
      (GESI) peptide

<400> SEQUENCE: 177

Tyr Gly Ser Phe Lys Lys Lys Pro Val Trp Phe Phe Arg Trp
1               5                   10

<210> SEQ ID NO 178
<211> LENGTH: 17
<212> TYPE: PRT
<213> ORGANISM: Artificial Sequence
<220> FEATURE:
<223> OTHER INFORMATION: synthetic genetically encoded small illuminant
      (GESI) peptide

<400> SEQUENCE: 178

Tyr Ile Tyr Gly Ser Phe Lys Lys Lys Val Val Asp Thr His Tyr Gln
1               5                   10                  15

Glu

<210> SEQ ID NO 179
<211> LENGTH: 16
<212> TYPE: PRT
<213> ORGANISM: Artificial Sequence
<220> FEATURE:
<223> OTHER INFORMATION: synthetic genetically encoded small illuminant
      (GESI) peptide

<400> SEQUENCE: 179

Ile Tyr Gly Ser Phe Lys Lys Lys Val Val Asp Thr His Tyr Gln Glu
1               5                   10                  15

<210> SEQ ID NO 180
<211> LENGTH: 15
<212> TYPE: PRT
<213> ORGANISM: Artificial Sequence
<220> FEATURE:
<223> OTHER INFORMATION: synthetic genetically encoded small illuminant
      (GESI) peptide

<400> SEQUENCE: 180

Tyr Gly Ser Phe Lys Lys Lys Val Val Asp Thr His Tyr Gln Glu
1               5                   10                  15

<210> SEQ ID NO 181
<211> LENGTH: 11
<212> TYPE: PRT
<213> ORGANISM: Artificial Sequence
<220> FEATURE:
<223> OTHER INFORMATION: synthetic genetically encoded small illuminant
      (GESI) peptide

<400> SEQUENCE: 181

Asp Ala Ile Thr Gly Arg Tyr Ser Ile Gly Glu
```

-continued

```
1               5                   10

<210> SEQ ID NO 182
<211> LENGTH: 10
<212> TYPE: PRT
<213> ORGANISM: Artificial Sequence
<220> FEATURE:
<223> OTHER INFORMATION: synthetic genetically encoded small illuminant
      (GESI) peptide

<400> SEQUENCE: 182

Ala Ile Thr Gly Arg Tyr Ser Ile Gly Glu
1               5                   10

<210> SEQ ID NO 183
<211> LENGTH: 12
<212> TYPE: PRT
<213> ORGANISM: Artificial Sequence
<220> FEATURE:
<223> OTHER INFORMATION: synthetic genetically encoded small illuminant
      (GESI) peptide
<220> FEATURE:
<221> NAME/KEY: VARIANT
<222> LOCATION: (1)..(2)
<223> OTHER INFORMATION: Xaa = Glu, Asp or absent
<220> FEATURE:
<221> NAME/KEY: VARIANT
<222> LOCATION: (3)..(4)
<223> OTHER INFORMATION: Xaa = Val, Leu, Ile, Met, Phe, Gly, Ala, Ser,
      Thr, Tyr, Trp, Cys or Pro
<220> FEATURE:
<221> NAME/KEY: VARIANT
<222> LOCATION: (5)..(7)
<223> OTHER INFORMATION: Xaa = Val, Leu, Ile, Met, Phe, Asn, Glu, Gln,
      His, Lys, Arg, Asp, Gly, Ala, Ser, Thr, Tyr, Trp, Cys or Pro
<220> FEATURE:
<221> NAME/KEY: VARIANT
<222> LOCATION: (8)..(8)
<223> OTHER INFORMATION: Xaa = Val, Leu, Ile, Met, Phe, Gly, Ala, Ser,
      Thr, Tyr, Trp, Cys or Pro
<220> FEATURE:
<221> NAME/KEY: VARIANT
<222> LOCATION: (9)..(9)
<223> OTHER INFORMATION: Xaa = Val, Leu, Ile, Met, Phe, Asn, Glu, Gln,
      His, Lys, Arg, Asp, Gly, Ala, Ser, Thr, Tyr, Trp, Cys or Pro
<220> FEATURE:
<221> NAME/KEY: VARIANT
<222> LOCATION: (10)..(10)
<223> OTHER INFORMATION: Xaa = Val, Leu, Ile, Met, Phe, Gly, Ala, Ser,
      Thr, Tyr, Trp, Cys or Pro
<220> FEATURE:
<221> NAME/KEY: VARIANT
<222> LOCATION: (11)..(11)
<223> OTHER INFORMATION: Xaa = Val, Leu, Ile, Met, Phe, Asn, Glu, Gln,
      His, Lys, Arg, Asp, Gly, Ala, Ser, Thr, Tyr, Trp, Cys or Pro
<220> FEATURE:
<221> NAME/KEY: VARIANT
<222> LOCATION: (12)..(12)
<223> OTHER INFORMATION: Xaa = Glu or Asp

<400> SEQUENCE: 183

Xaa Xaa Xaa Xaa Xaa Xaa Xaa Xaa Xaa Xaa Xaa Xaa
1               5                   10

<210> SEQ ID NO 184
<211> LENGTH: 12
<212> TYPE: PRT
<213> ORGANISM: Artificial Sequence
<220> FEATURE:
<223> OTHER INFORMATION: synthetic genetically encoded small illuminant
      (GESI) peptide
<220> FEATURE:
<221> NAME/KEY: VARIANT
<222> LOCATION: (1)..(2)
```

```
<223> OTHER INFORMATION: Xaa = Glu, Asp or absent
<220> FEATURE:
<221> NAME/KEY: VARIANT
<222> LOCATION: (3)..(10)
<223> OTHER INFORMATION: Xaa = Val, Leu, Ile, Met, Phe, Gly, Ala, Ser,
      Thr, Tyr, Trp, Cys or Pro
<220> FEATURE:
<221> NAME/KEY: VARIANT
<222> LOCATION: (12)..(12)
<223> OTHER INFORMATION: Xaa = Glu or Asp

<400> SEQUENCE: 184

Xaa Xaa Xaa Xaa Thr Gly Arg Xaa Ser Xaa Gly Xaa
 1               5                  10

<210> SEQ ID NO 185
<211> LENGTH: 12
<212> TYPE: PRT
<213> ORGANISM: Artificial Sequence
<220> FEATURE:
<223> OTHER INFORMATION: synthetic genetically encoded small illuminant
      (GESI) peptide
<220> FEATURE:
<221> NAME/KEY: VARIANT
<222> LOCATION: (1)..(5)
<223> OTHER INFORMATION: Xaa = Asp, Ala, Tyr or Trp, where at least one
      can be Asp and at least one can be Trp
<220> FEATURE:
<221> NAME/KEY: VARIANT
<222> LOCATION: (6)..(11)
<223> OTHER INFORMATION: Xaa = Val, Leu, Ile, Met, Phe, Asn, Glu, Gln,
      His, Lys, Arg, Asp, Gly, Ala, Ser, Thr, Tyr, Trp, Cys or Pro

<400> SEQUENCE: 185

Xaa Xaa Xaa Xaa Xaa Gly Xaa Xaa Xaa Xaa Xaa Glu
 1               5                  10

<210> SEQ ID NO 186
<211> LENGTH: 12
<212> TYPE: PRT
<213> ORGANISM: Artificial Sequence
<220> FEATURE:
<223> OTHER INFORMATION: synthetic genetically encoded small illuminant
      (GESI) peptide
<220> FEATURE:
<221> NAME/KEY: VARIANT
<222> LOCATION: (2)..(5)
<223> OTHER INFORMATION: Xaa = Asp, Ala, Tyr or Trp, where at least one
      can be Trp
<220> FEATURE:
<221> NAME/KEY: VARIANT
<222> LOCATION: (6)..(11)
<223> OTHER INFORMATION: Xaa = Val, Leu, Ile, Met, Phe, Asn, Glu, Gln,
      His, Lys, Arg, Asp, Gly, Ala, Ser, Thr, Tyr, Trp, Cys or Pro

<400> SEQUENCE: 186

Asp Xaa Xaa Xaa Xaa Gly Xaa Xaa Xaa Xaa Xaa Glu
 1               5                  10

<210> SEQ ID NO 187
<211> LENGTH: 19
<212> TYPE: PRT
<213> ORGANISM: Artificial Sequence
<220> FEATURE:
<223> OTHER INFORMATION: synthetic genetically encoded small illuminant
      (GESI) peptide
<220> FEATURE:
<221> NAME/KEY: PHOSPHORYLATION
<222> LOCATION: (3)..(3)
<223> OTHER INFORMATION: Tyr can be phosphorylated
<220> FEATURE:
<221> NAME/KEY: VARIANT
<222> LOCATION: (10)..(15)
```

-continued

```
<223> OTHER INFORMATION: Xaa = Val, Leu, Ile, Met, Phe, Asn, Glu, Gln,
      His, Lys, Arg, Asp, Gly, Ala, Ser, Thr, Tyr, Trp, Cys or Pro
<220> FEATURE:
<221> NAME/KEY: VARIANT
<222> LOCATION: (16)..(19)
<223> OTHER INFORMATION: Xaa = Val, Leu, Ile, Met, Phe, Asn, Glu, Gln,
      His, Lys, Arg, Asp, Gly, Ala, Ser, Thr, Tyr, Trp, Cys, Pro or
      absent

<400> SEQUENCE: 187

Tyr Ile Tyr Gly Ser Phe Lys Lys Lys Xaa Xaa Xaa Xaa Xaa Xaa Xaa
1               5                   10                  15

Xaa Xaa Xaa

<210> SEQ ID NO 188
<211> LENGTH: 19
<212> TYPE: PRT
<213> ORGANISM: Artificial Sequence
<220> FEATURE:
<223> OTHER INFORMATION: synthetic genetically encoded small illuminant
      (GESI) peptide
<220> FEATURE:
<221> NAME/KEY: PHOSPHORYLATION
<222> LOCATION: (4)..(4)
<223> OTHER INFORMATION: Tyr can be phosphorylated
<220> FEATURE:
<221> NAME/KEY: VARIANT
<222> LOCATION: (12)..(17)
<223> OTHER INFORMATION: Xaa = Val, Leu, Ile, Met, Phe, Asn, Glu, Gln,
      His, Lys, Arg, Asp, Gly, Ala, Ser, Thr, Tyr, Trp, Cys or Pro
<220> FEATURE:
<221> NAME/KEY: VARIANT
<222> LOCATION: (18)..(19)
<223> OTHER INFORMATION: Xaa = Val, Leu, Ile, Met, Phe, Asn, Glu, Gln,
      His, Lys, Arg, Asp, Gly, Ala, Ser, Thr, Tyr, Trp, Cys, Pro or
      absent

<400> SEQUENCE: 188

Glu Ala Ile Tyr Ala Ala Pro Phe Ala Lys Lys Xaa Xaa Xaa Xaa Xaa
1               5                   10                  15

Xaa Xaa Xaa

<210> SEQ ID NO 189
<211> LENGTH: 16
<212> TYPE: PRT
<213> ORGANISM: Artificial Sequence
<220> FEATURE:
<223> OTHER INFORMATION: synthetic genetically encoded small illuminant
      (GESI) peptide
<220> FEATURE:
<221> NAME/KEY: PHOSPHORYLATION
<222> LOCATION: (5)..(5)
<223> OTHER INFORMATION: Ser can be phosphorylated
<220> FEATURE:
<221> NAME/KEY: VARIANT
<222> LOCATION: (7)..(14)
<223> OTHER INFORMATION: Xaa = Val, Leu, Ile, Met, Phe, Asn, Glu, Gln,
      His, Lys, Arg, Asp, Gly, Ala, Ser, Thr, Tyr, Trp, Cys or Pro
<220> FEATURE:
<221> NAME/KEY: VARIANT
<222> LOCATION: (15)..(16)
<223> OTHER INFORMATION: Xaa = Val, Leu, Ile, Met, Phe, Asn, Glu, Gln,
      His, Lys, Arg, Asp, Gly, Ala, Ser, Thr, Tyr, Trp, Cys, Pro or
      absent

<400> SEQUENCE: 189

Leu Arg Arg Ala Ser Leu Xaa Xaa Xaa Xaa Xaa Xaa Xaa Xaa Xaa Xaa
1               5                   10                  15

<210> SEQ ID NO 190
<211> LENGTH: 15
```

```
<212> TYPE: PRT
<213> ORGANISM: Artificial Sequence
<220> FEATURE:
<223> OTHER INFORMATION: synthetic genetically encoded small illuminant
      (GESI) peptide

<400> SEQUENCE: 190

Tyr Ile Tyr Gly Ser Phe Lys Lys Lys Tyr Phe Gly Val His Ser
1               5                   10                  15

<210> SEQ ID NO 191
<211> LENGTH: 15
<212> TYPE: PRT
<213> ORGANISM: Artificial Sequence
<220> FEATURE:
<223> OTHER INFORMATION: synthetic genetically encoded small illuminant
      (GESI) peptide

<400> SEQUENCE: 191

Tyr Ile Tyr Gly Ser Phe Lys Lys Lys Glu Ser Val Tyr Ile Glu
1               5                   10                  15

<210> SEQ ID NO 192
<211> LENGTH: 16
<212> TYPE: PRT
<213> ORGANISM: Artificial Sequence
<220> FEATURE:
<223> OTHER INFORMATION: synthetic genetically encoded small illuminant
      (GESI) peptide

<400> SEQUENCE: 192

Tyr Ile Tyr Gly Ser Phe Lys Lys Lys Tyr Phe Asn Ala Ile Asn Thr
1               5                   10                  15

<210> SEQ ID NO 193
<211> LENGTH: 17
<212> TYPE: PRT
<213> ORGANISM: Artificial Sequence
<220> FEATURE:
<223> OTHER INFORMATION: synthetic genetically encoded small illuminant
      (GESI) peptide

<400> SEQUENCE: 193

Tyr Ile Tyr Gly Ser Phe Lys Lys Lys Asn Tyr His Tyr Glu Ile Glu
1               5                   10                  15

Tyr

<210> SEQ ID NO 194
<211> LENGTH: 17
<212> TYPE: PRT
<213> ORGANISM: Artificial Sequence
<220> FEATURE:
<223> OTHER INFORMATION: synthetic genetically encoded small illuminant
      (GESI) peptide

<400> SEQUENCE: 194

Tyr Ile Tyr Gly Ser Phe Lys Lys Lys Asn Tyr Thr Trp Tyr Val Ser
1               5                   10                  15

Tyr

<210> SEQ ID NO 195
<211> LENGTH: 17
<212> TYPE: PRT
<213> ORGANISM: Artificial Sequence
<220> FEATURE:
<223> OTHER INFORMATION: synthetic genetically encoded small illuminant
      (GESI) peptide
```

<400> SEQUENCE: 195

Tyr Ile Tyr Gly Ser Phe Lys Lys Lys Asp Gln Glu Phe Thr Ala Phe
1               5                   10                  15

Met

<210> SEQ ID NO 196
<211> LENGTH: 18
<212> TYPE: PRT
<213> ORGANISM: Artificial Sequence
<220> FEATURE:
<223> OTHER INFORMATION: synthetic genetically encoded small illuminant
      (GESI) peptide

<400> SEQUENCE: 196

Tyr Ile Tyr Gly Ser Phe Lys Lys Lys Asp Arg Met Phe Thr Thr Trp
1               5                   10                  15

Ser Asp

<210> SEQ ID NO 197
<211> LENGTH: 18
<212> TYPE: PRT
<213> ORGANISM: Artificial Sequence
<220> FEATURE:
<223> OTHER INFORMATION: synthetic genetically encoded small illuminant
      (GESI) peptide

<400> SEQUENCE: 197

Tyr Ile Tyr Gly Ser Phe Lys Lys Lys Phe Met Leu Trp Met Asp Glu
1               5                   10                  15

Thr Tyr

<210> SEQ ID NO 198
<211> LENGTH: 19
<212> TYPE: PRT
<213> ORGANISM: Artificial Sequence
<220> FEATURE:
<223> OTHER INFORMATION: synthetic genetically encoded small illuminant
      (GESI) peptide

<400> SEQUENCE: 198

Tyr Ile Tyr Gly Ser Phe Lys Lys Lys Phe Met Leu Trp Met Asp Glu
1               5                   10                  15

Thr Tyr Gly

<210> SEQ ID NO 199
<211> LENGTH: 17
<212> TYPE: PRT
<213> ORGANISM: Artificial Sequence
<220> FEATURE:
<223> OTHER INFORMATION: synthetic genetically encoded small illuminant
      (GESI) peptide

<400> SEQUENCE: 199

Glu Ala Ile Tyr Ala Ala Pro Phe Ala Lys Lys Tyr Thr Phe Glu Leu
1               5                   10                  15

Thr

<210> SEQ ID NO 200
<211> LENGTH: 19
<212> TYPE: PRT
<213> ORGANISM: Artificial Sequence
<220> FEATURE:
<223> OTHER INFORMATION: synthetic genetically encoded small illuminant -continued (GESI) peptide

<400> SEQUENCE: 200

Glu Ala Ile Tyr Ala Ala Pro Phe Ala Lys Lys Gly Tyr Trp Gly Trp
1               5                   10                  15

Phe Thr Phe

<210> SEQ ID NO 201
<211> LENGTH: 19
<212> TYPE: PRT
<213> ORGANISM: Artificial Sequence
<220> FEATURE:
<223> OTHER INFORMATION: synthetic genetically encoded small illuminant
      (GESI) peptide

<400> SEQUENCE: 201

Glu Ala Ile Tyr Ala Ala Pro Phe Ala Lys Lys Leu Tyr Ile Met Asp
1               5                   10                  15

Gly Trp Phe

<210> SEQ ID NO 202
<211> LENGTH: 16
<212> TYPE: PRT
<213> ORGANISM: Artificial Sequence
<220> FEATURE:
<223> OTHER INFORMATION: synthetic genetically encoded small illuminant
      (GESI) peptide

<400> SEQUENCE: 202

Leu Arg Arg Ala Ser Leu Pro Phe Met Met Leu Trp Leu Trp Ser Lys
1               5                   10                  15

<210> SEQ ID NO 203
<211> LENGTH: 15
<212> TYPE: PRT
<213> ORGANISM: Artificial Sequence
<220> FEATURE:
<223> OTHER INFORMATION: synthetic genetically encoded small illuminant
      (GESI) peptide

<400> SEQUENCE: 203

Leu Arg Arg Ala Ser Leu Arg Glu Ile Phe Val Ser Glu Trp Met
1               5                   10                  15

<210> SEQ ID NO 204
<211> LENGTH: 12
<212> TYPE: PRT
<213> ORGANISM: Artificial Sequence
<220> FEATURE:
<223> OTHER INFORMATION: synthetic genetically encoded small illuminant
      (GESI) peptide

<400> SEQUENCE: 204

Asp Ala Tyr Trp Asp Gly Thr Gly His Ile Tyr Glu
1               5                   10

<210> SEQ ID NO 205
<211> LENGTH: 6
<212> TYPE: PRT
<213> ORGANISM: Artificial Sequence
<220> FEATURE:
<223> OTHER INFORMATION: synthetic genetically encoded small illuminant
      (GESI) peptide
      OBOC library
<220> FEATURE:
<221> NAME/KEY: VARIANT
<222> LOCATION: (1)..(6)

```
<223> OTHER INFORMATION: Xaa = any amino acid
<220> FEATURE:
<221> NAME/KEY: MOD_RES
<222> LOCATION: (6)..(6)
<223> OTHER INFORMATION: Xaa affixed to polyethylene glycol grafted
      polystyrene bead

<400> SEQUENCE: 205

Xaa Xaa Xaa Xaa Xaa Xaa
1               5

<210> SEQ ID NO 206
<211> LENGTH: 21
<212> TYPE: PRT
<213> ORGANISM: Artificial Sequence
<220> FEATURE:
<223> OTHER INFORMATION: synthetic genetically encoded small illuminant
      (GESI) peptide histone H3 peptide fusion Library 1
<220> FEATURE:
<221> NAME/KEY: VARIANT
<222> LOCATION: (7)..(7)
<223> OTHER INFORMATION: Xaa = any natural amino acid except Cys
<220> FEATURE:
<221> NAME/KEY: VARIANT
<222> LOCATION: (8)..(16)
<223> OTHER INFORMATION: Xaa = any natural amino acid except Cys, may be
      present or absent

<400> SEQUENCE: 206

Arg Lys Ser Thr Thr Gly Xaa Xaa Xaa Xaa Xaa Xaa Xaa Xaa Xaa
1               5                   10                  15

Gly Lys Ala Pro Arg
            20

<210> SEQ ID NO 207
<211> LENGTH: 21
<212> TYPE: PRT
<213> ORGANISM: Artificial Sequence
<220> FEATURE:
<223> OTHER INFORMATION: synthetic genetically encoded small illuminant
      (GESI) peptide histone H3 peptide fusion Library 1
<220> FEATURE:
<221> NAME/KEY: PHOSPHORYLATION
<222> LOCATION: (3)..(3)
<223> OTHER INFORMATION: Ser can be phosphorylated or unphosphorylated
<220> FEATURE:
<221> NAME/KEY: VARIANT
<222> LOCATION: (7)..(7)
<223> OTHER INFORMATION: Xaa = any natural amino acid except Cys
<220> FEATURE:
<221> NAME/KEY: VARIANT
<222> LOCATION: (8)..(16)
<223> OTHER INFORMATION: Xaa = any natural amino acid except Cys, may be
      present or absent

<400> SEQUENCE: 207

Arg Lys Ser Thr Thr Gly Xaa Xaa Xaa Xaa Xaa Xaa Xaa Xaa Xaa
1               5                   10                  15

Gly Lys Ala Pro Arg
            20

<210> SEQ ID NO 208
<211> LENGTH: 21
<212> TYPE: PRT
<213> ORGANISM: Artificial Sequence
<220> FEATURE:
<223> OTHER INFORMATION: synthetic genetically encoded small illuminant
      (GESI) peptide histone H3 peptide fusion Library 1
<220> FEATURE:
<221> NAME/KEY: VARIANT
<222> LOCATION: (7)..(7)
```

-continued

<223> OTHER INFORMATION: Xaa = any natural amino acid except Cys
<220> FEATURE:
<221> NAME/KEY: VARIANT
<222> LOCATION: (8)..(16)
<223> OTHER INFORMATION: Xaa = any natural amino acid except Cys, may be
      present or absent
<220> FEATURE:
<221> NAME/KEY: ACETYLATION
<222> LOCATION: (18)..(18)
<223> OTHER INFORMATION: Lys can be acetylated

<400> SEQUENCE: 208

Arg Lys Ser Thr Thr Gly Xaa Xaa Xaa Xaa Xaa Xaa Xaa Xaa Xaa Xaa
1               5                   10                  15

Gly Lys Ala Pro Arg
            20

<210> SEQ ID NO 209
<211> LENGTH: 21
<212> TYPE: PRT
<213> ORGANISM: Artificial Sequence
<220> FEATURE:
<223> OTHER INFORMATION: synthetic genetically encoded small illuminant
      (GESI) peptide histone H3 peptide fusion Library 1
<220> FEATURE:
<221> NAME/KEY: ACETYLATION
<222> LOCATION: (2)..(2)
<223> OTHER INFORMATION: Lys can be acetylated
<220> FEATURE:
<221> NAME/KEY: VARIANT
<222> LOCATION: (7)..(7)
<223> OTHER INFORMATION: Xaa = any natural amino acid except Cys
<220> FEATURE:
<221> NAME/KEY: VARIANT
<222> LOCATION: (8)..(16)
<223> OTHER INFORMATION: Xaa = any natural amino acid except Cys, may be
      present or absent

<400> SEQUENCE: 209

Arg Lys Ser Thr Thr Gly Xaa Xaa Xaa Xaa Xaa Xaa Xaa Xaa Xaa Xaa
1               5                   10                  15

Gly Lys Ala Pro Arg
            20

<210> SEQ ID NO 210
<211> LENGTH: 21
<212> TYPE: PRT
<213> ORGANISM: Artificial Sequence
<220> FEATURE:
<223> OTHER INFORMATION: synthetic genetically encoded small illuminant
      (GESI) peptide histone H3 peptide fusion Library 1
<220> FEATURE:
<221> NAME/KEY: PHOSPHORYLATION
<222> LOCATION: (3)..(3)
<223> OTHER INFORMATION: Ser can be phosphorylated
<220> FEATURE:
<221> NAME/KEY: VARIANT
<222> LOCATION: (7)..(7)
<223> OTHER INFORMATION: Xaa = any natural amino acid except Cys
<220> FEATURE:
<221> NAME/KEY: VARIANT
<222> LOCATION: (8)..(16)
<223> OTHER INFORMATION: Xaa = any natural amino acid except Cys, may be
      present or absent
<220> FEATURE:
<221> NAME/KEY: ACETYLATION
<222> LOCATION: (18)..(18)
<223> OTHER INFORMATION: Lys can be acetylated

<400> SEQUENCE: 210

Arg Lys Ser Thr Thr Gly Xaa Xaa Xaa Xaa Xaa Xaa Xaa Xaa Xaa Xaa
1               5                   10                  15

Gly Lys Ala Pro Arg
            20

<210> SEQ ID NO 211
<211> LENGTH: 21
<212> TYPE: PRT
<213> ORGANISM: Artificial Sequence
<220> FEATURE:
<223> OTHER INFORMATION: synthetic genetically encoded small illuminant
      (GESI) peptide histone H3 peptide fusion Library 1
<220> FEATURE:
<221> NAME/KEY: ACETYLATION
<222> LOCATION: (2)..(2)
<223> OTHER INFORMATION: Lys can be acetylated
<220> FEATURE:
<221> NAME/KEY: PHOSPHORYLATION
<222> LOCATION: (3)..(3)
<223> OTHER INFORMATION: Ser can be phosphorylated
<220> FEATURE:
<221> NAME/KEY: VARIANT
<222> LOCATION: (7)..(7)
<223> OTHER INFORMATION: Xaa = any natural amino acid except Cys
<220> FEATURE:
<221> NAME/KEY: VARIANT
<222> LOCATION: (8)..(16)
<223> OTHER INFORMATION: Xaa = any natural amino acid except Cys, may be
      present or absent

<400> SEQUENCE: 211

Arg Lys Ser Thr Thr Gly Xaa Xaa Xaa Xaa Xaa Xaa Xaa Xaa Xaa
1               5                  10                  15

Gly Lys Ala Pro Arg
            20

<210> SEQ ID NO 212
<211> LENGTH: 12
<212> TYPE: PRT
<213> ORGANISM: Artificial Sequence
<220> FEATURE:
<223> OTHER INFORMATION: synthetic genetically encoded small illuminant
      (GESI) peptide
<220> FEATURE:
<221> NAME/KEY: VARIANT
<222> LOCATION: (1)..(2)
<223> OTHER INFORMATION: Xaa = Asp or absent
<220> FEATURE:
<221> NAME/KEY: VARIANT
<222> LOCATION: (3)..(4)
<223> OTHER INFORMATION: Xaa = Val, Leu, Ile, Met, Phe, Gly, Ala, Ser,
      Thr, Tyr, Trp, Cys or Pro
<220> FEATURE:
<221> NAME/KEY: VARIANT
<222> LOCATION: (5)..(7)
<223> OTHER INFORMATION: Xaa = Val, Leu, Ile, Met, Phe, Asn, Glu, Gln,
      His, Lys, Arg, Asp, Gly, Ala, Ser, Thr, Tyr, Trp, Cys or Pro
<220> FEATURE:
<221> NAME/KEY: VARIANT
<222> LOCATION: (8)..(8)
<223> OTHER INFORMATION: Xaa = Val, Leu, Ile, Met, Phe, Gly, Ala, Ser,
      Thr, Tyr, Trp, Cys or Pro
<220> FEATURE:
<221> NAME/KEY: VARIANT
<222> LOCATION: (9)..(9)
<223> OTHER INFORMATION: Xaa = Val, Leu, Ile, Met, Phe, Asn, Glu, Gln,
      His, Lys, Arg, Asp, Gly, Ala, Ser, Thr, Tyr, Trp, Cys or Pro
<220> FEATURE:
<221> NAME/KEY: VARIANT
<222> LOCATION: (10)..(10)
<223> OTHER INFORMATION: Xaa = Val, Leu, Ile, Met, Phe, Gly, Ala, Ser,
      Thr, Tyr, Trp, Cys or Pro
<220> FEATURE:
<221> NAME/KEY: VARIANT
<222> LOCATION: (11)..(11)
<223> OTHER INFORMATION: Xaa = Val, Leu, Ile, Met, Phe, Asn, Glu, Gln, His, Lys, Arg, Asp, Gly, Ala, Ser, Thr, Tyr, Trp, Cys or Pro

<400> SEQUENCE: 212

Xaa Xaa Xaa Xaa Xaa Xaa Xaa Xaa Xaa Xaa Xaa Glu
1               5                   10

<210> SEQ ID NO 213
<211> LENGTH: 12
<212> TYPE: PRT
<213> ORGANISM: Artificial Sequence
<220> FEATURE:
<223> OTHER INFORMATION: synthetic genetically encoded small illuminant
      (GESI) peptide
<220> FEATURE:
<221> NAME/KEY: VARIANT
<222> LOCATION: (1)..(5)
<223> OTHER INFORMATION: Xaa = Asn, Glu, Gln, His, Lys, Arg, Ala, Asp,
      Tyr, Trp or Pro
<220> FEATURE:
<221> NAME/KEY: VARIANT
<222> LOCATION: (6)..(11)
<223> OTHER INFORMATION: Xaa = Val, Leu, Ile, Met, Phe, Asn, Glu, Gln,
      His, Lys, Arg, Asp, Gly, Ala, Ser, Thr, Tyr, Trp, Cys or Pro
<220> FEATURE:
<221> NAME/KEY: VARIANT
<222> LOCATION: (12)..(12)
<223> OTHER INFORMATION: Xaa = Asp or Glu

<400> SEQUENCE: 213

Xaa Xaa Xaa Xaa Xaa Xaa Xaa Xaa Xaa Xaa Xaa Xaa
1               5                   10

<210> SEQ ID NO 214
<211> LENGTH: 5
<212> TYPE: PRT
<213> ORGANISM: Artificial Sequence
<220> FEATURE:
<223> OTHER INFORMATION: synthetic H3 histone tail

<400> SEQUENCE: 214

Arg Lys Ser Thr Gly
1               5

<210> SEQ ID NO 215
<211> LENGTH: 5
<212> TYPE: PRT
<213> ORGANISM: Artificial Sequence
<220> FEATURE:
<223> OTHER INFORMATION: synthetic H3 histone tail

<400> SEQUENCE: 215

Gly Lys Ala Pro Arg
1               5

<210> SEQ ID NO 216
<211> LENGTH: 18
<212> TYPE: PRT
<213> ORGANISM: Artificial Sequence
<220> FEATURE:
<223> OTHER INFORMATION: synthetic genetically encoded small illuminant
      (GESI) peptide library substrate for c-src protein tyrosine kinase
<220> FEATURE:
<221> NAME/KEY: PHOSPHORYLATION
<222> LOCATION: (3)..(3)
<223> OTHER INFORMATION: Tyr can be phosphorylated
<220> FEATURE:
<221> NAME/KEY: VARIANT
<222> LOCATION: (10)..(15)
<223> OTHER INFORMATION: Xaa = any natural amino acid except Cys
<220> FEATURE:
<221> NAME/KEY: VARIANT

```
<222> LOCATION: (16)..(18)
<223> OTHER INFORMATION: Xaa = any natural amino acid except Cys, may be
      present or absent

<400> SEQUENCE: 216

Tyr Ile Tyr Gly Ser Phe Lys Lys Lys Xaa Xaa Xaa Xaa Xaa Xaa Xaa
1               5                   10                  15

Xaa Xaa

<210> SEQ ID NO 217
<211> LENGTH: 20
<212> TYPE: PRT
<213> ORGANISM: Artificial Sequence
<220> FEATURE:
<223> OTHER INFORMATION: synthetic genetically encoded small illuminant
      (GESI) peptide library c-abl motif (Abltide)
<220> FEATURE:
<221> NAME/KEY: PHOSPHORYLATION
<222> LOCATION: (4)..(4)
<223> OTHER INFORMATION: Tyr can be phosphorylated
<220> FEATURE:
<221> NAME/KEY: VARIANT
<222> LOCATION: (12)..(17)
<223> OTHER INFORMATION: Xaa = any natural amino acid except Cys
<220> FEATURE:
<221> NAME/KEY: VARIANT
<222> LOCATION: (18)..(20)
<223> OTHER INFORMATION: Xaa = any natural amino acid except Cys, may be
      present or absent

<400> SEQUENCE: 217

Glu Ala Ile Tyr Ala Ala Pro Phe Ala Lys Lys Xaa Xaa Xaa Xaa Xaa
1               5                   10                  15

Xaa Xaa Xaa Xaa
            20

<210> SEQ ID NO 218
<211> LENGTH: 15
<212> TYPE: PRT
<213> ORGANISM: Artificial Sequence
<220> FEATURE:
<223> OTHER INFORMATION: synthetic genetically encoded small illuminant
      (GESI) peptide reporter X6-3 for c-src protein tyrosine kinase
<220> FEATURE:
<221> NAME/KEY: PHOSPHORYLATION
<222> LOCATION: (3)..(3)
<223> OTHER INFORMATION: Tyr can be phosphorylated

<400> SEQUENCE: 218

Tyr Ile Tyr Gly Ser Phe Lys Lys Lys Glu Gln Tyr Tyr Gln Trp
1               5                   10                  15

<210> SEQ ID NO 219
<211> LENGTH: 16
<212> TYPE: PRT
<213> ORGANISM: Artificial Sequence
<220> FEATURE:
<223> OTHER INFORMATION: synthetic genetically encoded small illuminant
      (GESI) peptide reporter X7-1 for c-src protein tyrosine kinase
<220> FEATURE:
<221> NAME/KEY: PHOSPHORYLATION
<222> LOCATION: (3)..(3)
<223> OTHER INFORMATION: Tyr can be phosphorylated

<400> SEQUENCE: 219

Tyr Ile Tyr Gly Ser Phe Lys Lys Lys Asp Tyr Val Phe Ala Leu Tyr
1               5                   10                  15

<210> SEQ ID NO 220
```

```
<211> LENGTH: 17
<212> TYPE: PRT
<213> ORGANISM: Artificial Sequence
<220> FEATURE:
<223> OTHER INFORMATION: synthetic genetically encoded small illuminant
      (GESI) peptide reporter X8-1 for c-src protein tyrosine kinase
<220> FEATURE:
<221> NAME/KEY: PHOSPHORYLATION
<222> LOCATION: (3)..(3)
<223> OTHER INFORMATION: Tyr can be phosphorylated

<400> SEQUENCE: 220

Tyr Ile Tyr Gly Ser Phe Lys Lys Lys Ile Phe Thr Gln Asn Ile Tyr
1               5                   10                  15
Ile

<210> SEQ ID NO 221
<211> LENGTH: 17
<212> TYPE: PRT
<213> ORGANISM: Artificial Sequence
<220> FEATURE:
<223> OTHER INFORMATION: synthetic genetically encoded small illuminant
      (GESI) peptide reporter X8-3 for c-src protein tyrosine kinase

<400> SEQUENCE: 221

Tyr Ile Tyr Gly Ser Phe Lys Lys Lys Asp Gln Glu Phe Thr Ala Phe
1               5                   10                  15
Met

<210> SEQ ID NO 222
<211> LENGTH: 9
<212> TYPE: PRT
<213> ORGANISM: Artificial Sequence
<220> FEATURE:
<223> OTHER INFORMATION: synthetic peptide substrate for protein
      tyrosine kinase c-src
<220> FEATURE:
<221> NAME/KEY: PHOSPHORYLATION
<222> LOCATION: (3)..(3)
<223> OTHER INFORMATION: Tyr can be phosphorylated

<400> SEQUENCE: 222

Tyr Ile Tyr Gly Ser Phe Lys Lys Lys
1               5

<210> SEQ ID NO 223
<211> LENGTH: 4
<212> TYPE: PRT
<213> ORGANISM: Artificial Sequence
<220> FEATURE:
<223> OTHER INFORMATION: synthetic protein kinase A (PKA) substrate
      motif
<220> FEATURE:
<221> NAME/KEY: VARIANT
<222> LOCATION: (3)..(3)
<223> OTHER INFORMATION: Xaa = any amino acid
<220> FEATURE:
<221> NAME/KEY: VARIANT
<222> LOCATION: (4)..(4)
<223> OTHER INFORMATION: Xaa = Ser or Thr

<400> SEQUENCE: 223

Arg Arg Xaa Xaa
1

<210> SEQ ID NO 224
<211> LENGTH: 19
<212> TYPE: PRT
<213> ORGANISM: Artificial Sequence
```

-continued

```
<220> FEATURE:
<223> OTHER INFORMATION: synthetic genetically encoded small illuminant
      (GESI) peptide LLT1
<220> FEATURE:
<221> NAME/KEY: PHOSPHORYLATION
<222> LOCATION: (4)..(4)
<223> OTHER INFORMATION: Tyr can be phosphorylated

<400> SEQUENCE: 224

Glu Ala Ile Tyr Ala Ala Pro Phe Ala Lys Lys Tyr Tyr Val Tyr Asp
1               5                   10                  15

Met His Ile

<210> SEQ ID NO 225
<211> LENGTH: 19
<212> TYPE: PRT
<213> ORGANISM: Artificial Sequence
<220> FEATURE:
<223> OTHER INFORMATION: synthetic genetically encoded small illuminant
      (GESI) peptide LLT2
<220> FEATURE:
<221> NAME/KEY: PHOSPHORYLATION
<222> LOCATION: (4)..(4)
<223> OTHER INFORMATION: Tyr can be phosphorylated

<400> SEQUENCE: 225

Glu Ala Ile Tyr Ala Ala Pro Phe Ala Lys Lys Tyr Tyr Val Gln Asp
1               5                   10                  15

Ser Arg Ala

<210> SEQ ID NO 226
<211> LENGTH: 19
<212> TYPE: PRT
<213> ORGANISM: Artificial Sequence
<220> FEATURE:
<223> OTHER INFORMATION: synthetic genetically encoded small illuminant
      (GESI) peptide LLT3
<220> FEATURE:
<221> NAME/KEY: PHOSPHORYLATION
<222> LOCATION: (4)..(4)
<223> OTHER INFORMATION: Tyr can be phosphorylated

<400> SEQUENCE: 226

Glu Ala Ile Tyr Ala Ala Pro Phe Ala Lys Lys Tyr Tyr Val Ser Glu
1               5                   10                  15

Arg Lys Trp

<210> SEQ ID NO 227
<211> LENGTH: 15
<212> TYPE: PRT
<213> ORGANISM: Artificial Sequence
<220> FEATURE:
<223> OTHER INFORMATION: synthetic genetically encoded small illuminant
      (GESI) peptide activator of malachite green (MG)

<400> SEQUENCE: 227

Leu Arg Arg Ala Ser Leu Phe Tyr Gly Met Trp Tyr Pro Ser Thr
1               5                   10                  15

<210> SEQ ID NO 228
<211> LENGTH: 20
<212> TYPE: PRT
<213> ORGANISM: Artificial Sequence
<220> FEATURE:
<223> OTHER INFORMATION: synthetic genetically encoded small illuminant
      (GESI) OBOC library
<220> FEATURE:
<221> NAME/KEY: METHYLATION
```

```
<222> LOCATION: (2)..(2)
<223> OTHER INFORMATION: Lys can be methylated
<220> FEATURE:
<221> NAME/KEY: PHOSPHORYLATION
<222> LOCATION: (3)..(3)
<223> OTHER INFORMATION: Ser can be phosphorylated
<220> FEATURE:
<221> NAME/KEY: VARIANT
<222> LOCATION: (7)..(7)
<223> OTHER INFORMATION: Xaa = any amino acid
<220> FEATURE:
<221> NAME/KEY: VARIANT
<222> LOCATION: (8)..(16)
<223> OTHER INFORMATION: Xaa = any amino acid, may be present or absent
<220> FEATURE:
<221> NAME/KEY: ACETYLATION
<222> LOCATION: (18)..(18)
<223> OTHER INFORMATION: Lys can be acetylated
<220> FEATURE:
<221> NAME/KEY: MOD_RES
<222> LOCATION: (20)..(20)
<223> OTHER INFORMATION: Pro affixed to polyethylene glycol grafted
      polystyrene bead

<400> SEQUENCE: 228

Arg Lys Ser Thr Thr Gly Xaa Xaa Xaa Xaa Xaa Xaa Xaa Xaa Xaa Xaa
1               5                   10                  15

Gly Lys Ala Pro
            20
```

FUNCTIONAL ILLUMINATION IN LIVING CELLS

CROSS-REFERENCES TO RELATED APPLICATIONS

This application is the U.S. National Stage Entry under § 371 of International Application No. PCT/US2014/031824, filed Mar. 26, 2014, which claims priority to U.S. Provisional Application No. 61/837,392, filed Jun. 20, 2013, and U.S. Provisional Application No. 61/805,320, filed Mar. 26, 2013, each which is incorporated in its entirety herein for all purposes.

STATEMENT AS TO RIGHTS TO INVENTIONS MADE UNDER FEDERALLY SPONSORED RESEARCH AND DEVELOPMENT

Not Applicable

BACKGROUND OF THE INVENTION

In the last decade, application of genetically encoded fluorescent probes and sensors in molecular imaging has greatly improved our understanding about how specific molecules orchestrate cellular functions and how errant cells cause diseases. Green fluorescent protein and its related fluorescent proteins (FPs) have been successfully employed in a broad range of biological disciplines, reporting the distribution, abundance, dynamics, interaction and conformational changes of essential signaling molecules in time and space by engineering FP chimeras. However, engineering FP chimeras has long been limited by the large size (27 kDa) and biophysical properties of FPs, which can interfere with the evolved function of host proteins. Most importantly, FPs have proven to be difficult to use as sensors for probing complex biochemical processes with desired signal-to-noise ratio, such as protein phosphorylation and histone modifications. Besides FPs, small molecule based fluorophores are also useful tools for molecular imaging, but not for living cell imaging due to their lack of the cellular specificity. To date, several site-specific chemical labeling systems have been developed to detect proteins in living cells by targeting small molecular based fluorophores to peptides motifs or single-chain antibody (scFv). Though direct evolution efforts have tuned the binding affinity and specificity of small molecular fluorophores to peptide motifs, existing systems lack of the cellular specificity and have limitations as biosensors to report the functions of signaling molecules. Despite current advances in molecular imaging, tools are still lacking to allow multiplex imaging of the activity dynamics of multiple functional proteins or signaling pathways.

Therefore, a need exists for an improved chemical labeling system for molecular imaging that allows for monitoring of proteins of interest in a variety of biochemical processes and pathways. Surprisingly, the present invention satisfies this need and provides related advantages as well.

BRIEF SUMMARY OF THE INVENTION

In one aspect, the present invention provides a method of detecting a peptide. The method comprises contacting the peptide with a dye such that the peptide specifically binds to the dye changing the fluorescence properties of the dye, wherein the peptide comprises from about 5 to about 100 amino acids; and detecting the change in fluorescence properties of the dye, thereby detecting the peptide.

In another aspect, the present invention provides an expression construct comprising a polynucleotide encoding a fusion protein. The polynucleotide comprises a first polynucleotide encoding peptide of about 5 to 100 amino acids in length, wherein direct binding of the peptide tag to a dye to form a complex changes the fluorescence of the dye; and a second polynucleotide encoding a protein, wherein the second polynucleotide is fused to the first polynucleotide, thereby encoding a fusion protein.

In yet another aspect, the present invention provides a method for identifying a peptide of about 5 to 100 amino acids in length that specifically binds a dye, wherein binding of the peptide to the dye changes the fluorescence of the dye. The method comprises: (a) contacting a one-bead-one-compound combinatorial peptide library with an organic dye to form a complex between the peptide and the dye, wherein the library comprises multiple beads with synthetic peptides attached thereto; (b) detecting fluorescence emitting from the complex; and (c) determining the amino acid sequence of the peptide of the complex, thereby identifying the peptide bound to the dye.

BRIEF DESCRIPTION OF THE FIGURES

FIGS. 1A, 1B, 1C and 1D provide examples of triarylmethane dyes (A), cyanine dyes (B), benzylidene imidazolinone dyes (C) and indigo dyes (D).

FIGS. 2A, B, and C represent three different areas of the array. FIGS. 2A (iii), 2B (iii) and 2C (iii) correspond to the areas in FIGS. 2A, B, and C, respectively after bromocresol purple incubation. Among total 11 beads with characteristic binding profile, #1, #3, #6, #8 and #11 beads only bind to malachite green. #4, #5 and #9 beads only bind to bromocresol purple. #2, #7 and #10 beads bind to both indigo carmine and bromocresol purple.

FIG. 8A shows the fluorescence titration curve for the binding of MG to peptide 12 in solution. FIG. 8B shows the simulated structure of the peptide 12-MG complex.

FIGS. 11A and 11B illustrate the fluorescence activity of MG upon binding to peptide 2 on a bead. FIG. 11A shows fluorescence titration curves for binding of MG to peptide 2 on a bead. FIG. 11B shows simulated structures of the peptide 2-MG complex in the absence or presence of calcium.

FIG. 12 shows circular dichroism (CD) spectrum of peptide 2 and peptide 12 in the presence of Chelex.

FIG. 13 shows the differences in fluorescent intensity detected in the alanine walk (FIG. 13A) and truncation (FIG. 13B) studies for peptide 2. Peptide 2 variants of the alanine walk experiment include peptides having amino acid sequences set forth in SEQ ID NOS:109-121. Peptide 2 deletions include peptides having the amino acid sequences set forth in SEQ ID NOS:122-139.

FIG. 15A shows fluorescence of cells expressing recombinant mCerulean. FIG. 15B shows fluorescence of cells expressing recombinant mCerulean-GESI and incubated with MG. FIG. 15C shows fluorescence of cells expressing recombinant mCerulean-GESI with a nuclear localization signal (NLS-mCerulean-GESI) and exposed to MG. FIG. 15D shows fluorescence of cells expressing recombinant mCerulean-GESI cells treated with acetylcholine (Ach), and shows in the graph relative fluorescence intensity with aceylcholine (+Ach) or without acetylcholine (−Ach).

FIG. 17A depicts the linear peptide library L-1 (XXYIYGS-FKXXXXC, wherein the second Y residue can be phosphorylated (SEQ ID NO:140) and XXYIYGSFKXXXXCY, wherein the second Y residue can be phosphorylated (SEQ ID NO:141)). FIG. 17B depicts the cyclic peptide library L-2 (SEQ ID NO:140 and CXXYIYGSFKXXXXCY, wherein the second Y residue can be phosphorylated (SEQ ID NO:142)). FIG. 17C depicts the linear peptide library L-3 (XXRRXSXXXXC, wherein the serine residue can be phosphorylated (SEQ ID NO:143) and XXRRXSXXXXCY, wherein the serine residue can be phosphorylated (SEQ ID NO:144). FIG. 17D depicts the cyclic peptide library L-4 (CXXRRXSXXXXC, wherein the serine residue can be phosphorylated (SEQ ID NO:145) and CXXRRX-SXXXXCY, wherein the serine residue can be phosphorylated (SEQ ID NO:146).

FIG. 18 shows exemplary designs of one-bead-one-compound (OBOC) libraries and various screening approaches. The table depicts peptides having an amino acid sequence set forth in SEQ ID NOS: 147-153, 205 and 228 attached to beads.

FIG. 19 shows exemplary embodiments of genetically encoded small illuminant (GESI) fusion proteins for probing protein kinase activity. The peptides have an amino acid sequence set forth in SEQ ID NOS: 72 and 73.

FIGS. 20A, 20B, 20C, 20D, and 20E illustrate the library screening method and the design of genetically encoded small fluorescent illuminants for probing histone epigenetics. FIG. 20A shows structure of 3,5-dimethoxy-4-hydroxybenzylidene imidazolinone (DMHBI). FIG. 20B shows the fluorescence from a peptide-OBOC library saturated with DMHBI. The peptides of the library have an amino acid sequence set forth in SEQ ID NO:74. FIG. 20C shows schematic of histone 2 (H2)-peptide fusion library. The sequences=of the peptide is set forth in SEQ ID NO: 75). FIG. 20D shows positive peptide bead with DMHBI fluorescence. Scale bar: 100 μm. FIG. 20E shows the design of histone 3 (H3)-peptide fusion library. The sequences of the peptides are set forth in SEQ ID NOS: 76, 206-211, 77 and 78 and the tables.

DETAILED DESCRIPTION OF THE INVENTION

I. Introduction

Figure 2:
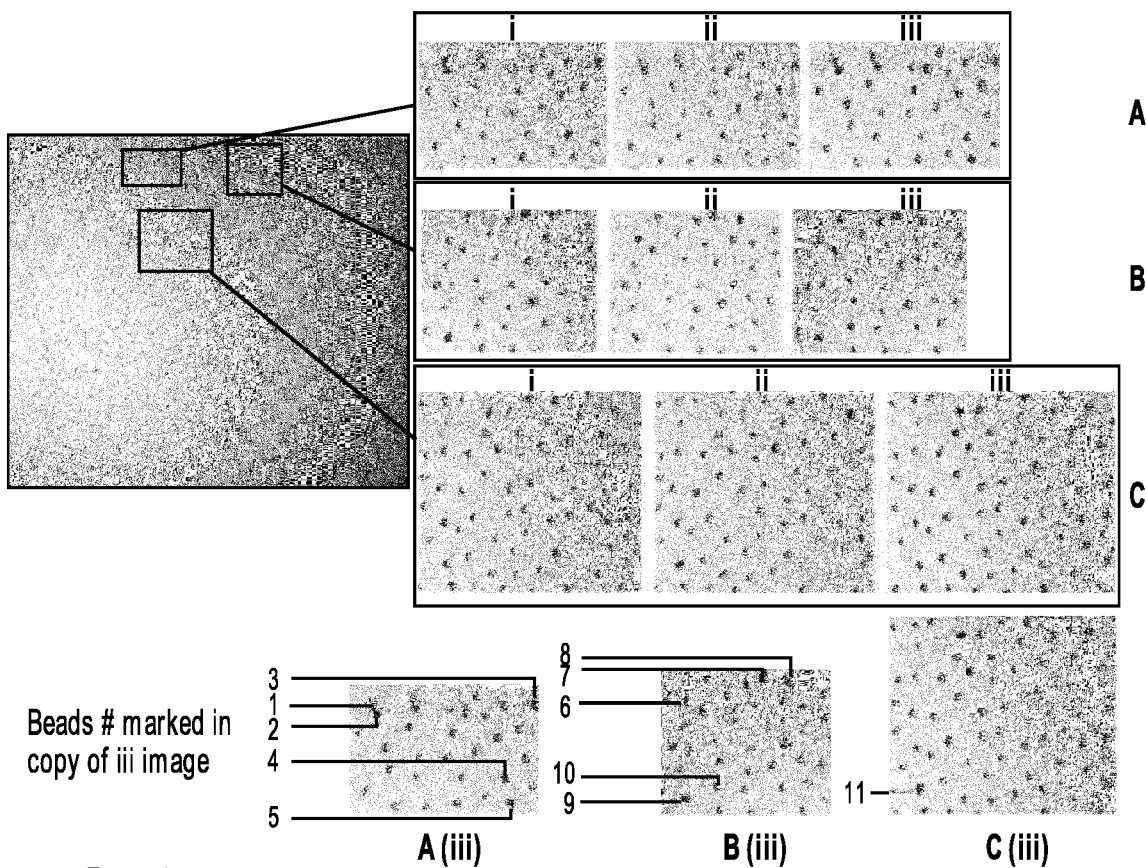
FIG. 2 illustrates a polydimethylsiloxane (PDMS) affixed bead array. The array was incubated with three different dyes sequentially. Beads were incubated with indigo carmine (i) till the color was saturated, and then the dye was washed away completely and incubated with the second dye malachite green (ii). The third dye bromocresol purple (iii) was last incubated after malachite green was removed.

Technology development in two areas has defined what is possible in molecular imaging in living cells. First, advances in optical microscopy, including wide-field and confocal fluorescent microscopy, multi-photon microscopy, and super resolution microscopy have made it possible to visualize the structure and function of living cells and organisms with micrometer to nanometer resolution. Second, a variety of biochemical and imaging tools have been developed to study the molecular mechanisms of cellular networks. For example, gene expression and protein localization and trafficking are routinely studied by genetic fusion of the target to a reporter, such as a GFP and its relatives, or to peptide tags that binds exogenous fluorophores (van Roessel et al., *Nat. Cell Biol.*, 4:E15-20 (2002)). In other instances, antibodies raised against a target protein are conjugated with small molecular fluorophores and are used for profile protein expression patterns, protein states such as phosphorylation, and macro-molecular complexes (Mandell, J W., *Am. J. Pathol.*, 163:1687-1698 (2003)). Most importantly, fluorescent probes have been adapted to biosensors via protein engineering for allowing noninvasive monitoring of a variety of essential signaling molecules (such as $Ca^{2+}$, $Cl^-$, $Zn^{2+}$), enzyme activity and cellular events, neural transmitters, protein kinases (PK) and membrane potential. Biosensor molecules can be applied to cultured cells or injected into animals via a transgene, which allows defined cell populations by promoters and enhancers, conditional expression, and sub-cellular targeting with signal peptides and retention sequences. Genetically encoded sensors typically employ either a single fluorescent protein or a Förster resonance energy transfer (FRET) pair of donor and acceptor FPs as a reporter element. Genetically encoded biosensors have greatly advanced our ability to understand the complex physiology of cellular signaling with exquisite spatial and temporal resolutions in live cells (for reviews, see Tian et al., *Drug Discov. Today Dis. Models*, 5:27-35 (2008); Palmer et al., *Trends Biotechnol.*, 29:144-52 (2011); Miyawaki, A., *Nat. Rev. Mol. Cell. Biol.*, 12:656-668 (2011)). Although powerful, these probes are limited by their large size (and thus potential to interfere with the structure and/or function of the proteins to which they are fused) and reliance on optical forms of readout.

Alternatively, a few chemical labeling systems have been developed to facilitate targeting small-molecule fluorophores with great specificity to biological molecules or compartments of interest in live cells (Fernandez-Suarez, M and Ting, A Y, *Nat. Rev. Mol. Cell Biol.*, 9:929-943 (2008)). Chemical labeling systems employ special nucleic acid sequences, peptide or protein tags that are capable of binding to small-molecule fluorophore, either directly or via enzyme reaction. In some cases, direct binding can lead to large enhancements of fluorescence. For example, in the biarsenical system, binding of FlAsH and ReAsH fluorogens to a tetracysteine motif leads to the increased respective green and red fluorescence (Martin et al., *Nat. Biotechnol.*, 23:1308-14 (2005)). The infrared fluorescence of triphenylmethane dyes, such as MG, can be increased 500-1000 fold upon binding to RNA-aptamer or single-chain antibodies (scFvs) (Babendure et al., *J. Am. Chem. Soc.*, 125:16-7 (2003); Szent-Gyorgyi et al., Nat. Biotechnol., 26:235-40 (2008)). Such fluorescent activating proteins (FAPs) have also been created for thiazole orange (TO) and cyanine dyes (Ozhalici-Unal et al., *J. Am. Chem. Soc.*, 130:12620-12621 (2008)). These scFv-based FAPs can be fused to essential proteins to report their localization and trafficking in living cells. However, the size of scFvs is similar to that of GFP, thus posing the possibility of influencing the evolved function of fused proteins. In addition, existing systems have limitations to be adapted to biosensors revealing the functional information of signaling molecules.

The peptides provided herein can be used as tags for optical probing the dynamics of selected proteins of interest in subcellular locations in living cells and whole animals. Also, they can function as sensors for the optical detection of post-translational protein modifications, such as protein phosphorylation and histone modifications in living cells. In some embodiments, the peptide can have at least one post-translational modification.

The peptide of the present invention can also include a targeting moiety. Any suitable targeting moiety can be used, such as, but not limited to, an antibody, antibody fragment, peptide aptamer, viral protein, virus particle, or variant thereof. In some embodiments, the targeting moiety can be an antibody, antibody fragment, peptide aptamer, ion channel, membrane receptor, or variant thereof. The antibody can be any suitable antibody, such as a monoclonal antibody. In some embodiments, the targeting moiety can be a viral protein. In some embodiments, the targeting moiety can be an ion channel or a membrane receptor.

The present invention provides peptides that can bind to a broad color spectrum of organic dyes including those in the infrared range. The present invention provides an expanded catalogue of fluorescence imaging tools with versatility to be broadly applicable across many fields of biology.

II. Definitions

The term "peptide" as used herein, refers to a polymer of about 3 to 200 amino acid residues that may not have a natural biological function. It can be a derivative of or a fragment of a protein or polypeptide.

The term "protein" or "polypeptide" refers to a polymer of amino acid residues. The term applies to amino acid polymers in which one or more amino acid residue is an artificial chemical mimetic of a corresponding naturally occurring amino acid, as well as to naturally occurring amino acid polymers and non-naturally occurring amino acid polymers. As used herein, the term encompasses amino acid chains of any length, including full-length proteins, wherein the amino acid residues are linked by covalent peptide bonds. The term "fusion protein" as used herein refers to chimeric protein comprising a polypeptide or a fragment thereof and a peptide that is fused to the polypeptide. In some instance, the fusion protein is generated by joining two more genes which originally encode two separate peptides, proteins or combinations thereof.

The term "amino acid" refers to refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. For the purposes of this application, amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. For the purposes of this application, amino acid mimetics refers to chemical compounds that have a structure that is different from the general chemical structure of an amino acid, but that functions in a manner similar to a naturally occurring amino acid.

The amino acids can be characterized by their relative hydrophobicity and hydrophilicity. For example, hydrophobic amino acids typically include Valine, Leucine, Isoleucine, Methionine, Tryptophan, Alanine, and Phenylalanine. Hydrophilic amino acids typically include Asparagine, Glutamic acid, Glutamine, Histidine, Lysine, Arginine, Serine, Threonine, and Aspartic acid. Amino acids falling in between include Glycine, Tyrosine, Cysteine and Proline.

Amino acids may include those having non-naturally occurring D-chirality, as disclosed in WO01/12654, which may improve the stability (e.g., half-life), bioavailability, and other characteristics of a polypeptide comprising one or more of such D-amino acids. In some cases, one or more, and potentially all of the amino acids of a therapeutic polypeptide have D-chirality.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

The term "post-translational modification" refers to a chemical modification of a protein after its translation. Examples of a post-translational modification include acetylation, amidation, alkylation, butyrylation, glycosylation, malonylation, hydroxylation, iodination, nucleotide addition, oxidation, phosphorylation, sulfation, succinylation, ubiquitination, myristolyation, palmitoylation, isoprenylation, etc. Typically a chemical group is added to an amino acid residue of a protein or peptide. A post-translation modification can also be added to a chemically synthesized peptide.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260: 2605-2608 (1985); and Rossolini et al., *Mol. Cell. Probes* 8:91-98 (1994)). The term nucleic acid is used interchangeably with gene, cDNA, and mRNA encoded by a gene.

The term "binding," "contacting" or "complexing" refers to the physical association of a peptide and a chemical molecule, usually by non-covalent bonding. For instance, a chemical molecule such as an organic dye can be docked or embedded in the three-dimensional structure of a peptide.

The term "specifically binds" when used in the context of describing a binding relationship of a particular organic dye to a peptide, refers to a binding reaction wherein the dye selectively binds the peptide in a heterogeneous population of peptides and other biologics. Thus, under designated fluorescence detecting assay conditions, the specified binding agent (e.g., an organic dye) binds to a particular peptide, does not substantially bind in a significant amount to other peptides present in the sample or reaction, and/or changes its fluorescence properties (e.g, fluorescence excitation spectrum, absorption spectrum, fluorescence emission spectrum, extinction coefficient, fluorescence quantum yield, quenching, photobleaching, fluorescence intensity, fluorescence output, etc.)

The term "fused" when used in the context of describing the relationship between a peptide and a polypeptide of a fusion protein, refers to the joining of a peptide and a polypeptide such that at least some of functional properties of the peptide and the polypeptide are maintained in the fusion protein. In the context of fusing two or more polynucleotide coding sequences to form a fusion coding sequence that encodes a fusion protein of interest, the coding sequences are joined in-frame such that the fusion polynucleotide is translated to form the desired fusion protein.

The term "targeting moiety" as used herein, refers to a protein that specifically or preferentially binds to a cell, viral particle, viral protein, an antigen, or a biomolecule, or that is localized to a specific cell type, tissue type, microbe type, or viral type.

The term "expression construct" refers to a nucleic acid construct, generated recombinantly or synthetically, with a series of specified nucleic acid elements that permit transcription of a particular polynucleotide sequence in a host cell. An expression construct may be part of a plasmid, viral genome, or nucleic acid fragment. Typically, an expression construct includes a polynucleotide to be transcribed, operably linked to a promoter. "Operably linked" in this context means two or more genetic elements, such as a polynucleotide coding sequence and a promoter, placed in relative positions that permit the proper biological functioning of the elements, such as the promoter directing transcription of the coding sequence. Other elements that may be present in an expression cassette include those that enhance transcription (e.g., enhancers) and terminate transcription (e.g., terminators), as well as those that confer certain binding affinity or antigenicity to the recombinant protein produced from the expression construct.

The term "host cell" refers to a cell to which biomolecules (e.g., nucleic acids, proteins, peptides, aptamer, and the like), viruses, or microorganism can be introduced. A host cell can be a prokaryotic cell, eukaryotic cell, a yeast cell, a fungal cell, an insect cell, or a vertebrate cell. In preferred embodiments, the host cell is a mammalian cell. In more preferred embodiments, the host cell is a human cell.

The term "dye" or "fluorescent dye" refers to a chemical molecule that has fluorescence. Upon absorption of transferred light energy (e.g., photon), a dye molecule goes into an excited state. As the molecule exits the excited state, it emits the light energy in the form of lower energy photon (e.g., emits fluorescence) and returns the dye molecule to its ground state. "Organic dye" refers to a dye comprising a carbon molecule. An organic dye can be natural chemical compound or a synthetic chemical compound.

The term "cyanine dye" includes a fluorogenic compound that comprises 1) a substituted or unsubstituted benzazolium moiety, 2) a polymethine bridge, and 3) a substituted or unsubstituted pyridinium or quinolinium moiety.

The term "triarylmethane dye" includes a synthetic organic compound containing triphenylmethane backbones.

The term "benzylidene imidazolinone dye" includes an organic compound that is structurally similar to the fluorophore, 4-hydroxybenzlidene imidazolinone (HBI), of green fluorescent protein.

The term "changing the fluorescence properties of the dye" refers to changes in fluorescence excitation spectrum, absorption spectrum, fluorescence emission spectrum, extinction coefficient, fluorescence quantum yield, quenching, photobleaching, fluorescence intensity, and fluorescence output of the dye after the peptide specifically binds to the dye. For example, prior to peptide specifically binding to the dye, the dye does not fluoresce prior to specifically binding with the peptide, but does fluoresce after specifically binding to the peptide.

The term "one-bead-one compound combinatorial library" or "OBOC" refers to a library composed of beads such that each bead displays a unique synthetic compound. The synthetic compounds of the library can include short linear peptides, cyclic peptides, peptoids, peptidomimetics, and small molecules.

III. Methods of Detecting a Peptide

The present invention provides methods for identifying and/or detecting short peptides that upon specifically binding to a particular organic dye change the fluorescence of the dye, such as by making the dye fluoresce. The peptides provided herein can be used to monitor the dynamics of signaling molecules in vitro and in living cells, and for a variety of other purposes. Specific biochemical and cellular functions of recombinant proteins fused to the peptides of the invention can also be monitored. In some embodiments, the peptides can be used to track (e.g., monitor, tag, label, probe) a series of intracellular proteins in a multiplex fashion. In other embodiments, the peptides can be used to probe biochemical and cellular functions in living cells.

The peptides can modulate the spectral and chemical properties of a given organic dye, which can reflect the location and modification of a protein of interest in vivo, thereby reporting the cellular function of the protein of interest in a cell or in a whole organism (e.g., human or other animal). In addition, the peptides can act as biological sensors to simultaneously report on a variety of cellular signaling pathways, even with spatiotemporal resolution.

The peptides of the present invention can be fused to a protein of interest to form a fusion protein. In some embodiments, the fusion protein is produced by a host cell that carries an expression construct comprising the coding sequence of the fusion protein. The fusion protein can be monitored by exposing it to an organic dye that changes it fluorescence when bound to the peptide sequence of the fusion protein.

Peptides capable of specifically binding an organic dye and changing the fluorescent properties of the dye can be identified by screening a one-bead-one-compound combinatorial peptide library with an organic dye. Fluorescence induced by peptide and dye binding can be detected using standard methods known to those in the art. The amino acid sequence of the selected peptide can be determined.

The peptides of the present invention change the fluorescent properties of an organic dye upon specifically binding to the dye. Fluorescent properties that can be altered include fluorescence excitation spectrum, absorption spectrum, fluorescence emission spectrum, extinction coefficient, fluorescence quantum yield, quenching, photobleaching, fluorescence intensity, and fluorescence output. For example, the fluorescence of the dye can be activated by the peptide specifically binding to the dye, or deactivated. In some embodiments, the fluorescence of the dye is activated following the peptide specifically binding to the dye, and is not fluorescent prior to the peptide specifically binding to the dye.

In some embodiments, the peptide and the dye can be bound non-covalently. In some embodiments, the dye docks in or inserts into the peptide.

In some embodiments, the organic dye does not fluoresce in the absence of the peptide and then does fluoresce upon binding. In other embodiments, the fluorescence emission range of the organic dye shifts upon binding to the peptide.

In some embodiments, the organic dye and the peptide are incubated for about 1 minutes to about 60 minutes, e.g., 1, 2, 3, 4, 5, 6, 7, 8, 9, 10, 15, 20, 25, 30, 35, 40, 45, 50, 55, or 60 minutes prior to detecting a change in the fluorescence of the dye.

A. Organic Dyes

Non-limiting examples of organic dyes that are useful in the present invention are described in, for example, Johnson, I., Histochemical Journal, 20:123-140 (1998), and *The Molecular Probes® Handbook*, 11th Edition, ed. Johnson and Spence, Life Technologies, Carlsbad, Calif., 2010.

In some embodiments, the organic dye can be triarylmethane dyes, cyanine dyes, benzylidene imidazolinone dyes, indigo dyes, or variants thereof. See, FIG. 1.

In some embodiments, the triarylmethane dye can be methyl red (MV) dyes, malachite green (MG) dyes, phenyl dyes, or variants thereof. Examples of triaryl MG-BE ester, cresol red, chlorophenol red, bromocresol purple and bromothymol blue. Triarylmethane dyes also include methyl green, pararosaniline, crystal violet, ethyl violet, victoria blue R, victoria pure blue BO, victoria blue B, or variants thereof.

In some embodiments, the cyanine dye can be thiazole orange (TO), TO-1F, TO-p2F, TO-CF3, TO-4F, dimethylindole red (DIR), α-CN-DIR, modified α-CN-DIR, or variants thereof. Cyanine dyes useful in the invention include, but are not limited to, carbocyanine dyes, monodimeric monomethine cyanine dyes, meptamethine cyanine dyes, aza-benzazolium cyanine dyes, symmetrical cyanine dyes unsymmetrical cyanine dyes, 6,8-difluoro-7-hydroxycoumarin, sulfonated derivatives of 7-aminocoumarin, merocyanine dyes, chloride-driven 3,3'-dipropylthiodicarbocyanine (DISC3-5), thiazole orange (TO), TO-1F, TO-p2F, TO-CF3, TO-4F, dimethylindole red (DIR), α-CN-DIR, modified α-CN-DIR, or variants thereof.

In some embodiments, the benzylidene imidazolinone dye can be 4-hydroxybenzylidene imidazolinone (HBI), 2-hydroxybenzylidene imidazolinone (2-HBI), 3,5-dimethoxy-4-hydroxybenzylidene imidazolinone (DMHBI), 4-dimethylaminobenzylidene imidazolinone (DMABI), 3,5-difluoro-4-hydroxybenzylidene imidazolinone (DFHBI), DMAHBI, MFBI, DMABI-CF3, DMABI-CF3-AE, DMHBI-CF3, DFHBI-CF3, HBI-CF3, DFMO, MFMO, DFHO, MFHO, DFAME, DMAME, MFAME, DMAMO, DMAAME, Di-DMABI, Di-DMABI-AE, Di-PDMABI, Di-HBI, Di-2-HBI, DiDFHBI, Di-DMHBI, or variants thereof.

In some embodiments, the indigo dye can be indigo, indigo carmine, thioindigo, ciba blue, tyrian purple, or variants thereof.

B. Peptides

Any suitable peptide can be used in the invention provided herein. For instance, the peptide can have any structure or any function. In some embodiments, the peptides can be designed de novo. In other embodiments, the peptides are based on amino acid sequences from native proteins.

In some embodiments, the peptide is about 0.5 kDa to about 2.6 kDa. In other embodiments, the peptide is about 0.8 kDa to about 1.6 kDa. Due to the peptide's small size, it can be fused to a protein of interest without interfering with the function (e.g., activity of the protein). In some embodiments, the amino acid sequence of the peptide is inserted into the amino acid sequence of the protein of interest.

In some embodiments, the peptide is a linear peptide. In some embodiments, the peptide is branched. In other embodiments, the peptide has a helical structure. In some embodiments, the peptide is not a cyclic peptide. The peptides of the present invention can also be cyclized or constrained by any means known in the art. For example, the peptide can be cyclized via disulfide bonds, or conformationally constrained by chelation with a variety of metals, such as, but not limited to $Ca^{2+}$ or $Zn^{2+}$. In some embodiments, the peptide can be cyclized by a disulfide bond. In some embodiments, the peptide can be conformationally constrained by chelating metal ions such as $Ca^{2+}$ and $Zn^{2+}$.

In some embodiments, the peptide is about 5 amino acids to about 100 amino acids in length, for instance, about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids long. In some embodiments, the peptide is about 10 to 50 amino acids in length, e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids. In some embodiments, the peptides includes from about 10 to about 25 amino acids. In some embodiments, the peptides includes from about 10 to about 20 amino acids.

A functional way to define common properties between individual amino acids is to analyze the normalized frequencies of amino acid changes between corresponding proteins of homologous organisms (see, e.g., Schulz, G. E. and R. H. Schirmer, Principles of Protein Structure, Springer-Verlag). According to such analyses, groups of amino acids may be defined where amino acids within a group exchange preferentially with each other and, therefore, resemble each other most in their impact on the overall protein structure (see, e.g., Schulz, G. E. and R. H. Schirmer, Principles of Protein Structure, Springer-Verlag). One example of a set of amino acid groups defined in this manner include: (i) a charged group, consisting of Glu and Asp, Lys, Arg and His;

(ii) a positively-charged group, consisting of Lys, Arg and His; (iii) a negatively-charged group, consisting of Glu and Asp; (iv) an aromatic group, consisting of Phe, Tyr and Trp; (v) a nitrogen ring group, consisting of His and Trp; (vi) a large aliphatic nonpolar group, consisting of Val, Leu and Ile; (vii) a slightly-polar group, consisting of Met and Cys; (viii) a small-residue group, consisting of Ser, Thr, Asp, Asn, Gly, Ala, Glu, Gln and Pro; (ix) an aliphatic group consisting of Val, Leu, Ile, Met and Cys; and (x) a small hydroxyl group consisting of Ser and Thr. In the context of this invention, reference to the charge of an amino acid refers to the charge at physiological pH.

In some embodiments, the peptide comprises L-amino acids, D-amino acids, natural amino acids, non-natural amino acids, derivatives thereof, or combinations thereof. Non-natural amino acids include any non-proteinogenic amino acid that either occur naturally or are chemically synthesized. Examples of non-natural amino acids include β-amino acids, homo-amino acids, proline and pyruvic acid derivatives, 3-substituted alanine derivatives, glycine derivatives, ring-substituted phenylalanine and tyrosine derivatives, linear core amino acids, diamino acids, d-amino acids, N-methyl amino acids, DAB (2,4-diaminobutyric acid), DAP (2,3-diaminopropionic acid), N-methyl amino acids, norleucine derivatives, ornithine derivatives, penicillamine derivatives, phenylglycine derivatives, and pyroglutamine derivatives.

In some embodiments, the peptide comprises at least two leucine residues at the N-terminus and/or C-terminus of the peptide to facilitate the formation of a complex with the dye.

The peptide can have an N-terminal, C-terminal or internal peptide modification. For example, the peptide can have an N-terminus modification such as acetylation, formylation, benzyloxylcarbonylation and succinylation, a C-terminal modification such as amidation, or another modification such as phosphorylation and PEGylation.

In some embodiments, the peptide can be at least two short peptide segments linked (attached) together by a chemical linker, e.g., a PEG linker. In some embodiments, two peptide segments, each about 5 to 6 amino acids in length, are linked together by a highly flexible and hydrophilic PEG linker, such that one segment can interact with the organic dye, and the other can form a ternary complex, thereby producing fluorescence.

The peptides of the present invention can have any suitable formula. In some embodiments, the peptide can have Formula I:

(I) (SEQ ID NO: 183)
$X_1X_2X_3X_4X_5X_6X_7X_8X_9X_{10}X_{11}X_{12}$ wherein each of $X_1$ and $X_2$ can be absent or a negatively charged amino acid independently selected from E and D; each of $X_3$, $X_4$, $X_8$ and $X_{10}$ can be an amino acid independently selected from V, L, I, M, F, G, A, S, T, Y, W, C and P; each of $X_5$, $X_6$, $X_7$, $X_9$ and $X_{11}$ can be an amino acid independently selected from V, L, I, M, F, N, E, Q, H, K, R, D, G, A, S, T, Y, W, C and P; and $X_{12}$ can be a negatively charged amino acid independently selected from E and D. In some embodiments, each of $X_1$ and $X_2$ can be absent or can be D; each of $X_3$, $X_4$, $X_8$ and $X_{10}$ can be an amino acid independently selected from V, L, I, M, F, G, A, S, T, Y, W, C and P; each of $X_5$, $X_6$, $X_7$, $X_9$ and $X_{11}$ can be an amino acid independently selected from V, L, I, M, F, N, E, Q, H, K, R, D, G, A, S, T, Y, W, C and P; and $X_{12}$ can be E (SEQ ID NO:212).

In some embodiments, the peptide can have Formula Ia:

(Ia) (SEQ ID NO: 184)
$X_1X_2X_3X_4TGRX_8SX_{10}GX_{12}$ wherein each of $X_1$ and $X_2$ can be absent or a negatively charged amino acid independently selected from E and D; each of $X_3$, $X_4$, $X_8$ and $X_{10}$ can be a hydrophobic amino acid independently selected from V, L, I, M, F, G, A, S, T, Y, W, C and P; $X_{12}$ can be a negatively charged amino acid independently selected from E and D. In some embodiments, peptides of Formula I can be selected from AITGRYSIGE (SEQ ID NO:182), DAITGRYSIGE (SEQ ID NO:181), and DDAITGRYSIGE (SEQ ID NO:170).

In some embodiments, the peptide can have Formula II:

(II) (SEQ ID NO: 213)
$X_1X_2X_3X_4X_5X_6X_7X_8X_9X_{10}X_{11}X_{12}$ wherein each of $X_1$, $X_2$, $X_3$, $X_4$, and $X_5$ can be an amino acid independently selected from N, E, Q, H, K, R, A, D, Y, W and P; each of $X_6$, $X_7$, $X_8$, $X_9$, $X_{10}$, and $X_{11}$ can be an amino acid independently selected from V, L, I, M, F, N, E, Q, H, K, R, D, G, A, S, T, Y, W, C and P; and $X_{12}$ can be an amino acid selected from D and E. In some embodiments, the peptide can have Formula IIa:

(IIa) (SEQ ID NO: 185)
$X_1X_2X_3X_4X_5GX_7X_8X_9X_{10}X_{11}E$ wherein each of $X_1$, $X_2$, $X_3$, $X_4$, and $X_5$ can be an amino acid independently selected from D, A, Y and W, wherein at least one of $X_1$, $X_2$, $X_3$, $X_4$, and $X_5$ can be D and at least one of $X_1$, $X_2$, $X_3$, $X_4$, and $X_5$ can be W; and each of $X_6$, $X_7$, $X_8$, $X_9$, $X_{10}$, and $X_{11}$ can be an amino acid independently selected from V, L, I, M, F, N, E, Q, H, K, R, D, G, A, S, T, Y, W, C and P. In some embodiments, the peptide can have Formula IIb:

(IIb) (SEQ ID NO: 186)
$DX_2X_3X_4X_5GX_7X_8X_9X_{10}X_{11}E$ wherein each of $X_2$, $X_3$, $X_4$, and $X_5$ can be an amino acid independently selected from D, A, Y and W, wherein at least one of $X_2$, $X_3$, $X_4$, and $X_5$ can be is W; and each of $X_6$, $X_7$, $X_8$, $X_9$, $X_{10}$, and $X_{11}$ can be an amino acid independently selected from V, L, I, M, F, N, E, Q, H, K, R, D, G, A, S, T, Y, W, C and P. In some embodiments, the peptide of Formula II can be selected from

DAYWDGTGHIYE, (SEQ ID NO: 204)

DWWDWGNHGYTE, (SEQ ID NO: 31)
and

DWWWDGFERLEE. (SEQ ID NO: 23)

In some embodiments, the peptide can have Formula III:

(III)
(SEQ ID NO: 187)
YIY(P)$_n$GSFKKK-X$_1$X$_2$X$_3$X$_4$X$_5$X$_6$X$_7$X$_8$X$_9$X$_{10}$ wherein each of X$_1$, X$_2$, X$_3$, X$_4$, X$_5$, and X$_6$ can be an amino acid independently selected from V, L, I, M, F, N, E, Q, H, K, R, D, G, A, S, T, Y, W, C and P; each of X$_7$, X$_8$, X$_9$, X$_{10}$ can be absent or an amino acid independently selected from V, L, I, M, F, N, E, Q, H, K, R, D, G, A, S, T, Y, W, C and P; p can be phosphate; and subscript n can be 0 or 1. In some embodiments, the peptide of Formula III can be selected from (SEQ ID NO: 154)
YIY(P)GSFKKK-YFGVHS, (SEQ ID NO: 155)
YIY(P)GSFKKK-ESVYIE, (SEQ ID NO: 156)
YIY(P)GSFKKK-YFNAINT, (SEQ ID NO: 157)
YIY(P)GSFKKK-NYHYEIEY, (SEQ ID NO: 158)
YIY(P)GSFKKK-NYTWYVSY, (SEQ ID NO: 159)
YIY(P)GSFKKK-DQEFTAFM, (SEQ ID NO: 160)
YIY(P)GSFKKK-DRMFTTWSD, (SEQ ID NO: 161)
YIY(P)GSFKKK-FMLWMDETY,
and (SEQ ID NO: 162)
YIY(P)GSFKKK-FMLWMDETYG.

In some embodiments, the peptide can have Formula IV:

(IV)
(SEQ ID NO: 188)
EAIY(P)$_n$AAPFAKK-X$_1$X$_2$X$_3$X$_4$X$_5$X$_6$X$_7$X$_8$ wherein each of X$_1$, X$_2$, X$_3$, X$_4$, X$_5$, and X$_6$ can be an amino acid independently selected from V, L, I, M, F, N, E, Q, H, K, R, D, G, A, S, T, Y, W, C and P; each of X$_7$ and X$_8$ can be absent or an amino acid independently selected from V, L, I, M, F, N, E, Q, H, K, R, D, G, A, S, T, Y, W, C and P; p can be phosphate; and subscript n can be 0 or 1. In some embodiments, the peptide of Formula IV can be selected from (SEQ ID NO: 163)
EAIY(P)AAPFAKK-YTFELT, (SEQ ID NO: 164)
EAIY(P)AAPFAKK-GYWGWFTF,
and (SEQ ID NO: 165)
EAIY(P)AAPFAKK-LYIMDGWF.

In some embodiments, the peptide can have Formula V:

(V)
(SEQ ID NO: 189)
LRRAS(P)$_n$L-X$_1$X$_2$X$_3$X$_4$X$_5$X$_6$X$_7$X$_8$X$_9$X$_{10}$ wherein each of X$_1$, X$_2$, X$_3$, X$_4$, X$_5$, X$_6$, X$_7$, and X$_8$ can be an amino acid independently selected from V, L, I, M, F, N, E, Q, H, K, R, D, G, A, S, T, Y, W, C and P; each of X$_9$ and X$_{10}$ can be absent or an amino acid independently selected from V, L, I, M, F, N, E, Q, H, K, R, D, G, A, S, T, Y, W, C and P; p can be phosphate; and subscript n can be 0 or 1. In some embodiments, the peptide of Formula V can be selected from (SEQ ID NO: 166)
LRRAS(P)L-PFMMLWLWSK,
and (SEQ ID NO: 167)
LRRAS(P)L-REIFVSEWM.

Peptides of the present invention can be chemically synthesized using standard methods known in the art, for example, Fmoc solid-phase technology. The synthesized peptides can be purified using HPLC. The purity of the peptides can be assessed by HPLC, and identity can be verified by mass spectrometry.

C. Methods of Detecting Fluorescence

Fluorescence from an organic dye specifically bound to a peptide can be detected by standard methods known in the art, such as fluorescent detection systems. Typically, a fluorescent detection system contains an excitation light source, wavelength filters to isolate emission photons from excitation photons, and a detector. Detection instruments include spectrofluorometers, microplate readers, fluorescence microscopes, fluorescence scanners, flow cytometers, capillary electrophoresis apparatus, and microfluidic devices.

IV. Genetically Encoded Small Illuminant (GESI)

In some embodiments, the peptide of the present invention changes the fluorescence of an organic dye after undergoing a conformation change upon binding to a second messenger (e.g., calcium (Ca$^{2+}$)) or upon post-translational modification (e.g., phosphorylation, methylation, acetylation, deacetylation, etc.)

In some embodiments, the genetically encoded small illuminant (GESI) comprises a peptide that serves as a substrate for a specific enzyme (e.g., protein kinase or a histone modifying enzyme), wherein the modified peptide can change the fluorescence of a particular organic dye upon binding. In some instances, the GESI can change the fluorescence intensity of an organic dye upon binding, when the peptide is post-translationally modified and/or when the post-transitional modification is reversed. Such a peptide can be identified by determining the interactions of each bead of the OBOC library with a series of dyes at various concentrations before and after enzymatic phosphorylation.

In some embodiments, the GESI is a substrate for a protein kinase (e.g., PKA, MAPK and JNK), and thus can be phosphorylated by the enzyme in an in vitro reaction. In particular instances, the peptide of the GESI has an amino acid sequence set forth as XXX(X)$_n$RRXS(X)$_n$XXX (SEQ ID NO: 1), XX(X)$_n$RRXT(X)$_n$XXXX (SEQ ID NO:2), XXXX(X)$_n$S(X)$_n$XXXX (SEQ ID NO:3), XXXX(X)$_n$T(X)$_n$XXXX (SEQ ID NO:4), XXX(X)$_n$SP(X)$_n$XXX (SEQ ID NO:5), and XXX(X)$_n$TP(X)$_n$XXX (SEQ ID NO:6), wherein X is any amino acid residue, n is 1 to 6 amino acid residues, and serine (S) or threonine (T) can be phosphorylated.

In other embodiments, the GESI comprises a peptide that undergoes a conformation change upon binding to calcium ($Ca^{2+}$), as well as, change the fluorescent intensity of an organic dye upon bind to the dye. To identify a calcium-sensitive peptide, the fluorescent intensity of the organic dye is detected in the absence and presence of calcium after exposing the organic dye to the peptide library.

In some embodiments, the GESI is a substrate for a histone modification enzyme that can phosphorylate, acetylate and/or methylate histone proteins including H3, H2A, H2B and H4. In particular instances, the peptide of the GESI has an amino acid sequence set forth as RKSTTG(X)$_n$GKAPR (SEQ ID NO:7), (X)$_n$ARTKQTAR (SEQ ID NO:8), and (X)$_n$SGRGKQG (SEQ ID NO:9), wherein serine (S) or threonine (T) can be phosphorylated, lysine (K) can be acetylated or methylated.

In some embodiments, the genetically encoded peptide is fused to a protein of interest to form a GESI-protein chimeric protein. For instance, the peptide can be fused to the C-terminus, N-terminus, or internal region of the protein of interest. Optionally, the peptide is fused to a portion of the protein such that the peptide is located on the surface of the tertiary structure of the protein. In some instances, a linker, such as an amino acid linker, is placed between the peptide and a region of the protein of interest (e.g., C-terminus or N-terminus).

The genetically encoded peptide can be fused to a full-length protein, or fragment thereof. In some embodiments, a protein-trafficking signal peptide segment, a tethering motif, a docking domain, or combinations thereof is added to the GESI fusion protein.

Peptides of the present invention can be fused to any number of proteins of interest including antibodies and fragments thereof, peptide aptamers, cell surface receptors, ion channels, enzyme substrates, viral proteins (e.g., hepatitis E-like viral coat proteins), microbial proteins, cytoskeletal proteins, organelle-specific proteins, cell-specific proteins, and tissue specific proteins.

V. Expression Constructs

In some embodiments, the peptide of the present invention can be fused to a protein of interest using standard molecular biology techniques known to those in the art. In some instances, the peptide and protein of interest are produced by recombinant DNA techniques, such as PCR amplification and cloning, to generate a fusion protein.

The expression constructs described herein can be operably linked to a promoter and/or terminator so that the desired transcript(s) and fusion protein (e.g., peptide and protein of interest) are expressed in a cell cultured under suitable conditions. Methods for designing and making expression constructs and fusion proteins are well known to those skilled in the art. See, e.g., Lackie, DICTIONARY OF CELL AND MOLECULAR BIOLOGY, Elsevier (4$^{th}$ ed. 2007) and Sambrook et al., MOLECULAR CLONING, A LABORATORY MANUAL, Cold Springs Harbor Press (Cold Springs Harbor, N.Y. 1989).

The polynucleotide sequence encoding the fusion protein can be prepared by any suitable method known to those of ordinary skill in the art, including, for example, direct chemical synthesis or cloning. For example, in direct chemical synthesis, oligonucleotides of up to about 40 bases are individually synthesized, then joined (e.g., by enzymatic or chemical ligation methods, or polymerase-mediated methods) to form essentially any desired continuous sequence.

Further, commercial services are available that can supply synthetic genes of the desired sequence. In addition, the desired sequences may be isolated from natural sources using well known cloning methodology, e.g., employing PCR to amplify the desired sequences and join the amplified regions.

The nucleic acid coding sequences for the fusion protein can be incorporated into an expression vector. Those of ordinary skill in the art are familiar with the necessary steps for incorporating a nucleic acid sequence into an expression vector (e.g., ligating) and for introduction to a cell (e.g., transforming, transfecting, infecting, etc.).

As will be appreciated by those of ordinary skill in the art, the invention is not limited with respect to the precise promoter or expression vector used. Although any suitable expression vector may be used to incorporate the desired sequences, readily available expression vectors include, without limitation: mammalian expression plasmids, baculoviral vectors, lentiviral vectors, adenoviral vectors. Certain expression vectors may only be suitable for particular host cells which can be readily determined by one of ordinary skill in the art. For example, the expression vector can be introduced into the host cell, which is then monitored for viability and expression of the sequences contained in the vector. In addition, reference may be made to the relevant texts and literature, which describe expression vectors and their suitability to any particular host cell.

The expression constructs of the invention must be introduced or transferred into the host cell. Such methods for transferring the expression vectors into host cells are well known to those of ordinary skill in the art. For example, viral infection, lipid based transfection, electroporation, calcium phosphate transfection, microinjection may be employed. Those of ordinary skill in the art can transfect a host cell with a desired sequence using these or other methods.

The expression construct can be transiently expressed in the host cell. In some instances, the expression construct is integrated into the genome of the host cell.

In some embodiments, the host cell is a mammalian cell, such as a cell derived from a human, rodent, bovine, ovine, porcine, feline, canine, and the like. In some embodiments, the host cell is located in an living organism. In other embodiments, the host cell is cultured ex vivo.

A variety of methods are available for identifying a transfected cell. For example, a culture of potentially transfected cells may be separated, using a suitable dilution, into individual cells and thereafter individually grown and tested for expression of the desired nucleic acid sequence. In addition, cells can be selected based on antimicrobial resistance that has been conferred by genes intentionally contained within the expression vector, such as a pac, zeo, gsd, neo, or hyg gene. The cell can be transformed with one or more expression vector. If more than one expression vector is introduced, each vector can include a different selective criteria.

Once a cell has been transformed with the expression vector, the cell is cultured and typically allowed to grow.

VI. Method for Identifying Short Peptide and Dye Pairs

In some instances, peptides that specifically activate the fluorescence of an organic dye can be identified by screening of immobilized OBOC combinatorial bead arrays affixed with a series of peptides with the organic dye. In some embodiments, the bead array is sequentially screened with a series of organic dyes (e.g., triarylmethane dyes, cyanine dyes, benzylidene imidazolinone dyes, indigo dyes, etc.).

Similar to standard bead screening methods known to those skilled in the art, OBOC libraries can be screened in suspension or affixed to a solid support.

In some embodiments, the OBOC peptide library is designed using computational modeling. For example, the library can be a 12-mer linear OBOC peptide library, in which the first amino acid is D (aspartic acid), the sixth amino acid is G (glycine), the 12$^{th}$ amino acid is Glu and the rest of the positions contain all 19 natural amino acids except cysteine to avoid peptide cyclization. The chemical structure of such library can be as follows: $DX_dX_dX_dX_dGXXXXXE$—Bead (SEQ ID NO:10). In the X position, the resin beads are distributed evenly for all 19 amino acids, whereas in the $X_d$ position, 50% of the beads are reacted with aspartic acid and the remaining 50% of the beads are distributed evenly for all the remaining 18 amino acids. In some instances, aspartic acid (D) is preferred in the first 5 residues of every peptide. In some instances, the library is designed for high probability of $Ca^{2+}$ binding.

In some embodiments, the OBOC peptide library can be immobilized to a solid support. An exemplary method of bead affixation is described herein, e.g., Examples. Briefly, the OBOC library is immobilized on the bottom of a standard polystyrene tissue culture Petri dish simply by submerging the dish in 90% N,N-dimethylformamide (DMF) inside the dish. High concentration of DMF softens the polystyrene surface such that library beads can be tacked down sufficiently that they remain in place even after multiple cycles of screening and washing with buffers and probes. Advantageously, the polystyrene surface remains optically clear after such treatment.

Screening methods for one-bed-one-compound (OBOC) combinatorial libraries are described in detail in, for example, U.S. Pat. Nos. 6,670,142; 7,262,269 and 7,291,456, which are hereby incorporated by reference for all purposes. OBOC libraries have been used to identify peptides, chemical oligomers, and small molecules directed against target proteins and cells (see, e.g., Liu et al., *ACS Comb. Sci.*, 13(5):537-543 (2011), Lam et al., *Acc. Chem. Res.*, 36:370-7 (2003), Xiao et al., *Mol. Cancer Ther.*, 9:2714-2723 (2010)).

Fluorescence intensity changes of the organic dye upon binding to a specific peptide of the library can be detected by microscopy, such as high-throughput screening using fluorescent microscopy. In some embodiments, the fluorescence intensity of the organic dye in the appropriate spectral range is acquired with fluorescent microscope after adding the organic dye to the library. The changes of fluorescent intensity due to specific binding of the dye to a particular peptide can be analyzed using imaging analysis software such as MATLAB.

VII. Kits

The present invention provides kits for practicing the methods described herein to generate a peptide that upon specifically bind to an organic dye changes the fluorescence of the dye, or a fusion protein comprising said peptide.

Kits typically include at least one peptide useful for binding a dye, such as an organic dye. Optionally, the peptide is linked or fused to a targeting moiety. Kits can include components useful for attaching (fusing) the peptide to the targeting moiety. In some case, the kits may also include the organic dye that can preferentially bind at least one peptide of the kit.

Kits for generating a fusion protein in a host cell typically include components useful for generating at least one polynucleotide encoding the fusion protein and an expression vector. In some embodiments, the kit contains a nucleic acid primer pair for amplifying the peptide of the present invention, a buffer, a DNA polymerase, dNTPs, etc.

VIII. Examples

Materials

The Silicone Elastomer Base and Silicone Elastomer Curing Agent kit (Sylgard® 184) were purchased from Dow Corning Corporation (Midland, Mich.). The color dyes Malachite green oxalate (FIG. 1A), Bromocresol purple (FIG. 1B) and Indigo carmine (FIG. 1C) were obtained from Sigma-Aldrich (Saint Louis, Mo.). TentaGel S $NH_2$ resin (90 µm, 0.26 mmol/g) was purchased from Rapp Polymere GmbH (Tubingen, Germany). Fmoc-Amino acids, 1-hydroxybenzotriazole (HOBt), and N,N'-diisopropylcarbodiimide (DIC) were purchased from GL Biochem (Shanghai, China). All solvents and other chemical reagents were purchased from Aldrich (Milwaukee, Wis.) and were analytical grade.

Example 1

Screening Method for Peptides Using an OBOC Library

This example illustrates a method for serially screening a random OBOC disulfide containing cyclic heptapeptide library with three water soluble dyes as model probes: malachite green, bromocresol purple and indigo carmine. This multiplicative screening approach resulted in a rapid determination of the binding profile of each and every bead respective to each of the three dyes. Beads that interacted with malachite green only, bromocresol purple only, or both indigo carmine and bromocresol purple were isolated, and their peptide sequences were determined with microsequencer.

This example also illustrates a method for securely affixing library micro-beads to the bottom of a standard tissue culture dish or microscope slide spin-coated with a thin layer of PDMS (polydimethylsiloxane), leaving approximately 95% of the bead surface freely exposed to the surrounding environment. The method of bead immobilization was more suitable for screens in which the surface of beads need to be readily exposed to surrounding aqueous environment to permit free interaction with target probes in solution such as proteins in buffer, cells in media, etc, thereby maximizing screening versatility and efficiency in a given assay.

Synthesis of OBOC library

OBOC combinatorial peptide library was constructed on TentaGel beads (polyethylene glycol grafted polystyrene beads, Rapp Polymere, Tubingen, Germany) using methods as described in, e.g., Lam., *Methods Enzymol.*, 2003, 369: 298-322, Liu et al., *QSAR Comb. Sci.*, 2005, 24:1127-1140. Standard solid phase peptide synthesis method with fluorenylmethyoxycarbonyl (Fmoc) chemistry was used to synthesize the peptide libraries. Briefly, TentaGel beads (2.0 g, loading 0.26 mmol/g) were swollen in DMF (30 mL) in a column for 3 h. After filtration and washing with DMF, a mixture of Fmoc-L-Cys(Trt)-OH (3 equiv), HOBt (3 equiv) and DIC (3 equiv) was added to the beads. The column was rotated until a Kaiser test (Peng et al., *Nat. Chem. Biol.*, 2006, 2(7):381-389) was negative. The resins were washed and subjected to Fmoc deprotection with 20% piperidine (5 min, 15 min). After washing with DMF, methanol (MeOH), DCM, and DMF, respectively, the beads were split into 19 equal portions in 19 tubes (5 mL). Nineteen different Fmoc-L-amino acids except L-cystine (3 equiv.), HOBt (3 equiv) and DIC (3 equiv) were dissolved in DMF, and separately added to the 19 tubes. The coupling was carried out at room temperature for 2 h. Four random tubes were chosen for a Kaiser test. After the Kaiser test was negative, the beads were pooled to a column, drained and washed with DMF three times. The same coupling procedure was repeated for additional 4 cycles with 19 Fmoc-L-amino acids. After the last cycle of coupling, the beads were combined, and Fmoc was deprotected, and coupled with Fmoc-L-Cys(Trt)-OH as described above. After Fmoc deprotection, the beads were washed with DMF, MeOH, and dichloromethane (DCM), respectively, three times. The beads were then dried under vacuum. Side-chain deprotection was achieved using a mixture of 82.5% trifluoroacetic acid: 5% phenol: 5% thioanisole: 5% water: 2.5% triisopropylsilane. After neutralization with 3% N,N-diisopropylethylamine (DIEA)/DMF (twice), the beads were washed sequentially with DMF, MeOH, DCM, DMF, DMF/water (60%, 30%) and water. The beads were transferred to a 1 liter bottle, to which was added 500 mL mixture of water, acetic acid and dimethyl sulfoxide (DMSO) (75:5:20) with the pH adjusted with ammonium hydroxide to 6.0. The bottle was shaken for two days until the Ellman test was negative. After filtration, the beads were thoroughly washed with $H_2O$. Finally, the bead library was stored in 70% ethanol/water or in 0.05% sodium azide/PBS at 4° C.

Bead Affixation

Silicon Elastomer Base was mixed completely with Silicone Elastomer Curing Agent at ratio 10:1 in volume and the solution was kept in vacuum container for 15 to 20 minutes to eliminate the gas bubbles formed during the mixing process. After the removal of all residual bubbles, approximately 0.5-1 mL of PDMS solution was added into the bottom of a 60 mm culture dish. The dish was then spun on a single wafer spin processor (Laurell Technologies Corporation®, model WS-6505-6NPP/Lite) to evenly distribute the solution over the plates, at a speed of 4000 rpm for 30 s. A 5 µm layer of PDMS was formed on the bottom of dish and was cured at 80° C. for 5 min or at room temperature for 24 hrs to allow for beads immobilization. Knowing that the PDMS coating was about 5 µm thick and the radius of bead was around 45 µm, the percentage of free bead surface area was estimated by the formula of $[1-2\pi rh/4\pi r^2] \times 100\%$ (h=thickness of PDMS layer; r=radius of bead) to be approximately 95%. The library beads resuspended in 70% ethanol solution were first randomly placed on the surface of a glass plate that was 10% smaller than the dish used in the experiment. After the ethanol evaporated, a syringe needle was used to adjust the dry beads to evenly redistribute beads on the glass surface. Then the dish was inverted and the PDMS layer was pressed down onto the glass plate with beads. The library beads were embedded partly inside the PDMS layer.

Organic Dye Application

Dye solutions were prepared in PBS to a 100 µM final concentration and 5 mL of each dye solution were added into the 60 mm dish with beads. Three dyes were tested sequentially. The dish was kept swirling at 60 rpm on the rotator. The dye binding was monitored for 90 minutes, and then the dye solution was removed from the dishes and PBS was added to rinse the beads on the bottom to remove the color dye. The PBS solution was changed every 30 min and the dish was always swirled as above. The beads color change was also observed and recorded at certain time interval during the whole wash process to collect data of color dissociation. Before adding the next dye solution, beads were washed with 70% ethanol to completely remove residual dye and were rinsed with PBS solution three times afterwards.

Bead Color Quantification

A representative positive bead for each color was selected for the color binding and dissociation study. A series of images were taken at different time points during the binding and washing process. From the images taken, regions of interest (ROI) with the same size were picked up from the color beads and colorless control beads. The value from the control bead was subtracted from the color bead to get quantitated color value for each single color bead. The measure of the color intensity for each color dye was performed using the Kodak Image Station 2000MM.

To enable automated scan of all areas in the plate with OBOC library immobilized, a 4× objective was combined with the tiling function in Metamorph®. In total, an area of 1416×1157 pixel (1 pixel=1.6 µm) consisting of a couple of thousands of beads (3% of OBOC library) can be readily scanned within 10 mins. Sequential screening of immobilized bead arrays under different conditions, such as with calcium followed by EDTA, was also performed.

Bead Sequencing

Beads with different binding profiles were removed from the plates and washed sequentially with 8 M Guanidine HCl solution and water or with 6M guanidine HCl (pH 1.0) and 50% DMF/$H_2O$ to strip all bound dyes/proteins, followed by $H_2O$ wash (three times). Beads were then decoded using the Perkin-Elmer/Applied Biosystems Protein Sequencer (ABI Procise 494). This system works by sequentially cleaving N-terminal amino acids from a protein or peptide chains and then analyzing the formed phenylthiohydantoin (PTH)-amino acid derivatives.

Results

The PDMS affixed bead array was incubated with three different dyes sequentially. Beads were incubated with indigo carmine (i) until the color was saturated, and then the dye was washed away completely and incubated with the second dye malachite green (ii). The third dye bromocresol purple (iii) was last incubated after malachite green was removed. Eleven beads were selected for further analysis based on their characteristic binding profiles (FIG. 2). Beads #1, #3, #6, #8 and #11 bind only to malachite green. Beads #4, #5 and #9 beads bind only to bromocresol purple. Beads #2, #7 and #10 beads bind to both indigo carmine and bromocresol purple. The amino acid sequences of the peptides bound to the beads were determined (Table 1).

TABLE 1

Peptide sequences of selected beads.

| Bead number | SEQ ID NO: | Sequence | Dye binding |
|---|---|---|---|
| # 1 | SEQ ID NO: 11 | CNSPDIC | Malachite green |
| # 3 | SEQ ID NO: 12 | CQPDLTC | |
| # 6 | SEQ ID NO: 13 | CGNTEPC | |
| # 8 | SEQ ID NO: 14 | CMTQEAC | |
| # 11 | SEQ ID NO: 15 | CLSDEFC | |
| # 4 | SEQ ID NO: 16 | CHTHILC | Bromocresol purple |
| # 5 | SEQ ID NO: 17 | CHPLLPC | |
| # 9 | SEQ ID NO: 18 | CEIHRIC | |
| # 2 | SEQ ID NO: 19 | CLMNKWC | Indigo carmine and Bromocresol purple |
| # 7 | SEQ ID NO: 20 | CYKWWVC | |
| # 10 | SEQ ID NO: 21 | CKWILPC | |

For the three peptides that only bind bromocresol purple alone, each had one or two His and two hydrophobic residues (Leu and Ile). In the sequences which were shown to bind both bromocresol purple and indigo carmine (5,5'- indigodisulfonic acid sodium salt), there was a highly consistent appearance of the motif Lys-Trp and additional hydrophobic residues.

A key advantage of multiplicative beads screening strategy is that differences and/or similarities of conformation and structure among different targets can be directly assessed and considered for each bead/target interaction. For instance, there were two different groups of bead that only bind to malachite green or bromocresol purple, indicating that the dyes have separate and distinct structures and binding properties. Accordingly, the sequence results demonstrate a completely different preference among the dyes. The peptides that bind to malachite green include more acidic amino acids such as Asp or Glu, while and those that bind to bromocresol purple contain basic amino acids such as His or Lys. Malachite green tends to be more basic in nature while bromocresol purple is predisposed to be more acidic. By contrast, all of the beads shown to bind indigo carmine also bound to bromocresol purple, suggesting a similarity in structure or property between these two dyes. Indeed, the sequences obtained from the beads that interacted with both of these dyes shared a noticeable motif perhaps indicating a common interaction with sulfonic group characteristic to both dyes.

With the PDMS affixed bead method, it is possible to dynamically observe the peptide-dye interaction on each individual immobilized bead in real time. To further characterize the binding profile for each of the target/sequence interactions, beads #1, #4 and #10 were selected for binding and dissociation study with each respective target dye, by measuring the intensity of the resulting color accumulation on the bead surface at different time points. The values obtained for color intensity across progressing time points were plotted and the profiles for the three dye/bead interactions were compared. The association and dissociation rate of each organic dye to its respective binding peptide was evaluated.

Figure 3:
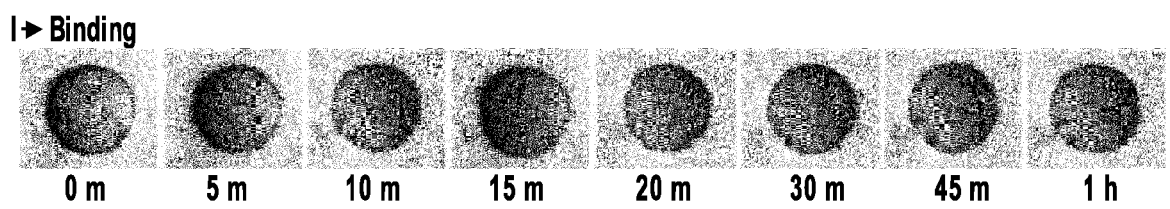
FIG. 3 illustrates real time association and dissociation of indigo carmine dye to #10 bead.
Figure 4:
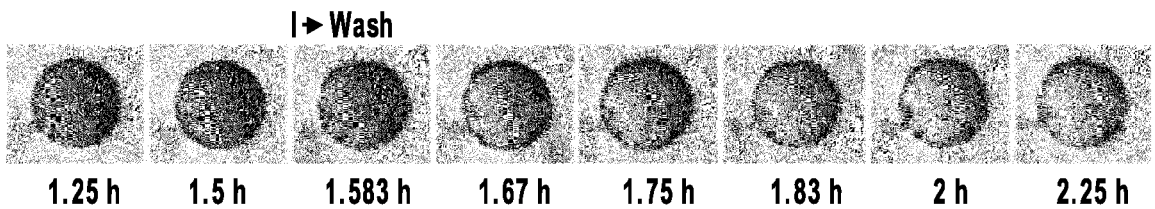
FIG. 4 illustrates real time association and dissociation of the bromocresol purple dye to #4 bead
Figure 6:
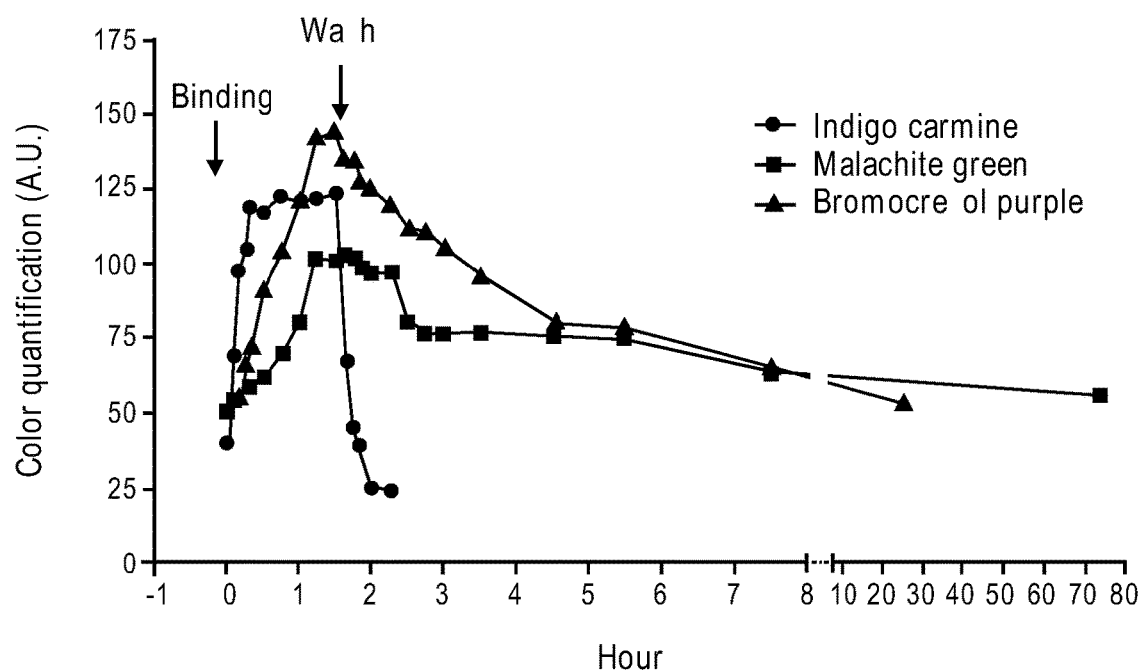
FIG. 6 illustrates real time association and dissociation curves of malachite green to #1 bead, bromocresol purple to #4 bead and indigo carmine to #10 after color quantitative analysis.

Upon incubation of bead #10 with indigo carmine dye, colorization was seen within five minutes and peaked after 30 to 45 minutes. The dissociation process also occurred relatively fast as the color began to fade immediately upon washing with PBS and was completely gone after 20 minutes (FIG. 3 and FIG. 6). Incubation of bead #1 with malachite green oxalate dye resulted in a colorization rate that was markedly slower than the indigo carmine to bead #10 interaction. Measurable colorization was seen after 20 to 30 minutes of dye incubation. After washing, the color did not completely diminish even after 72 hours. Only after thorough washing with 70% ethanol was complete dissociation observed (FIG. 4 and FIG. 6).

Figure 5A:
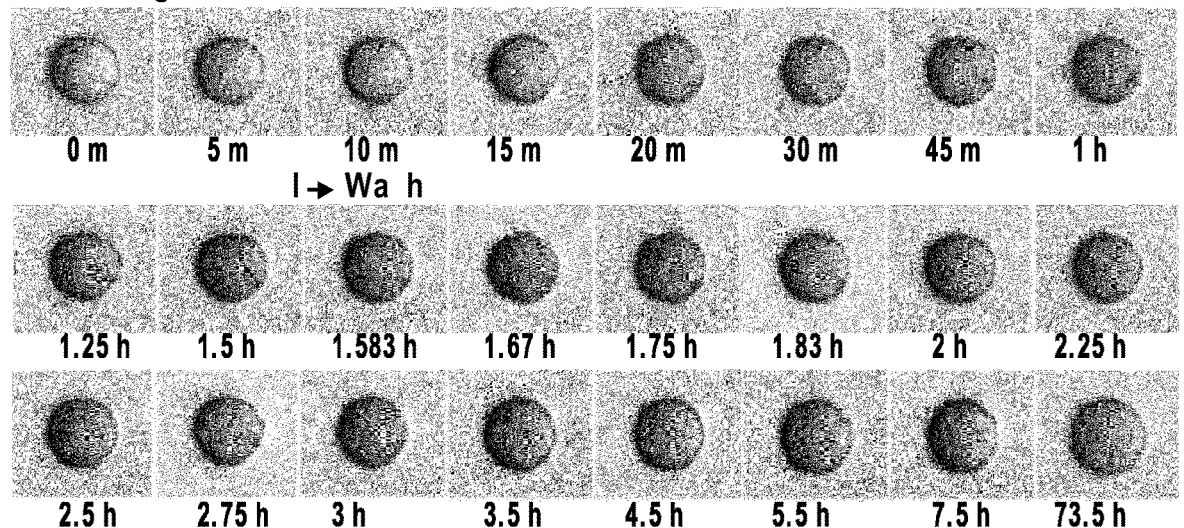
FIGS. 5A and 5B illustrate real time association and dissociation of the malachite green (MG) dye to the #1 bead.
Figure 5B:
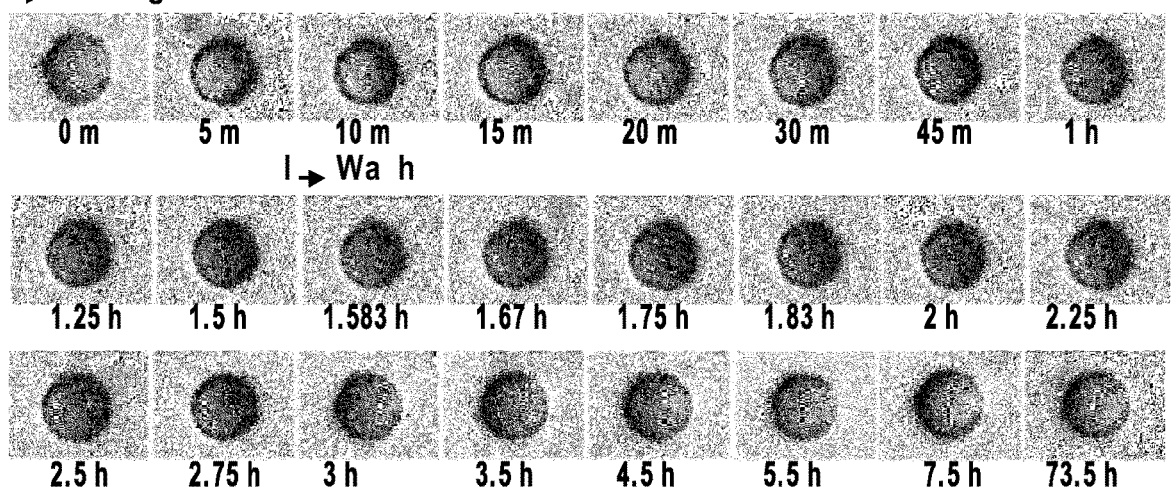

Incubating bead #4 with bromocresol purple dye also resulted in a slower color binding by comparison to the indigo carmine/bead #10 incubation, reaching its maximum around 75 minutes. The dissociation of the color also occurred slowly disappearing by 72 hours (FIGS. 5A-5B and FIG. 6). Interestingly, #10 bead was shown to also bind bromocresol purple, but the binding and dissociation rates appeared much slower than was observed with indigo carmine, suggesting a difference in binding profile between each of these two dyes and the cyclic peptide in spite of share similarities discussed previously. It is important to note that the color intensity of the bead was uniform throughout the entire study, thus eliminating the possibility that dye diffusion through the bead is the rate-limiting step of staining. Furthermore, the majority of the beads in the library remain colorless indicating that non-specific binding by the polystyrene matrix is totally absent.

In this exemplary embodiment of the method of the present invention, water soluble dyes such as indigo carmine, malachite green oxalate and bromocresol purple were chosen as the screening probes to validate the affixed bead library sequential binding assay. The peptide binding properties of each dye were characterized upon sequential screening of the same affixed bead peptide library against each of these dyes. The feasibility and utility of the PDMS affixed bead multiplicative library screening method and the adaptability of this approach to other screening methodologies were demonstrated.

Also provided herein is a simple and reliable method to immobilize microbeads on planar surface without fouling the bead surface necessary for many different biological assays. The PDMS affixed bead library screening method allows for not only identification of positive bead/target binding as permitted by existing bead screening assays, but also tracking of beads through successive target binding assays, resulting in a more informative and complete binding profile to multiple strategic targets of interest. Furthermore, the method facilitates real time binding analysis for each individual bead within a library or sample, delivering more characteristic information from bead compounds and their targets.

Example 2

Characterization of Malachite Green-activating Peptides

This example illustrates a method of the present invention for utilizing a one-bead-one-compound library for identifying 12-mer peptides, which upon binding to malachite green fluoresce in infra-red spectral region. Eleven peptides were discovered in the high-throughput screening assay. Two peptides (peptide #2 and peptide #12) showed strong binding characteristics in solution studies. The selected peptides were expressed in the cellular membrane and nucleus of living cells and monitored using malachite green. Peptide #2 showed sensitivity to calcium upon acetylcholine stimulation.

OBOC Library Design for Calcium Sensitive 12mer Peptide

A 12-mer linear OBOC peptide library was designed based on the EF hand structure in calcium binding proteins, in which the first amino acid is Asp, the sixth amino acid is Gly, and the $12^{th}$ amino acid is Glu. The rest of the positions contain all 19 natural amino acids except Cys to avoid peptide cyclization. The chemical structure of such library is as follows: $DX_dX_dX_dX_dGXXXXXE$ (SEQ ID NO:10) affix to a bead. In the X position, the resin beads were distributed evenly for all 19 amino acids, whereas in the $X_d$ position, 50% of the beads were reacted with Asp and the remaining 50% of the beads were distributed evenly for all the remaining 18 amino acids. In this way, Asp is preferred in the first 5 residues of every peptide. This library design assures high probability of $Ca^{2+}$ binding. Such flexibility of library design is not possible with phage-display or yeast-display peptide libraries. This library has permutation of about $3.3 \times 10^{11}$ different peptides.

The OBOC combinatorial peptide library was constructed on TentaGel beads (polyethylene glycol grafted polystyrene beads, Rapp Polymere, Tubingen, Germany). Standard solid phase peptide synthesis method with fluorenylmethyoxycarbonyl (Fmoc) chemistry is used to synthesize these peptide libraries. Briefly, the resin is first divided into 19-20 aliquots and each aliquot is reacted with a single Fmoc-amino acid. Coupling is initiated by the addition of a 3× molar excess of HOBt/DIC, or HBTU/DIEA. The coupling reactions are driven to completion with three-fold molar excess of Fmoc-amino acids and monitored by the standard ninhydrin test. Subsequently the aliquots are washed, mixed thoroughly, washed again, deprotected by 20% piperidine (5 min, 15 min), washed again, and redivided into 19-20 aliquots for the next cycle of coupling. In some position, only one amino acid may be used for the entire library bead. After the last coupling cycle is completed, the side-chain protecting groups are removed by reagent K (82.5% trifluoroacetic acid, 5% phenol, 5% thioanisole, 5% water, 2.5% ethanedithiol, v/v). The resin beads are then neutralized with 2% DIEA, washed with DMF, methanol, dichloromethane, DMF, 30% water/DMF, 60% water/DMF, water, PBS (phosphate-buffered saline) buffer. The bead libraries are stored in 0.05% sodium azide/PBS at 4° C.

OBOC Library Immobilization

In previous traditional bead screening methodologies, the libraries were screened against specific targets such as proteins, kinases, proteases or live cells in suspension with no means of reliably immobilizing the beads without fouling the bead surface for molecular interactions. The positive beads were then selected for identification or for next round of screening. Any subsequent screening analyses performed on the positive or negative beads identified in the initial screen could not be conveniently tracked and compared to the result of the previous screens.

To screen for peptides suitable for development into GESI, an assay system was developed such that interactions of each and every peptide-bead with a series of probes were tracked and quantified in each step. For example, to identify a calcium sensitive peptide, which binds to malachite green a two-step bead screening method was created: first with $Ca^{2+}$ and malachite green and next with EDTA solution. A novel and highly robust bead immobilization method was devised using DMF to glue beads onto the polystyrene surface of petri dishes such that a bead library array can be prepared and screened in its entirety, and repeatedly as well as sequentially with a series of distinct probes. This method not only increased the screening efficiency but also enabled the determination of the binding profile of each and every library bead against a large number of target dyes.

High-throughput Screening Method of the Library

The peptide library was screened against different concentrations of malachite green (MG). Fluorescence intensity of MG in the infrared range was acquired with wide-field fluorescent microscope in the presence of both saturated calcium followed by the introduction of calcium chelator, EDTA, 5 mins after MG addition. Those beads with strongest fluorescence at lowest concentration of MG were selected for sequencing.

To enable automated scan of all areas in the plate with OBOC library immobilized, we take advantage of 4× objective combined with tiling function in MetaMorph™. In total, an area of 1416×1157 pixels (1 pixel=1.6 μm) consisting of a couple of thousands of beads (3% of OBOC library) can be readily scanned within 10 min. Sequential screening of immobilized bead arrays under different conditions, such as with calcium followed by EDTA, was performed.

Individual positive beads were localized and retrieved from the bead array with 20-gauge needles and micropippettes. These beads further were washed three times with 6M guanidine HCl (pH 1.0) and 50% DMF/$H_2O$ to strip all bound dyes/proteins, followed by $H_2O$ wash (three times). After the washings, the beads were ready to be submitted for microsequencing with Edman chemistry using an automatic microsequencer (ABI Procise 494).

Figure 7:
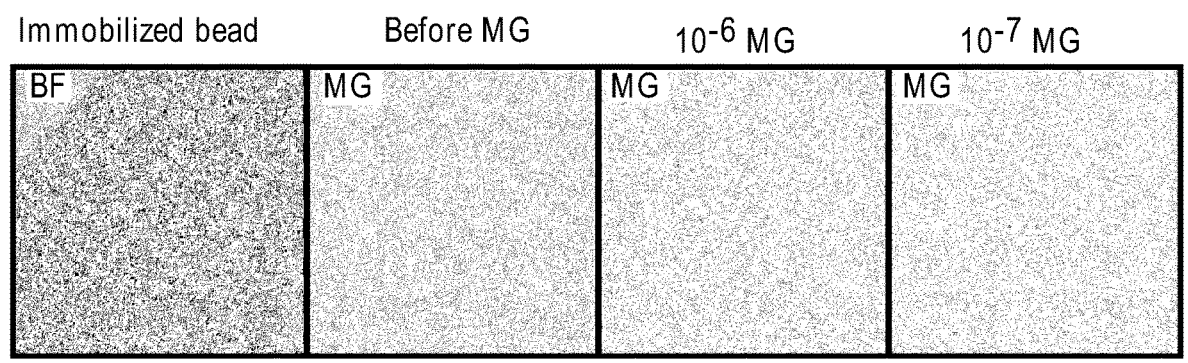
FIG. 7 shows images from the automated high-throughput screening system. Beads were immobilized on an 100-mm plate, followed by incubation with MG.

The changes of fluorescent intensity in the presence and absence of calcium was analyzed using customized algorithm based on ROI approach in MATLAB. Top 5% ROI with the largest fluorescent changes were selected for output with identified locations (FIG. 7). In addition, bright field image was also acquired for future retrieval of the positive beads. Eleven positive beads were found which showed fluorescence upon binding to MG in presence of 2 mM $Ca^{2+}$ solution but did not show any infrared fluorescent in present of the cheator, EDTA (Table 2).

TABLE 2

Peptide sequences of positive beads found by in vitro screening.

| SEQ ID NO | Peptide Name | Amino acid sequence |
|---|---|---|
| SEQ ID NO: 22 | Peptide 1 | DILDDGDEIQGE |
| SEQ ID NO: 23 | Peptide 2 | DWWWDGFERLEE |
| SEQ ID NO: 24 | Peptide 3 | DRDGDGDHRKIE |
| SEQ ID NO: 25 | Peptide 4 | DSDSWGEYFHEE |
| SEQ ID NO: 26 | Peptide 5 | DFMRQGVYDIPE |
| SEQ ID NO: 27 | Peptide 6 | DDYDDGWIYEFE |
| SEQ ID NO: 28 | Peptide 8 | DGDDGGYWPFPE |
| SEQ ID NO: 29 | Peptide 10 | DEWHDGMEGNLE |
| SEQ ID NO: 30 | Peptide 11 | DSKDPGMTHLKE |
| SEQ ID NO: 31 | Peptide 12 | DWWDWGNHGYTE |
| SEQ ID NO: 32 | Peptide 13 | DAQWMGANMHTE |

In Vitro Characterization of MG-activating Peptides

Figure 8A:
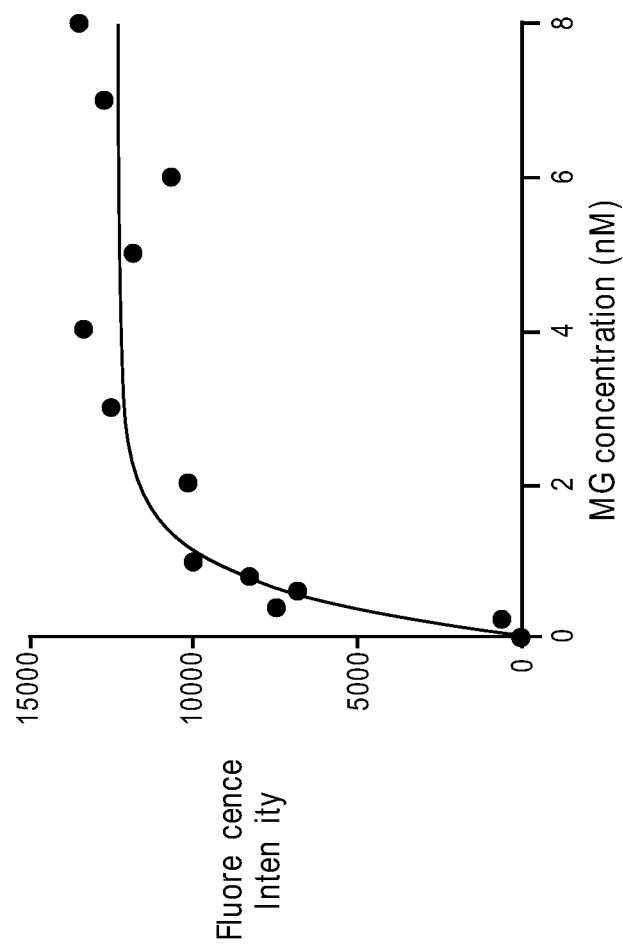
FIGS. 8A and 8B illustrate the fluorescence activity of MG upon binding to peptide 12.
Figure 8B:
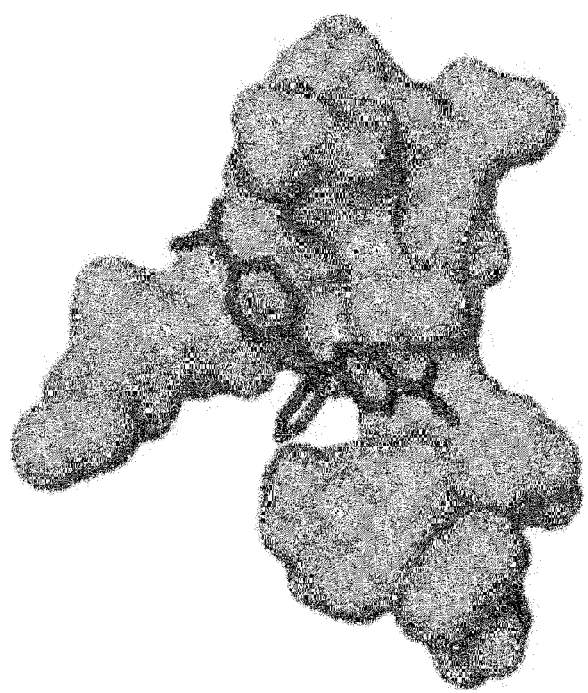
Figure 9A:
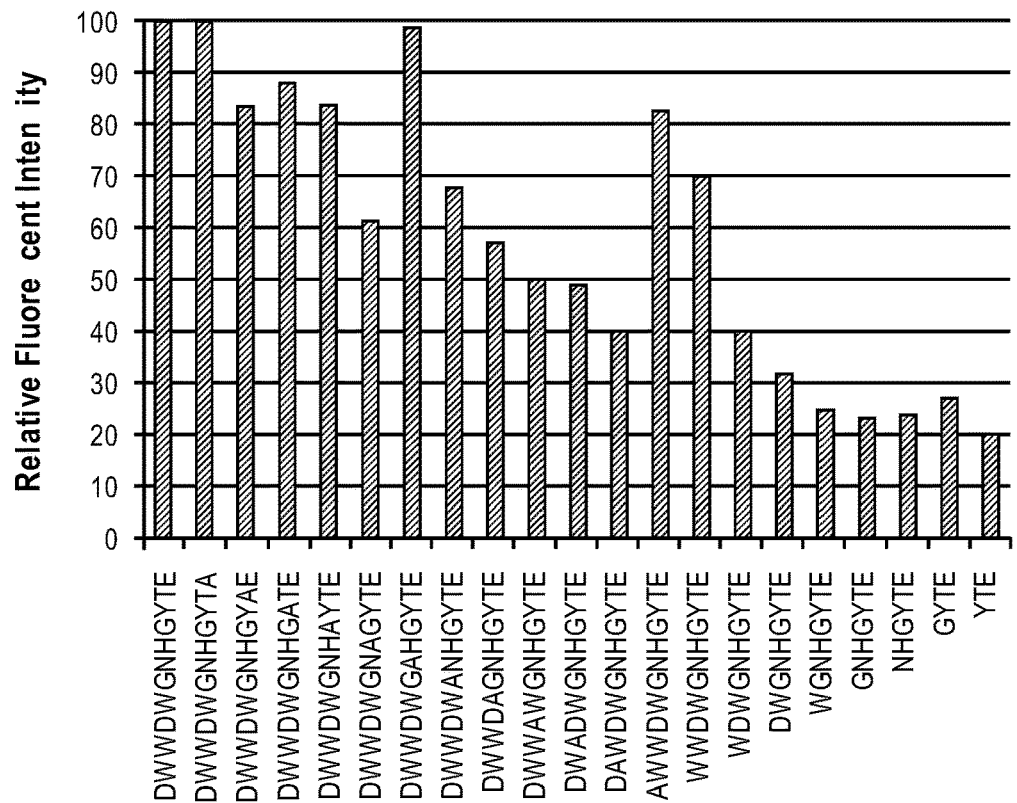
FIG. 9 shows the differences in fluorescent intensity detected in the alanine walk (A) and truncation (B) studies for peptide 12. Peptide 12 variants of the alanine walk experiment include peptides having amino acid sequences set forth in SEQ ID NOS:79-99. Peptide 12 deletions include peptides having the amino acid sequences set forth in SEQ ID NOS:79, 100-108 and 92-99, respectively.
Figure 9B:
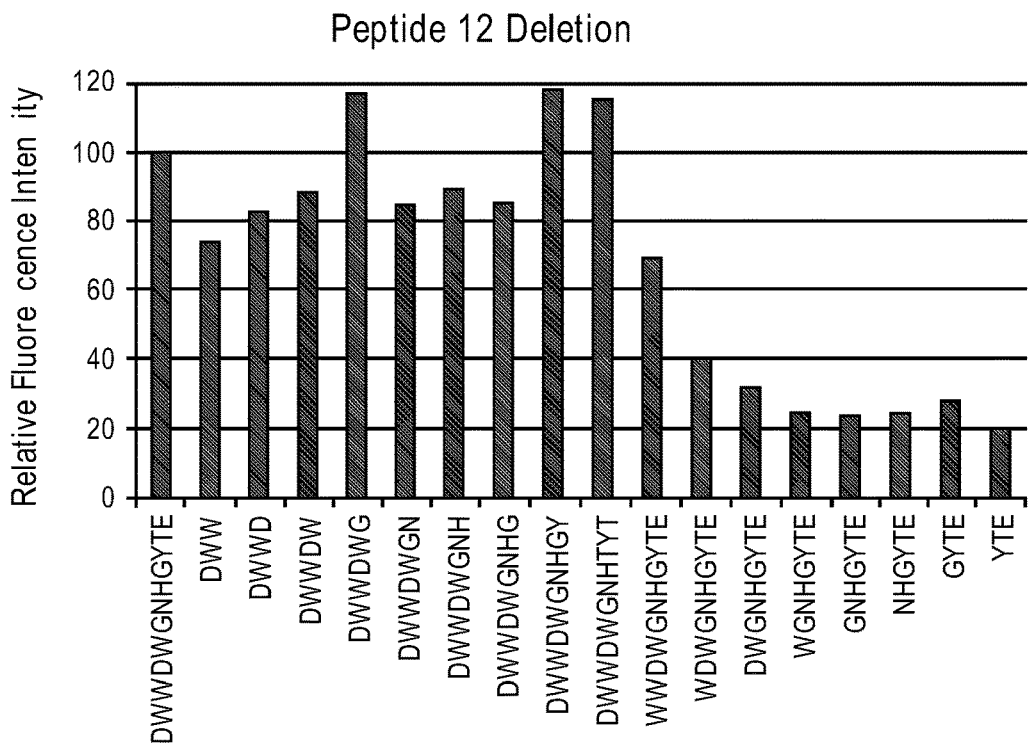
Figure 10A:
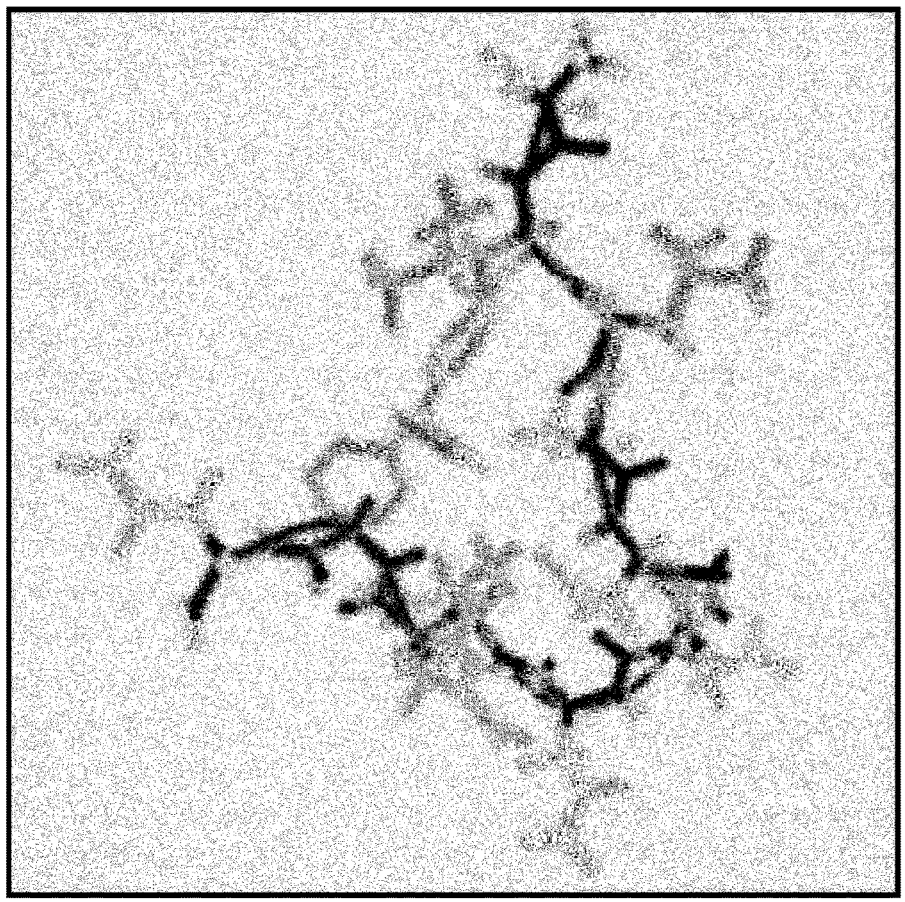
FIG. 10A shows the molecular docking of malachite green to peptide 12, as predicted by Atodock v4.0.
Figure 10B:
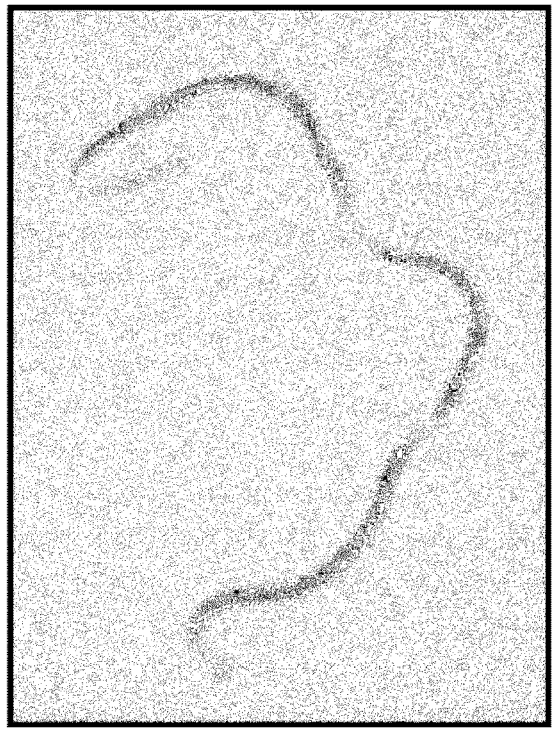
FIG. 10B shows the 3D structure of peptide 12.

Two peptides that can activate MG with or without calcium sensitivity were selected for further characterization. A solution form of the two peptides were synthesized and titrated with MG in the presence of 2 mM $Ca^{2+}$. Fluorescent signal at 650 nm was measured. The binding curve for peptide 12 (DWWDWGNHGYTE; SEQ ID NO:31), which follows one-site specific binding, with high affinity (Kd, ~410 pM), is shown in FIG. 8A. Computational modeling confirmed stably folded structure of peptide 12 upon MG binding, preventing intramolecular motions of MG (FIG. 8B, FIG. 10A, B). Alanine walk study on this peptide showed that amino acids in positions 2, 3, 4, 5, and 8 are crucial in binding to MG (FIG. 9A, B). The immobilized peptides on TentaGel beads were then titrated with an increasing amount of MG in the presence and absence of 2 mM $Ca^{2+}$. Fluorescent emission at 650 nm by each individual bead was measured. Calcium binding significantly increased the MG binding affinity of peptide 2 (DWWWDGFERLEE; SEQ ID NO:23) by 10-folds (FIG. 11A). Interestingly, peptide 2 has 5 acidic residues that can chelate $Ca^{2+}$ and therefore can explain why the fluorescent signal is $Ca^{2+}$ dependent. Computational modeling further confirmed that stably folded structure of peptide 2 only forms upon calcium binding (FIG. 11B).

Computational modeling suggested a helix structure for peptide 2 in a calcium free media. Molecular dynamic showed the C-terminus turn of the helix opens up in a calcium rich environment. C-terminus of the peptide has two Glu residues, which upon binding to $Ca^{2+}$ open up and provides a binding site for MG.

Figure 14A:
FIG. 14 shows the predicted 3D structure of peptide 2 (A) and the predicted 3D structure of the peptide after 20 ns of molecular docking relaxation with $Ca^{2+}$ ions (B).
Figure 14B:

In order to confirm the helix structure of peptide 2, CD spectrum of peptide 2 was acquired in the presence of chelex bead, which chelates all the $Ca^{2+}$ ions in the solution. The CD spectrum showed the formation of the helix in peptide 2, whereas peptide 12 did not show any specific structure (FIG. 12). The "alanine walk" and deletion SAR studies of peptide 2 revealed that almost all amino acids in the peptide are important for MG binding in the presence of $Ca^{2+}$ (FIG. 13A, B). Computational modeling shows the conformation change of peptide 2 due to $Ca^{2+}$ (FIG. 14A, B).

Characterize MG-activating Peptides in Living Cells

Figure 15:
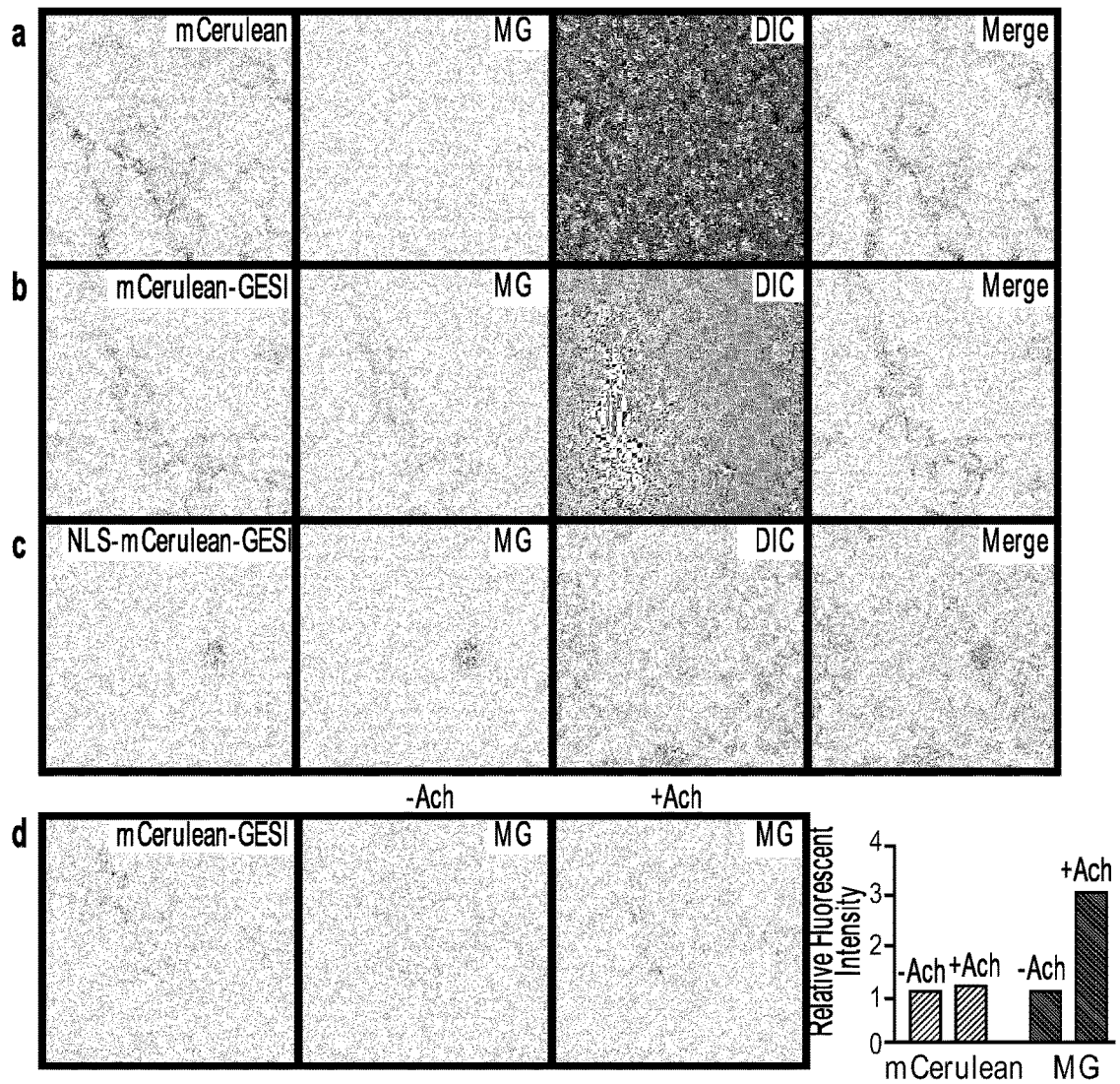
FIGS. 15A, 15B, 15C and 15D shows the fluorescent activity of MG-activating peptide fusion proteins in HEK293 cells. Scale bar: 10 mm.

To evaluate the utility of lead peptides in mammalian cells, individual peptide tags were fused to the C-terminus of a cyan fluorescence protein (Cerulean 3) anchored on the plasma membrane. An amino acid linker (GGSGSGGS: SEQ ID NO:33) was placed between C-terminus of Cerulean and the peptide to increase the solubility and stability of the recombinant fusion proteins. Goals for the design of fusion proteins are two-folds. First, the labeling ability of peptides can be readily detected by co-localization of both cyan and infrared fluorescence. Second, the calcium sensing ability of peptide can be tested by taking advantage of endogenous acetylcholine (Ach) receptors; Ach stimulus leads to transient calcium influx in cytosol, which may lead to increased MG fluorescence. Given the limited membrane permeability of MG, a relative high concentration of MG ($5 \times 10^{-7}$ M) was used for the imaging assay. 48 hrs post-transfection, time-lapse, dual-color confocal fluorescence microscopy images were taken upon MG incubation, followed by Ach addition. Four out of 11 lead peptides fused proteins showed clear co-localization of infrared and cyan fluorescence upon MG addition. The fluorescence intensity reached plateau within seconds and remains stable during the 10 mins period of imaging window. In contrast, no apparent infrared fluorescence was observed when membrane-anchored Cerulean control (without grafted peptide) was expressed upon MG addition (FIG. 15A). These results suggest that our two-step screening approach is effective to allow identification of peptide sequence for the development of functional GESIs in living cells. To explore the utility of GESIs in labeling subcellular proteins, we further targeted Cerulean-linker-GESIs fusion protein to the nucleus. Dual-color imaging revealed co-localization of cyan and infrared fluorescence on the cytoplasmic membrane (FIG. 15B), as well as in the nucleus (FIG. 15C), suggesting GESIs hold great promise to allow probing the localization of essential cytosolic and subcellular proteins. Calcium sensing ability was also observed upon acetylcholine (Ach) addition (FIG. 15D).

The example describes a method of using OBOC technology to discover new small illuminants that can be genetically encoded in living cells. Using the high through-put method of beads were screened in less than 10 min. Eleven positive beads were found and 2 of them were selectively characterized in vitro. Peptide 12 (DWWDWGNHGYTE; SEQ ID NO:31) showed a very strong binding to MG with 410 pM binding affinity. Peptide 2 (DWWWDGFERLEE; SEQ ID NO:23) with 5 carboxylic acid residues is more sensitive to calcium and its binding to MG increases about 10 fold in a calcium rich environment. The modeling studies on these two peptides support the fact that peptide 2 conformation changes from a helix to a loop in a calcium rich media, where it can bind to MG, whereas peptide 12 holds a loop conformation even without calcium where ducks very well to MG.

MG-activating peptides were further characterized in living cells. Dual-color imaging showed a perfect localization of the peptide bound to MG and Cerulean. Sub-cellular localization showed that GESIs can be a powerful tool for cell imaging. The sensitivity of peptide 2 was examined in the living cells using acetylcholine (Ach) where the fluorescence intensity of MG was increased 4-fold upon Ach addition.

One unique feature of GESIs is that the fluorescent signal of the exogenously added organic dye is activated only upon binding to the peptide, thus, in principle making the background staining very low.

Unlike phage-display or yeast display combinatorial peptide libraries which are limited by genetic code and variable expression efficiency of different proteins, OBOC approach allows us to design and synthesize highly focused peptide libraries for specific application. For instance, the EF-hand design and preferred Asp in the N-terminal half of peptide enables us to focus our discovery effort on calcium reporter; and from such library, peptide 12 was discovered. Since OBOC is totally synthetic, many post-translational modified residues (e.g., phosphorylation, acetylation, methylation, glycation, sulfation and sumoylation) can be readily incorporated into the library design. This is very difficult if not impossible with phage-display or yeast display methods. Such "post-translationally modified" libraries will allow us to discover a range of GESIs to probe many different post-translational modifications.

This data illustrates that a GESI can be used as a cellular biosensor and is compatible with modern imaging techniques, such as wide-field, confocal and high-resolution microscopy.

Example 3

Tracking Live Viral Particle Assembly in Real-time

Figure 16:
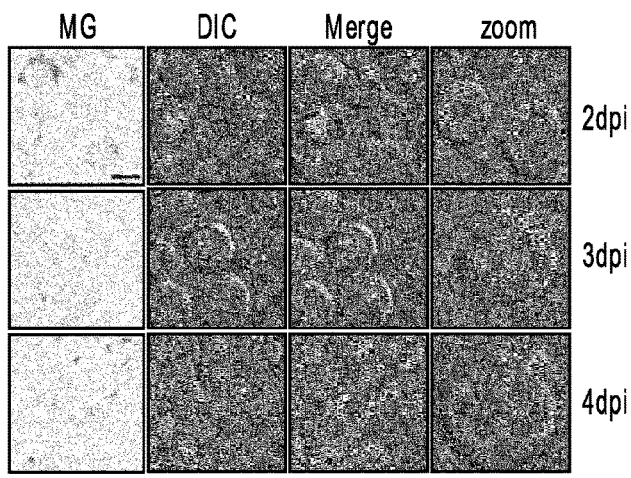
FIG. 16 shows images of fluorescence during viral particle assembly. Insect cells were infected with recombinant baculoviruses expressing a GESI fusion protein of a hepatitis E viral particle.

This example illustrates a method of using a GESI (genetically encoding small peptide illuminant) to track the packaging of viral particles in live cells. The method was used to study viral infection, in particular, the phases between protein synthesis and particle assembly. The GESI peptide (DSDSQGEYFHEE; SEQ ID NO: 34) was inserted into the dORF2 gene of the baculovirus transfer vector (pFastBac1/dORF2-HEV). The dORF2 encodes Hepatitis E viral particles. The recombinant baculovirus genome was purified from positive clones and used to transfect SF9 insect cells to produce recombinant baculovirus. Next, the recombinant baculovirus were used to infect Tn5 insect cell lines at a multiplicity of infection (m.o.i) of >5 and cultured for 1 to 6 days. Viral particle assembly was tracked using time-lapse microscopic imaging (FIG. 16). The data suggests that GESIs are capable of tracking the process of viral particle assembly in real-time.

Example 4

Figure 17B:
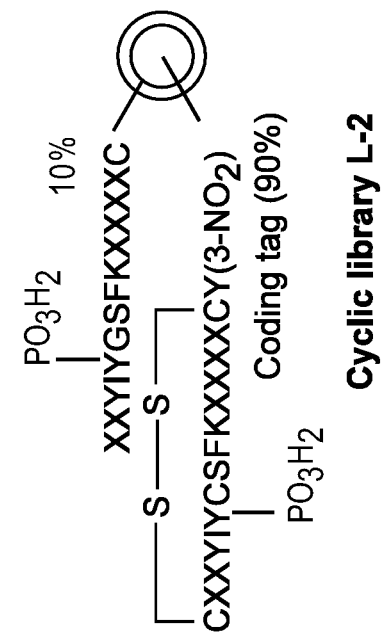
FIGS. 17A, 17B, 17C and 17D show exemplary embodiments of the peptide libraries described herein.
Figure 17D:
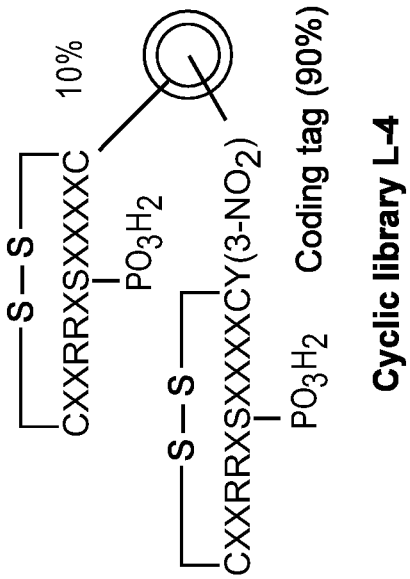
Figure 17A:
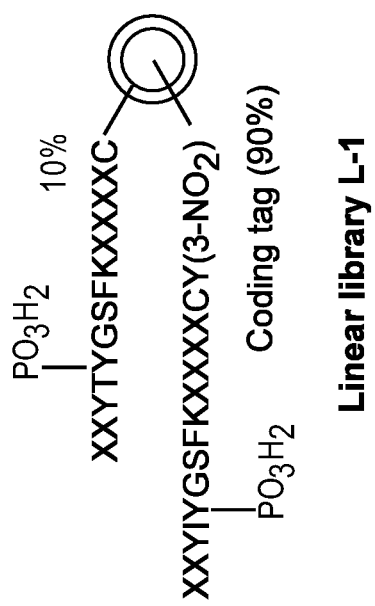

Screening OBOC Peptide Libraries to Identify MG-binding Phosphorylated Kinase Peptide Substrates YIYGSFK (SEQ ID NO:35) is a peptide substrate for protein tyrosine kinases, Btk, Etk and Src. In an effort to develop a sensitive method to detect intracellular phosphorylation of Btk, Etk and Src, a linear OBOC library L-1, XXYIY(PO$_3$H$_2$)GSFKXXXXC (SEQ ID NO: 36), and a cyclic OBOC library L-2, CXXYIY(PO₃H₂)GSFKXXXXC (SEQ ID NO:37) were designed. See, FIGS. 17A and 17B. In these libraries, a phosphorylated substrate YIY(PO₃H₂)GSFK (SEQ ID NO:38) was fixed in the middle and random natural amino acids excluding L-cysteine were placed at the two flanks. In order to minimize intrinsic auto-fluorescence from the beads, a quencher 3-nitro tyrosine was coupled to the inner layer of the library beads. The libraries were synthesized on TentaGel resin beads using the standard solid phase synthesis method and split-mix strategy. 6-Cl HOBt, HBTU and DIEA were used as coupling reagents. The coupling reaction lasted 2 h to overnight until the Kaiser test was negative. Side chain deprotection was achieved with trifluoroacetic acid (TFA) cocktail, reagent K.

About 100 μL of library beads from each of the two libraries (FIGS. 17A and 17B) were incubated with 5 μM MG in PBS overnight. Positive beads that bind to MG turned blue and were picked up and submitted for microsequencing decoding after wash. Five positive beads were identified from library L-1.

kinase A (PKA). In this case, RRXS(PO₃H₂) (SEQ ID NO:44) was used as the phosphorylated substrate. Two positive beads were identified from cyclic library L-4 and decoded. The result is shown in Table 2.

TABLE 4

MG-binding ligands from library L-4.

| | Amino Acid Sequence<br>S(P) denotes Ser(PO₃H₂) |
|---|---|
| SEQ ID NO: 45 | CMGRRPS(P)VDNNC |
| SEQ ID NO: 46 | CGVRRDS(P)WWYDC |

GESIs can be used as in vitro substrates for detecting kinase activities and in homogeneous assays for high throughput screening of protein kinase inhibitors.

TABLE 5

MG binding of peptide ligands from screening and their derivatives.

| SEQ ID NO: | No. | | | | Peptide sequence | | | | | | | | | | MG binding |
|---|---|---|---|---|---|---|---|---|---|---|---|---|---|---|---|
| 47 | 1 | | D | D | Y | I | Y(P) | G | S | F | K | P | Y | I | A | C | + |
| 48 | 2 | | D | V | Y | I | Y(P) | G | S | F | K | N | D | Y | I | C | ++ |
| 49 | 3 | | D | N | Y | I | Y(P) | G | S | F | K | P | W | E | W | C | +++ |
| 50 | 4 | | D | V | Y | I | Y(P) | G | S | F | K | Y | W | P | A | C | ++ |
| 51 | 5 | | D | T | Y | I | Y(P) | G | S | F | K | V | N | P | D | C | ++ |
| 52 | 1-D | | | D | Y | I | Y(P) | G | S | F | K | P | Y | I | A | C | - |
| 53 | 2-D | | | V | Y | I | Y(P) | G | S | F | K | N | D | Y | I | C | - |
| 54 | 3-D | | | N | Y | I | Y(P) | G | S | F | K | P | W | E | W | C | - |
| 55 | 4-D | | | V | Y | I | Y(P) | G | S | F | K | Y | W | P | A | C | - |
| 56 | 5-D | | | T | Y | I | Y(P) | G | S | F | K | V | N | P | D | C | - |
| 57 | 1-P | | D | D | Y | I | Y | G | S | F | K | P | Y | I | A | C | - |
| 58 | 2-P | | D | V | Y | I | Y | G | S | F | K | N | D | Y | I | C | + |
| 59 | 3-P | | D | N | Y | I | Y | G | S | F | K | P | W | E | W | C | ++ |
| 60 | 4-P | | D | V | Y | I | Y | G | S | F | K | Y | W | P | A | C | - |
| 61 | 5-P | | D | T | Y | I | Y | G | S | F | K | V | N | P | D | C | - |
| 62 | 1C | C | D | D | Y | I | Y(P) | G | S | F | K | P | Y | I | A | C | ++++ |
| 63 | 2C | C | D | V | Y | I | Y(P) | G | S | F | K | N | D | Y | I | C | ++++ |
| 64 | 3C | C | D | N | Y | I | Y(P) | G | S | F | K | P | W | E | W | C | ++++ |
| 65 | 4C | C | D | V | Y | I | Y(P) | G | S | F | K | Y | W | P | A | C | ++++ |
| 66 | 5C | C | D | T | Y | I | Y(P) | G | S | F | K | V | N | P | D | C | +++ |

11 hour incubation with 5 μM MG in PBS buffer (pH 7.4).
Y(P): Tyr(PO₃H₂);
−: no binding;
+: weak binding;
++: mild binding;
+++: strong binding;
++++: very strong binding.

TABLE 3

MG-binding ligands from library L-1.

| | Amino Acid Sequence<br>Y(P) denotes Tyr(PO₃H₂) |
|---|---|
| SEQ ID NO: 39 | DDYIY(P)GSFKPYIAC |
| SEQ ID NO: 40 | DVYIY(P)GSFKNDYIC |
| SEQ ID NO: 41 | DNYIY(P)GSFKPWEWC |
| SEQ ID NO: 42 | DVYIY(P)GSFKYWPAC |
| SEQ ID NO: 43 | DTYIY(P)GSFKVNPDC |

Figure 17C:
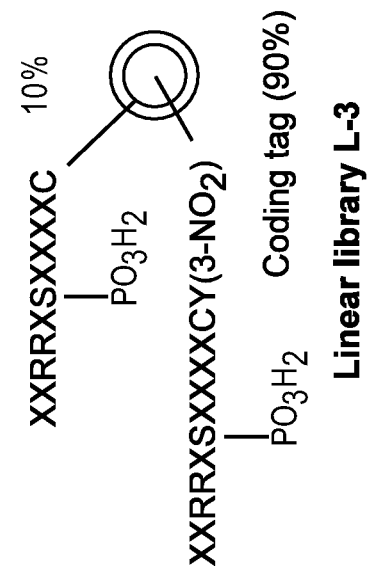

A similar strategy was used to design, synthesize and screen two OBOC libraries (FIGS. 17C and 17D) for protein Table 5 shows that the phosphorylated form, but not the unphosphorylated form of peptides 1, 4 and 5 bound MG, and that cyclization of the peptides further enhanced the fluorescent intensity.

Based on the result, a high throughput homogenous protein kinase activity assay was developed by adding the peptide substrate together with malachite green and Mg-ATP into multi-titer wells containing a protein kinase (e.g., src protein tyrosine kinase) and a putative kinase inhibitor (chemical library compound). Peptide phosphorylation was indicated by a fluorescent signal using a real time or end-point assay. Low fluorescent signal indicated kinase inhibition.

This example describes a highly efficient homogenous assay that does not require washing of the assay plate. In addition, this assay can be easily applied to in situ releasable assay using the one-bead-one-compound combinatorial library format. In this method the peptide substrate was immobilized to a gel matrix and the library compounds were released from each library bead. Circular zones of inhibition of fluorescence reflected the potency of the kinase inhibitors released from each bead.

Example 5

Preparation of Peptides for Probing Protein Kinase Activity

This example is an illustrative embodiment of the present invention. In particular, it describes a method for generating a protein localization probe for protein kinase activity.

This example summarizes some of the OBOC designs and screening approaches used in the discovery of GESIs suitable for probing a wide range of biochemical and cellular functions, such as protein kinase activity (see, FIG. 18).

Library category 1 was a standard linear 10-mer and 12-mer OBOC peptide library comprised of 20 eukaryotic amino acids. In some libraries, cysteine as eliminated from the repertoire of building blocks to avoid disulfide bond formation. Beads that interact with MG or other selected organic dyes, leading to near infra-red fluorescence, were isolated for decoding using microsequencing or mass spectrometry analysis. GESIs that were developed from these peptide sequences were used as genetic tags to localize intracellular proteins or to track their trafficking in real time in living cells in multiplex fashion. In library category 2, two random segments of peptides (e.g., 5-6 mer) were linked together by a highly flexible and hydrophilic PEG linker (~1000 daltons) such that one peptide segment has the opportunity to fold back to interact with MG and the other peptide segment to form a ternary complex and result in fluorescence. In some experiments, we added 2-3 Leu residues at the N-terminus and C-terminus of the peptides so that such "short leucine zipper" facilitated the formation of ternary complex with the dye. Such peptide pairs were used for the development of GESIs to probe protein-protein interactions and conformational changes of proteins. In library category 3, a range of OBOC libraries were designed to screen for peptides that binds to MG or other dyes after undergoing specific post-translational modifications such as phosphorylation, acetylation, methylation, sulfation, ubiquitination and sumoylation. In some experiments library design were totally random except for fixation of e.g., Tyr, Ser or Thr in the middle of the random peptide segment, which can be phosphorylated in vitro with specific PKs prior to screening with MG. If peptide substrate motifs were known, they were also incorporated into the libraries. During the screening process, these diverse and focused linear libraries were pre-treated with the post-translational modification enzyme of interest (e.g., PKA) to introduce the modification to the peptides displayed on the library beads. Following this, the library beads were probed for MG binding and infra-red fluorescence. In some experiments, pre-phosphorylated OBOC libraries were chemically prepared and screened directly for MG binding and infra-red fluorescence. The advantage of this approach is that potential substrate peptides for kinases are enriched in these libraries, therefore chances of identifying MG binding putative kinase substrates are much higher. Furthermore, the experiments does not require the post-translational enzyme which may not be readily available. Using this approach, many post-translational modifications (phosphorylation, methylation, acetylation, etc.) were combinatorially incorporated into the library using chemical approaches. A schematic representation of the PK reporter design is shown in FIG. 19.

XXXXART(P)K(Me)$_{0-3}$QT (SEQ ID NO:67) is one example in which different modifications on specific residues were incorporated in any possible combinations into random library. The first four amino acids are random, the remaining amino acids (residue 5 to 10) represent the N-terminal 6 amino acids of Histone H3.

This example illustrates a highly versatile genetically encoded reporter system that (i) allows one to monitor the dynamics of any desired proteins that undergo post-translational modifications, in real time in living cells and in living animals, so that spatiotemporal regulation of these proteins can be determined, (ii) allow compatibility with modern imaging techniques, such as wide-field, confocal and high-resolution microscopy, as well as stochastic optical reconstruction microscopy (STORM), and (iii) to monitor a number of post-translational modifications concurrently in a multiplex manner to reveal system level regulations.

Example 6

Preparation of Peptides for Probing Histone Modifications

This example is an illustrative embodiment of the present invention. In particular, it describes a method for generating a peptide useful for probing histone modifications.

The peptides of the present invention can be used in the study of epigenetics. For instance, genetically encoded functional illuminants are useful for mapping of epigenetic marks, especially histone modifications, during cellular events in living cells. Changes in epigenetic mechanisms can be hallmarks of particular diseases, such as cancer and neuro-developmental diseases. These peptides allow simultaneous detection of global modification events within the single histone during cellular events in living cells, thus decoding the epigenetic marks.

Figure 20E:
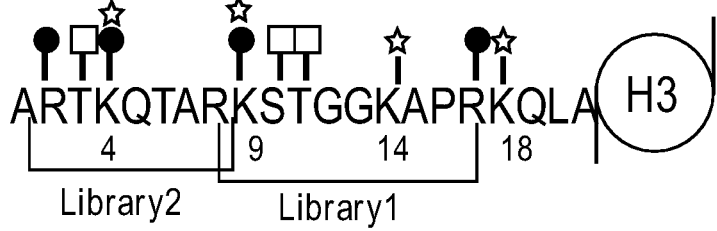

An OBOC combinatorial library was prepared for the development of GESIs for probing histone H2 tail. The library design is shown in FIG. 20C, wherein X represents all 20 eukaryotic amino acids except for cysteine; all possible post-translational modification states of Ser-1 and Lys-5 are incorporated; and additional Xs at the N-terminus of the histone tail will provide necessary capturing residues for fluorescent dyes. From this library, we have identified four DMHBI activating peptides (library peptide fused to N-terminal H2, FIG. 20C,D): DPSWPNS(P)GRGK(Ac) (SEQ ID NO:68), TRPSMWS(P)GRGK(Ac) (SEQ ID NO:69), VWDGIRS(P)GRGK(Ac) (SEQ ID NO:70), and GLFDQES(P)GRGK (SEQ ID NO:71). One Ser was phosphorylated and Lys-5 was acetylated in 3 of these 4 fusion peptides, whereas Lys-5 was non-acetylated in the remaining peptide, indicating that GESIs capable of probing various epigenetic functional status of histone tail can be developed by the method described herein.

FIGS. 20A-E shows the library design of GESIs directed to histone epigenetics. The library includes peptides based on H3, H2A, H2B and/or H4 histone modification site. Exemplary examples of the amino acid sequences of the H3 histone tail include, but are not limited to, RKSTG (SEQ ID NO:214) and GKAPR (SEQ ID NO: 215).

This example shows a method for generating a GESI to probe histone modifications, wherein a short peptide is inserted into a histone protein.

Example 7

Post-translational Modification of OBOC Libraries

This example is an illustrative embodiment of the present invention. In particular, it describes a method for generating peptides with post-translational modifications.

Screening for Library category 2 (Table 2) necessitates that the entire OBOC bead library array be scanned with and without MG or other dyes, before and after PTM. Here, we will use c-src PTK as an example. We have previously reported the use of OBOC combichem and radiosubstrate screening method to identify an efficient and specific peptide substrate (YIYGSFK; SEQ ID NO:35) for c-src PTK. We have later found that addition of two more Lys to the C-terminus further improved the efficiency of this substrate. Recently, we prepared YIY(P)GSFKKKX$_n$ (SEQ ID NO:216) libraries (X=all 19 L-amino acids except Cys, n=6-9) and screened them against MG. After 1 hr incubation, near-infra-red image of the entire immobilized library was captured. The bead library was then thoroughly washed, and dephosphorylated with 50% HF. Beads that strongly fluoresce near infra-red before dephosphorylation but fluoresce weakly (or none) after dephosphorylation were selected as candidate GESIs for c-src PTK (Table 6). Of these 8 peptides isolated from screening ~300,000 beads, 3 has 1 Trp, and the remaining 5 have no Trp. Work is currently underway to characterize their substrate efficiency and specificity biochemically in a cell-free system and subsequently inside living cells. In principle, using various dyes and PKs to screen OBOC libraries, we should be able to develop several GESIs against several PKs that can be multiplexed with different dyes in living cells. We have developed GESIs for one serine/threonine kinase (PKA), and two tyrosine kinases (c-src and bcr-abl). Very recently, we have designed another library with a c-abl motif ("Abltide"): EAIY(P)AAPFAKKX$_n$ (SEQ ID NO:217).

TABLE 6

Result of YIY(P)GSFKKKX(6-9) (SEQ ID NO: 216) library screening for GESI reporter* against c-src PTK
(SEQ ID NOS: 154, 218, 219, 156, 220, 158, 221 and 160)

| | X9 | X8 | X7 | X6 | X5 | X4 | X3 | X2 | X1 |
|---|---|---|---|---|---|---|---|---|---|
| X6-1 | | | | Y | F | G | V | H | S |
| X6-3 | | | | E | Q | Y | Y | Q | W |
| X7-1 | | | D | Y | V | F | A | L | Y |
| X7-6 | | | Y | F | N | A | I | N | T |
| X8-1 | | I | F | T | Q | N | I | Y | I |
| X8-2 | | N | Y | T | W | Y | V | S | Y |
| X8-3 | | D | Q | E | F | T | A | F | M |
| X9-1 | D | R | M | F | T | T | W | S | D |

*Add YIY(P)GSFKKK (SEQ ID NO: 222) to N-terminus of these sequences

Figure 21A:
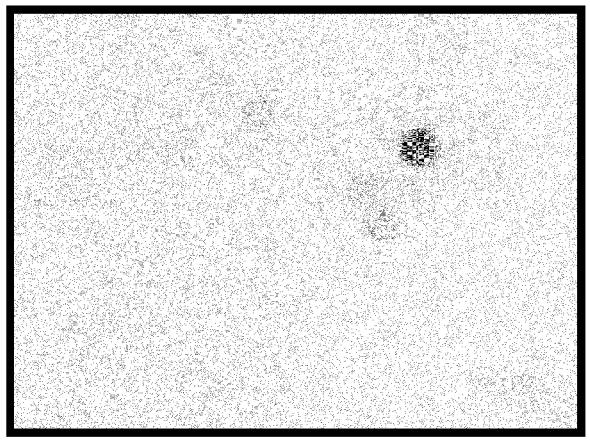
FIGS. 21A and 21B show screening of OBOC library with Abltide motif showing the highly positive EAIY(P)AAP-FAKKLYIMDGWF (SEQ ID NO:165) bead (LLT4, arrow) (A) before and (B) after dephosphorylation.
Figure 21B:
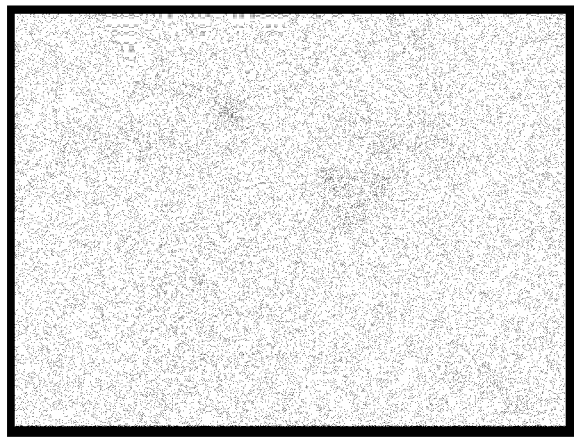

After screening about one million beads with MG, we identified four peptides that greatly activate MG in phosphorylated but not dephosphorylated form (Table 7). Photomicrograph of LLT4bead is shown in FIG. 21, with a marked decrease in fluorescent signal (relative arbitrary level of 1930 to 93 and a ΔF/F value of 19; see right columns of Table 7) after dephosphorylation (treatment with 50% HF). High consensus was observed. All 4 beads have a Tyr at $X_7$, a negative-charged amino acid at $X_4$, hydrophobic amino acids at $X_1$, $X_6$ and $X_8$ (3 out 4 have Val at $X_6$ and Tyr at $X_8$). Three out four beads have a positive-charged amino acid at $X_2$ position. To discover GESIs for PKA, we will include the known PKA substrate motif (RRX[S/T]; SEQ ID NO:223) into the OBOC libraries. In some libraries, the known kinase substrate motifs will be placed between two stretches of random residues. In some cases, we have found increased (instead of decrease) fluorescence after dephosphorylation. These peptides are potential leads for developing phosphatase sensors.

TABLE 7

Screening result of OBOC library with Abltide motif designed for the discovery of GESI for c-abl and bcr-abl PTKs (SEQ ID NO: 224-226 and 165)

| | X$_{19}$ | X$_{18}$ | X$_{17}$ | X$_{16}$ | X$_{15}$ | X$_{14}$ | X$_{13}$ | X$_{12}$ | X$_{11}$ | X$_{10}$ | X$_9$ | X$_8$ | X$_7$ | X$_6$ | X$_5$ | X$_4$ | X$_3$ | X$_2$ | X$_1$ | Pre-dephos | Post-dephos | ΔF/F |
|---|---|---|---|---|---|---|---|---|---|---|---|---|---|---|---|---|---|---|---|---|---|---|
| LLT1 | E | A | I | Y(P) | A | A | P | F | A | K | K | Y | Y | V | Y | D | M | H | I | 939 | 72 | 12 |
| LLT2 | E | A | I | Y(P) | A | A | P | F | A | K | K | Y | Y | V | Q | D | S | R | A | 575 | 44 | 12 |
| LLT3 | E | A | I | Y(P) | A | A | P | F | A | K | K | Y | Y | V | S | E | R | K | W | 835 | 63 | 12 |
| LLT4 | E | A | I | Y(P) | A | A | P | F | A | K | K | L | Y | I | M | D | G | W | F | 1930 | 93 | 19 |

Fluorescent Bead Detection, Isolation, and Structure Determination: Individual positive beads (candidate GESIs) will be localized, retrieved from the bead array, treated with 6M guanidine HCl (pH 1.0) and 50% DMF/H$_2$O to strip all bound dyes/proteins prior to microsequencing (ABI Procise 494). Alternatively, mass spectroscopy can be used for chemical decoding as previously reported. The latter method is faster. Substrate specificity will be examined by in vitro phosphorylation assay with different PKs.

We have had substantial experience in OBOC combinatorial libraries synthesis and screening, as well as PK and protein tyrosine sulfo-transferase substrate identification.[23-27] We therefore do not anticipate any technical difficulties in accomplishing the OBOC library aspect of the project. We expect to generate a toolbox of functional illuminant peptides that can be used in a broad range of biological applications. Translating the peptides identified in aim 1 to highly sensitive and specific functional illuminants in living cells, however, is more challenging. In this proposal, we will characterize the utility of these peptides in live cells with an emphasis on phosphorylation (Aim 2) and histone epigenetics (Aim 3). As indicated above, we plan to design and synthesize a series of dyes candidates for GESI development. We are cognizant that many organic dyes bind non-specifically to many proteins, but usually at rather high concentration (mM). Prior to investing time and effort in screening, we will need to ensure that the dyes are non-toxic and does not stain mammalian cells and tissues to any significant extent at the range of dye concentration we intent to use (e.g. 1-100 nM). It is also important to realize that not all binding events will activate fluorescence. In fact during bead screening experiment with MG, high affinity binding (indicated by dark green color bead) does not always correlate with strong near-red fluorescence. This works in our favor as not all non-specific binding (if there is any) will lead to activation of the dyes. One concern that the previous reviewers have was the large number of Trp in our initial leads (e.g. LTA2 and LTA10). As shown in the preliminary data, many strong activators for MG have low number of Trp. For example, fluorescent activation of MG by LRRAS (P)LFYGMWYPST (SEQ ID NO:227), with only 1 Trp, is 4-5× brighter than that of LTA2 and LTA10.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

Informal Sequence Listing

```
                                           SEQ ID NO: 1
XXX(X)$_n$RRXS(X)$_n$XXX, wherein X is any amino acid
residue, n is 1 to 6 amino acid residues, and
serine (S) can be phosphorylated.

SEQ ID NO: 2
XX(X)$_n$RRXT(X)$_n$XXXX, wherein X is any amino acid
residue, n is 1 to 6 amino acid residues, and
threonine (T) can be phosphorylated.

SEQ ID NO: 3
XXXX(X)$_n$S(X)$_n$XXXX, wherein X is any amino acid
residue, n is 1 to 6 amino acid residues, and
serine (S) can be phosphorylated.

SEQ ID NO: 4
XXXX(X)$_n$T(X)$_n$XXXX, wherein X is any amino acid
residue, n is 1 to 6 amino acid residues, and
threonine (T) can be phosphorylated.

SEQ ID NO: 5
XXX(X)$_n$SP(X)$_n$XXX, wherein X is any amino acid
residue, n is 1 to 6 amino acid residues, and
serine (S) can be phosphorylated.

SEQ ID NO: 6
XXX(X)$_n$TP(X)$_n$XXX, wherein X is any amino acid
residue, n is 1 to 6 amino acid residues, and
threonine (T) can be phosphorylated.

SEQ ID NO: 7
RKSTTG(X)$_n$GKAPR, wherein n is 1 to 10 amino acid
residues, serine (S) or threonine (T) can be
phosphorylated, lysine (K) can be acetylated
or methylated.

SEQ ID NO: 8
(X)$_n$ARTKQTAR, wherein X is any amino acid residue,
n is 1 to 10 amino acid residues, serine (S) or
threonine (T) can be phosphorylated, lysine (K)
can be acetylated or methylated.

SEQ ID NO: 9
(X)$_n$SGRGKQG, wherein X is any amino acid residue,
n is 1 to 10 amino acid residues, serine (S) or
threonine (T) can be phosphorylated, lysine (K)
can be acetylated or methylated.

SEQ ID NO: 10
DX$_d$X$_d$X$_d$X$_d$GXXXXXE-bead, wherein
X and X$_d$ are any amino acid residue except
cysteine.

SEQ ID NO: 11
CNSPDIC

SEQ ID NO: 12
CQPDLTC

SEQ ID NO: 13
CGNTEPC

SEQ ID NO: 14
CMTQEAC

SEQ ID NO: 15
CLSDEFC

SEQ ID NO: 16
CHTHILC

SEQ ID NO: 17
CHPLLPC

SEQ ID NO: 18
CEIHRIC

SEQ ID NO: 19
CLMNKWC

SEQ ID NO: 20
CYKWWVC

SEQ ID NO: 21
CKWILPC

SEQ ID NO: 22
DILDDGDEIQGE
```

SEQ ID NO: 23
DWWWDGFERLEE

SEQ ID NO: 24
DRDGDGDHRKIE

SEQ ID NO: 25
DSDSWGEYFHEE

SEQ ID NO: 26
DFMRQGVYDIPE

SEQ ID NO: 27
DDYDDGWIYEFE

SEQ ID NO: 28
DGDDGGYWPFPE

SEQ ID NO: 29
DEWHDGMEGNLE

SEQ ID NO: 30
DSKDPGMTHLKE

SEQ ID NO: 31
DWWDWGNHGYTE

SEQ ID NO: 32
DAQWMGANMHTE

SEQ ID NO: 33
GGSGSGGS

SEQ ID NO: 34
DSDSQGEYFHEE

SEQ ID NO: 35
YIYGSFK

SEQ ID NO: 36
XXYIY($PO_3H_2$)GSFKXXXXC, wherein tyrosine (Y) is phosphorylated ($PO_3H_2$).

SEQ ID NO: 37
CXXYIY($PO_3H_2$)GSFKXXXXC, wherein tyrosine (Y) is phosphorylated ($PO_3H_2$).

SEQ ID NO: 38
YIY($PO_3H_2$)GSFK, wherein tyrosine (Y) is phosphorylated ($PO_3H_2$).

SEQ ID NO: 39
DDYIY(P)GSFKPYIAC, wherein Y(P) denotes Tyr($PO_3H_2$) or a phosphorylated tyrosine residue.

SEQ ID NO: 40
DVYIY(P)GSFKNDYIC, wherein Y(P) denotes Tyr($PO_3H_2$) or a phosphorylated tyrosine residue.

SEQ ID NO: 41
DNYIY(P)GSFKPWEWC, wherein Y(P) denotes Tyr($PO_3H_2$) or a phosphorylated tyrosine residue.

SEQ ID NO: 42
DVYIY(P)GSFKYWPAC, wherein Y(P) denotes Tyr($PO_3H_2$) or a phosphorylated tyrosine residue.

SEQ ID NO: 43
DTYIY(P)GSFKVNPDC, wherein Y(P) denotes Tyr($PO_3H_2$) or a phosphorylated tyrosine residue.

SEQ ID NO: 44
RRXS($PO_3H_2$), wherein the serine residue is phosphorylated.

SEQ ID NO: 45
CMGRRPS(P)VDNNC, wherein S(P) denotes Ser($PO_3H_2$) or a phosphorylated serine residue.

SEQ ID NO: 46
CGVRRDS(P)WWYDC, wherein S(P) denotes Ser($PO_3H_2$) or a phosphorylated serine residue.

SEQ ID NO: 47
DDYIY(P)GSFKPYIAC, wherein Y(P) denotes Tyr($PO_3H_2$) or a phosphorylated tyrosine residue.

SEQ ID NO: 48
DVYIY(P)GSFKNDYIC, wherein Y(P) denotes Tyr($PO_3H_2$) or a phosphorylated tyrosine residue.

SEQ ID NO: 49
DNYIY(P)GSFKPWEWC, wherein Y(P) denotes Tyr($PO_3H_2$) or a phosphorylated tyrosine residue.

SEQ ID NO: 50
DVYIY(P)GSFKYWPAC, wherein Y(P) denotes Tyr($PO_3H_2$) or a phosphorylated tyrosine residue.

SEQ ID NO: 51
DTYIY(P)GSFKVNPDC, wherein Y(P) denotes Tyr($PO_3H_2$) or a phosphorylated tyrosine residue.

SEQ ID NO: 52
DYIY(P)GSFKPYIAC, wherein Y(P) denotes Tyr($PO_3H_2$) or a phosphorylated tyrosine residue.

SEQ ID NO: 53
VYIY(P)GSFKNDYIC, wherein Y(P) denotes Tyr($PO_3H_2$) or a phosphorylated tyrosine residue.

SEQ ID NO: 54
NYIY(P)GSFKPWEWC, wherein Y(P) denotes Tyr($PO_3H_2$) or a phosphorylated tyrosine residue.

SEQ ID NO: 55
VYIY(P)GSFKYWPAC, wherein Y(P) denotes Tyr($PO_3H_2$) or a phosphorylated tyrosine residue.

SEQ ID NO: 56
TYIY(P)GSFKVNPDC, wherein Y(P) denotes Tyr($PO_3H_2$) or a phosphorylated tyrosine residue.

SEQ ID NO: 57
DDYIYGSFKPYIAC

SEQ ID NO: 58
DVYIYGSFKNDYIC

SEQ ID NO: 59
DNYIYGSFKPWEWC

SEQ ID NO: 60
DVYIYGSFKYWPAC

SEQ ID NO: 61
DTYIYGSFKVNPDC

SEQ ID NO: 62
CDDYIY(P)GSFKPYIAC, wherein Y(P) denotes Tyr($PO_3H_2$) or a phosphorylated tyrosine residue.

SEQ ID NO: 63
CDVYIY(P)GSFKNDYIC, wherein Y(P) denotes Tyr($PO_3H_2$) or a phosphorylated tyrosine residue.

SEQ ID NO: 64
CDNYIY(P)GSFKNPWEWC, wherein Y(P) denotes Tyr($PO_3H_2$) or a phosphorylated tyrosine residue.

SEQ ID NO: 65
CDVYIY(P)GSFKYWPAC, wherein Y(P) denotes Tyr($PO_3H_2$) or a phosphorylated tyrosine residue.

SEQ ID NO: 66
CDTYIY(P)GSFKVNPDC, wherein Y(P) denotes Tyr($PO_3H_2$) or a phosphorylated tyrosine residue.

SEQ ID NO: 67
XXXXART(P)K(Me)$_{0-3}$QT, wherein T(P) denotes a phosphorylated threonine residue and K(Me)$_{0-3}$ denotes that the lysine can have unmethylated or methylated once, twice or thrice.

SEQ ID NO: 68
DPSWPNS(P)GRGK(Ac), wherein S(P) is a phosphorylated serine residue and K(Ac) is an acetylated lysine residue.

SEQ ID NO: 69
TRPSMWS(P)GRGK(Ac), wherein S(P) is a phosphorylated serine residue and K(Ac) is an acetylated lysine residue.

SEQ ID NO: 70
VWDGIRS(P)GRGK(Ac), wherein S(P) is a phosphorylated serine residue and K(Ac) is an acetylated lysine residue.

SEQ ID NO: 71
GLFDQES(P)GRGK, wherein S(P) is a phosphorylated serine residue.

SEQ ID NO: 72
XXXRRXSXX

SEQ ID NO: 73
XXXXXTPXXX

SEQ ID NO: 74
DXXXXGXXXXE

SEQ ID NO: 75
X(n)SGRGKQG, wherein X is any amino acid residue, n is 1 to 10 amino acid residues, the serine residue (S) can be phosphorylated or unphosphorylated, and the lysine residue (K) can be acetylated.

SEQ ID NO: 76
ARTKQTARKSTGGKAPRKQLA

SEQ ID NO: 77
RKSTTG(X)nGKAPR, wherein X is any amino acid residue, n is 1 to 10 amino acid residues, the serine residue (S) can be phosphorylated or unphosphorylated, the first threonine residue (T) can be phosphorylated or unphosphorylated, any lysine residue (K) can be acetylated, unmethylated or methylated once, twice or thrice, or any combination thereof.

SEQ ID NO: 78
(X)nARTKQTAR, wherein X is any amino acid residue, n is 1 to 10 amino acid residues, the first threonine residue (T) can be phosphorylated or unphosphorylated, any lysine residue (K) can be unmethylated or methylated once, twice or thrice, or any combination thereof

SEQ ID NO: 79
DWWDWGNHGYTE

SEQ ID NO: 80
DWWDWGNHGYTA

SEQ ID NO: 81
DWWDWGNHGYAE

SEQ ID NO: 82
DWWDWGNHGATE

SEQ ID NO: 83
DWWDWGNHAYTE

SEQ ID NO: 84
DWWDWGNAGYTE

SEQ ID NO: 85
DWWDWGAHGYTE

SEQ ID NO: 86
DWWDWANHGYTE

SEQ ID NO: 87
DWWDAGNHGYTE

SEQ ID NO: 88
DWWAWGNHGYTE

SEQ ID NO: 89
DWADWGNHGYTE

SEQ ID NO: 90
DAWDWGNHGYTE

SEQ ID NO: 91
AWWDWGNHGYTE

SEQ ID NO: 92
WWDWGNHGYTE

SEQ ID NO: 93
WDWGNHGYTE

SEQ ID NO: 94
DWGNHGYTE

SEQ ID NO: 95
WGNHGYTE

SEQ ID NO: 96
GNHGYTE

SEQ ID NO: 97
NHGYTE

SEQ ID NO: 98
GYTE

SEQ ID NO: 99
YTE

SEQ ID NO: 100
DWW

SEQ ID NO: 101
DWWD

SEQ ID NO: 102
DWWDW

SEQ ID NO: 103
DWWDWG

SEQ ID NO: 104
DWWDWGN

SEQ ID NO: 105
DWWDWGNH

SEQ ID NO: 106
DWWDWGNHG

SEQ ID NO: 107
DWWDWGNHGY

SEQ ID NO: 108
DWWDWGNHGYT

SEQ ID NO: 109
DWWWDGFERLEE

SEQ ID NO: 110
DWWWDGFERLEA

DWWWDGFERLAE          SEQ ID NO: 111

DWWWDGFERAEE          SEQ ID NO: 112

DWWWDGFEALEE          SEQ ID NO: 113

DWWWDGFARLEE          SEQ ID NO: 114

DWWWDGAERLEE          SEQ ID NO: 115

DWWWDAFERLEE          SEQ ID NO: 116

DWWWAGFERLEE          SEQ ID NO: 117

DWWADGFERLEE          SEQ ID NO: 118

DWAWDGFERLEE          SEQ ID NO: 119

DAWWDGFERLEE          SEQ ID NO: 120

AWWWDGFERLEE          SEQ ID NO: 121

DWWWDFERLEE           SEQ ID NO: 122

LEE                   SEQ ID NO: 123

RLEE                  SEQ ID NO: 124

ERLEE                 SEQ ID NO: 125

FERLEE                SEQ ID NO: 126

GFERLEE               SEQ ID NO: 127

DGFERLEE              SEQ ID NO: 128

WDFERLEE              SEQ ID NO: 129

WWDFERLEE             SEQ ID NO: 130

WWWDFERLEE            SEQ ID NO: 131

DWWWDGFERLE           SEQ ID NO: 132

DWWWDGFERL            SEQ ID NO: 133

DWWWDGFER             SEQ ID NO: 134

DWWWDGFE              SEQ ID NO: 135

DWWWDGF               SEQ ID NO: 136

DWWWDG                SEQ ID NO: 137

DWWWD                 SEQ ID NO: 138

DWWW                  SEQ ID NO: 139

XXYIYGSFKXXXXC, wherein the second Y residue can be phosphorylated.          SEQ ID NO: 140

XXYIYGSFKXXXXCY, wherein the second Y residue can be phosphorylated.         SEQ ID NO: 141

CXXYIYGSFKXXXXCY, wherein the second Y residue can be phosphorylated.        SEQ ID NO: 142

XXRRXSXXXXC, wherein the serine residue can be phosphorylated.               SEQ ID NO: 143

XXRRXSXXXXCY, wherein the serine residue can be phosphorylated.              SEQ ID NO: 144

CXXRRXSXXXXC, wherein the serine residue can be phosphorylated.              SEQ ID NO: 145

CXXRRXSXXXXCY, wherein the serine residue can be phosphorylated.             SEQ ID NO: 146

XXXXXXXXXXX, wherein X is any amino acid residue.                            SEQ ID NO: 147

XXXXXX, wherein X is any amino acid residue.                                 SEQ ID NO: 148

XXXXXSPXXXX, wherein X is any amino acid residue.                            SEQ ID NO: 149

XXXXRRXSXXXX, wherein X is any amino acid residue and the serine residue can be phosphorylated.          SEQ ID NO: 150

XXXXSPXXXX, wherein X is any amino acid residue and the serine residue can be phosphorylated.            SEQ ID NO: 151

RKSTTG(X)$_n$GKAP, wherein X is any amino acid residue, n is 1 to 10 amino acid residues, the lysine residues can be methylated or acetylated, and the serine residue can be phosphorylated.          SEQ ID NO: 152

XXXXARTKQT, wherein X is any amino acid residue, the lysine residue can be methylated, and the threonine residue can be phosphorylated.          SEQ ID NO: 153

YIY(P)GSFKKKYFGVHS          SEQ ID NO: 154

YIY(P)GSFKKKESVYIE          SEQ ID NO: 155

YIY(P)GSFKKKYFNAINT         SEQ ID NO: 156

YIY(P)GSFKKKNYHYEIEY        SEQ ID NO: 157

YIY(P)GSFKKKNYTWYVSY        SEQ ID NO: 158

YIY(P)GSFKKKDQEFTAFM        SEQ ID NO: 159

| SEQ ID NO: 160 | YIY(P)GSFKKKDRMFTTWSD |
| SEQ ID NO: 161 | YIY(P)GSFKKKFMLWMDETY |
| SEQ ID NO: 162 | YIY(P)GSFKKKFMLWMDETYG |
| SEQ ID NO: 163 | EAIY(P)AAPFAKKYTFELT |
| SEQ ID NO: 164 | EAIY(P)AAPFAKKGYWGWFTF |
| SEQ ID NO: 165 | EAIY(P)AAPFAKKLYIMDGWF |
| SEQ ID NO: 166 | LRRAS(P)LPFMMLWLWSK |
| SEQ ID NO: 167 | LRRAS(P)LREIFVSEWM |
| SEQ ID NO: 168 | RPYQIKDQSVNI |
| SEQ ID NO: 169 | QAFRYERDRWER |
| SEQ ID NO: 170 | DDAITGRYSIGE |
| SEQ ID NO: 171 | DFDYYGPTMWSE |
| SEQ ID NO: 172 | EAIYAAPFAKKYTFELT |
| SEQ ID NO: 173 | EAIYAAPFAKKFFQGYWF |
| SEQ ID NO: 174 | LRRASLFYGMWYPST |
| SEQ ID NO: 175 | YIYGSFKKKPVWFFRW |
| SEQ ID NO: 176 | IYGSFKKKPVWFFRW |
| SEQ ID NO: 177 | YGSFKKKPVWFFRW |
| SEQ ID NO: 178 | YIYGSFKKKVVDTHYQE |
| SEQ ID NO: 179 | IYGSFKKKVVDTHYQE |
| SEQ ID NO: 180 | YGSFKKKVVDTHYQE |
| SEQ ID NO: 181 | DAITGRYSIGE |
| SEQ ID NO: 182 | AITGRYSIGE |
| SEQ ID NO: 183 | $X_1X_2X_3X_4X_5X_6X_7X_8X_9X_{10}X_{11}X_{12}$ |
| SEQ ID NO: 184 | $X_1X_2X_3X_4TGRX_8SX_{10}GX_{12}$ |
| SEQ ID NO: 185 | $X_1X_2X_3X_4X_5GX_7X_8X_9X_{10}X_{11}E$ |
| SEQ ID NO: 186 | $DX_2X_3X_4X_5GX_7X_8X_9X_{10}X_{11}E$ |
| SEQ ID NO: 187 | YIY(P)$_n$GSFKKK-$X_1X_2X_3X_4X_5X_6X_7X_8X_9X_{10}$ |
| SEQ ID NO: 188 | EAIY(P)$_n$AAPFAKK-$X_1X_2X_3X_4X_5X_6X_7X_8$ |
| SEQ ID NO: 189 | LRRAS(P)$_n$L-$X_1X_2X_3X_4X_5X_6X_7X_8X_9X_{10}$ |
| SEQ ID NO: 190 | YIYGSFKKKYFGVHS |
| SEQ ID NO: 191 | YIYGSFKKKESVYIE |
| SEQ ID NO: 192 | YIYGSFKKKYFNAINT |
| SEQ ID NO: 193 | YIYGSFKKKNYHYEIEY |
| SEQ ID NO: 194 | YIYGSFKKKNYTWYVSY |
| SEQ ID NO: 195 | YIYGSFKKKDQEFTAFM |
| SEQ ID NO: 196 | YIYGSFKKKDRMFTTWSD |
| SEQ ID NO: 197 | YIYGSFKKKFMLWMDETY |
| SEQ ID NO: 198 | YIYGSFKKKFMLWMDETYG |
| SEQ ID NO: 199 | EAIYAAPFAKKYTFELT |
| SEQ ID NO: 200 | EAIYAAPFAKKGYWGWFTF |
| SEQ ID NO: 201 | EAIYAAPFAKKLYIMDGWF |
| SEQ ID NO: 202 | LRRASLPFMMLWLWSK |
| SEQ ID NO: 203 | LRRASLREIFVSEWM |
| SEQ ID NO: 204 | DAYWDGTGHIYE |

What is claimed is:

1. A method of detecting a peptide, comprising:
contacting the peptide with an organic dye and a chelating metal ion, such that the peptide specifically binds to the dye changing the fluorescence properties of the dye, wherein the peptide is 12 to 100 amino acids in length and is conformationally constrained by the chelating metal ion, and wherein the organic dye is selected from the group consisting of triarylmethane dyes, benzylidene imidazolinone dyes, and variants thereof; and detecting the change in fluorescence properties of the dye, thereby detecting the peptide, wherein the peptide comprises the formula:

$$DX_2X_3X_4X_5GX_7X_8X_9X_{10}X_{11}E,$$ (IIb) (SEQ ID NO: 186)

wherein:
each of $X_2$, $X_3$, $X_4$, and $X_5$ is an amino acid independently selected from the group consisting of D, A, Y, and W, wherein at least one of $X_2$, $X_3$, $X_4$, and $X_5$ is D and at least one of $X_2$, $X_3$, $X_4$, and $X_5$ is W; and
each of $X_7$, $X_8$, $X_9$, $X_{10}$, and $X_{11}$ is an amino acid independently selected from the group consisting of V, L, I, M, F, N, E, Q, H, K, R, D, G, A, S, T, Y, W, C and P.

2. The method of claim 1, wherein the peptide is 12 to 50 amino acids in length.

3. The method of claim 1, wherein the peptide is a linear peptide.

4. The method of claim 1, wherein the peptide is a peptide cyclized by a disulfide bond.

5. The method of claim 1, wherein the chelating metal ion is $Ca^{2+}$ or $Zn^{2+}$.

6. The method of claim 1, wherein the peptide has at least one post-translational modification.

7. The method of claim 1, wherein the peptide is further fused to a protein.

8. The method of claim 7, wherein the protein comprises a targeting moiety.

9. The method of claim 8, wherein the targeting moiety comprises an antibody, antibody fragment, peptide aptamer or variant thereof.

10. The method of claim 8, wherein the targeting moiety comprises a viral protein.

11. The method of claim 8, wherein the targeting moiety comprises an ion channel or a membrane receptor.

12. The method of claim 1, wherein the peptide is selected from the group consisting of:

DAYWDGTGHIYE, (SEQ ID NO: 204)

DWWDWGNHGYTE, (SEQ ID NO: 31)
and

DWWWDGFERLEE. (SEQ ID NO: 23)

* * * * *